(12) United States Patent
Jin et al.

(10) Patent No.: US 6,500,863 B1
(45) Date of Patent: Dec. 31, 2002

(54) HYDROXY DIPHENYL UREA SULFONAMIDES AS IL-8 RECEPTOR ANTAGONISTS

(75) Inventors: Qi Jin, King of Prussia, PA (US); Brent W. McCleland, Greenlane, PA (US); Michael R. Palovich, Norristown, PA (US); Katherine L. Widdowson, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/868,165

(22) PCT Filed: Dec. 15, 1999

(86) PCT No.: PCT/US99/29940

§ 371 (c)(1),
(2), (4) Date: Jun. 13, 2001

(87) PCT Pub. No.: WO00/35442

PCT Pub. Date: Jun. 22, 2000

Related U.S. Application Data

(60) Provisional application No. 60/112,481, filed on Dec. 16, 1998, and provisional application No. 60/137,003, filed on Jun. 1, 1999.

(51) Int. Cl.⁷ .............................................. A61K 31/17
(52) U.S. Cl. .............................. 514/593; 564/51; 546/1; 548/400; 549/200
(58) Field of Search ................................ 514/593, 592, 514/588; 564/32, 47, 48, 51; 546/1; 548/215, 233, 240, 356.1, 400, 566; 549/200; 544/106; 540/484

(56) References Cited

U.S. PATENT DOCUMENTS

| 4,155,930 A | 5/1979 | Siuta et al. |
| 4,786,316 A | 11/1988 | Tseng |

OTHER PUBLICATIONS

Streiweiser, A. and Heathcock, C.: "Introduction to Organic Chemistry" 1981, MacMillan Publishing Co., Inc. US XP002204853 p. 695.

Database Caplus on STN, *Chem Abstracts*, (Columbus OH, USA) No. 128:110869, Widdowson, K., "Phenyl urea interleukin-8 receptor antagonists for treatment of interleukin-8-mediated diseases and preparation thereof", abstract WO9749286, Dec. 1997.

Database Caplus on STN, *Chem Abstracts*, (Columbus OH, USA) No. 128:110887, Widdowson, K., "Phenylurea Il-8 receptor antagonists, preparation thereof and therapeutic use", abstract WO9749400, Dec. 1997.

Database Caplus on STN, *Chem Abstracts*, (Columbus OH, USA) No. 130:38286, Ranges, G. et al. "Inhibition of p38 kinase activity by aryl ureas", abstract WO9852558, Nov. 1998.

*Primary Examiner*—Jean F. Vollano
(74) *Attorney, Agent, or Firm*—Soma G. Simon; Mary E. McCarthy; Charles M. Kinzig

(57) ABSTRACT

Novell IL-8 compounds and methods of using them are provided.

16 Claims, No Drawings

HYDROXY DIPHENYL UREA SULFONAMIDES AS IL-8 RECEPTOR ANTAGONISTS

This application is a §371 of PCT/US99/29940, filed on Dec. 15, 1999, which claims benefit of U.S. provisional application number 60/112,481, filed Dec. 16, 1998 and which claims benefit of U.S. provisional application number 60/137,003, filed Jun. 1, 1999.

FIELD OF THE INVENTION

This invention relates to novel sulfonamide substituted diphenyl urea compounds, pharmaceutical compositions, processes for their preparation, and use thereof in treating IL-8, GROα, GROβ, GROγ, NAP-2 and ENA-78 mediated diseases.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al., *J. Clin. Invest.* 84, 1045 (1989): J. Schroder et al, *J. Immunol.* 139, 3474 (1987) and *J. Immunol.* 144, 2223 (1990); Strieter, et al., *Science* 243, 1467 (1989) and *J. Biol. Chem.* 264, 10621 (1989); Cassatella et al., *J. Immunol.* 148, 3216 (1992).

GROα, GROβ, GROγ and NAP-2 also belong to the chemokine family. Like IL-8 these chemokines have also been referred to by different names. For instance GROα, β, γ have been referred to as MGSAα, β and γ respectively (Melanoma Growth Stimulating Activity), see Richmond et al., *J. Cell Physiology* 129, 375 (1986) and Chang et al., *J. Immunol* 148, 451 (1992). All of the chemokines of the α-family which possess the ELR motif directly preceding the CXC motif bind to the IL-8 B receptor (CXCR2). IL-8, GROα, GROβ, GROγ, NAP-2, and ENA-78 stimulate a number of functions in vitro. They have all been shown to have chemoattractant properties for neutrophils, while IL-8 and GROα have demonstrated T-lymphocytes, and basophilic chemotactic activity. In addition IL-8 can induce histamine release from basophils from both normal and atopic individuals. GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, GROα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al., *FEBS Lett.* 307, 97 (1992); Miller et al., *Crit. Rev. Immunol.* 12, 17 (1992); Oppenheim et al., *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis, Strieter et al., *Science* 258, 1798 (1992).

In vitro, IL-8, GROα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the IL-85βreceptor (CXCR2). Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research, Vol. 40*, pp. 33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8Rβ, which has high affinity for IL-8 as well as for GROα, GROβ, GROγ and NAP-2. See Holmes et al., supra; Murphy et al., *Science* 253, 1280 (1991); Lee et al., *J. Biol. Chem.* 267, 16283 (1992); LaRosa et al., *J. Biol. Chem.* 267, 25402 (1992); and Gayle et al., *J. Biol. Chem.* 268, 7283 (1993).

There remains a need for treatment, in this field, for compounds, which are capable of binding to the IL-8α or β receptor. Therefore, conditions associated with an increase in IL-8 production (which is responsible for chemotaxis of neutrophil and T-cells subsets into the inflammatory site) would benefit by compounds, which are inhibitors of IL-8 receptor binding.

SUMMARY OF THE INVENTION

This invention provides for a method of treating a chemokine mediated disease, wherein the chemokine is one which binds to an IL-8a or b receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective amount of a compound of Formula (I).

The present invention also provides for the novel compounds of Formula (I), and pharmaceutical compositions comprising a compound of Formula (I), and a pharmaceutical carrier or diluent.

Compounds of Formula (I) useful in the present invention are represented by the structure:

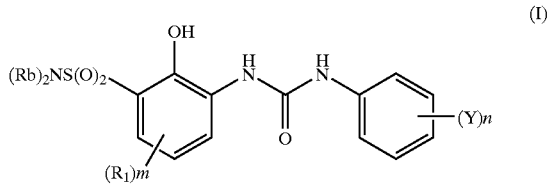

wherein $R_b$ is independently hydrogen, $NR_6R_7$, OH, $OR_a$, $C_{1-5}$alkyl, aryl, aryl$C_{1-4}$alkyl, aryl $C_{2-4}$alkenyl; cycloalkyl, cycloalkyl $C_{1-5}$alkyl, heteroaryl, heteroaryl$C_{1-4}$alkyl, heteroaryl$C_{2-4}$alkenyl, heterocyclic, heterocyclic $C_{1-4}$alkyl, or a heterocyclic $C_{2-4}$alkenyl moiety, all of which moieties may be optionally substituted one to three times independently by halogen; nitro; halosubstituted $C_{1-4}$alkyl; $C_{1-4}$ alkyl; amino, mono or di-$C_{1-4}$alkyl substituted amine; $OR_a$; $C(O)R_a$; $NR_aC(O)OR_a$; $OC(O)NR_6R_7$; hydroxy; $NR_9C(O)R_a$; $S(O)_m$, $R_a$; $C(O)NR_6R_7$; $C(O)OH$; $C(O)OR_a$; $S(O)_t NR_6R_7$; $NHS(O)_tR_a$. Alternatively, the two $R_b$ substituents can join to form a 3–10 membered ring, optionally substituted and containing, in addition to optionally substituted $C_{1-4}$alkyl, independently, 1 to 3 $NR_a$, O, S, SO, or $S_2$ moities which can be optionally unsaturated;

$R_a$ is an alkyl, aryl, aryl$C_{1-4}$alkyl, heteroaryl, heteroaryl $C_{1-4}$alkyl, heterocyclic, $COOR_a'$, or a heterocyclic $C_{1-4}$alkyl moiety, all of which moieties may be optionally substituted;

$R_a'$ is an alkyl, aryl, aryl$C_{1-4}$alkyl, heteroaryl, heteroaryl $C_{1-4}$alkyl, heterocyclic or a heterocyclic $C_{1-4}$alkyl moiety, all of which moieties may be optionally substituted;

m is an integer having a value of 1 to 3;
m' is 0, or an integer having a value of 1 or 2;
n is an integer having a value of 1 to 3;
q is 0, or an integer having a value of 1 to 10;
t is 0, or an integer having a value of 1 or 2;
s is an integer having a value of 1 to 3;

$R_1$ is independently selected from hydrogen, halogen, nitro, cyano, $C_{1-10}$ alkyl, halosubstituted $C_{1-10}$alkyl, $C_{2-10}$alkenyl, $C_{1-10}$alkoxy, halosubstituted $C_{1-10}$alkoxy, azide, $S(O)_tR_4$, $(CR_8R_8)q\ S(O)_tR_4$, hydroxy, hydroxy substituted $C_{1-4}$alkyl, aryl, aryl $C_{1-4}$alkyl, aryl $C_{2-10}$alkenyl, aryloxy, aryl $C_{1-4}$ alkyloxy, heteroaryl, heteroarylalkyl, heteroaryl $C_{2-10}$ alkenyl, heteroaryl $C_{1-4}$ alkyloxy, heterocyclic, heterocyclic $C_{1-4}$alkyl, heterocyclic$C_{1-4}$alkyloxy, heterocyclic$C_{2-10}$ alkenyl, $(CR_8R_8)q\ NR_4R_5$, $(CR_8R_8)qC(O) NR_4R_5$, $C_{2-10}$ alkenyl $C(O)NR_4R_5$, $(CR_8R_8)q\ C(O)NR_4R_{10}$, $S(O)_3R_8$, $(CR_8R_8)q\ C(O)R_{11}$, $C_{2-10}$ alkenyl $C(O)R_{11}$, $C_{2-10}$alkenyl $C(O)OR_{11}$, $(CR_8R_8)q\ C(O)OR_{11}$, $(CR_8R_8)q OC(O)R_{11}$, $(CR_8R_8)qNR_4C(O)R_{11}$, $(CR_8R_8)q\ C(NR_4) NR_4R_5$, $(CR_8R_8)q\ NR_4C(NR_5)R_{11}$, $(CR_8R_8)q\ NHS(O)_tR_{13}$, $(CR_8R_8)q\ S(O)_tNR_4R_5$, or two $R_1$ moieties together may form $O—(CH_2)_sO$ or a 5 to 6 membered saturated or unsaturated ring, and wherein the alkyl, aryl, arylalkyl, heteroaryl, heterocyclic moieties may be optionally substituted;

$R_4$ and $R_5$ are independently hydrogen, optionally substituted $C_{1-4}$alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$alkyl, or $R_4$ and $R_5$ together with the nitrogen to which they are attached form a 5 to 7 member ring which may optionally comprise an additional heteroatom selected from O, N and S;

$R_6$ and $R_7$ are independently hydrogen, or a $C_{1-4}$ alkyl, heteroaryl, aryl, aklyl aryl, alkyl $C_{1-4}$heteroalkyl, which may all be optionally substituted or $R_6$ and $R_7$ together with the nitrogen to which they are attached form a 5 to 7 member ring which ring may optionally contain an additional heteroatom is selected from oxygen, nitrogen or sulfur, and which ring may be optionally substituted;

Y is hydrogen, halogen, nitro, cyano, halosubstituted $C_{1-10}$ alkyl, $C_{1-10}$ alkyl, $C_{2-10}$ alkenyl, $C_{1-10}$ alkoxy, halosubstituted $C_{1-10}$ alkoxy, azide, $(CR_8R_8)qS(O)_tR_a$, $(CR_8R_8) OR_a$, hydroxy, hydroxy substituted $C_{1-4}$alkyl, aryl; aryl $C_{1-4}$ alkyl, aryloxy, aryl$C_{1-4}$alkyloxy, aryl$C_{2-10}$ alkenyl, heteroaryl, heteroarylalkyl, heteroaryl $C_{1-4}$ alkyloxy, heteroaryl $C_{2-10}$ alkenyl, heterocyclic, heterocyclic $C_{1-4}$alkyl, heterocyclic$C_{2-10}$ alkenyl, $(CR_8R_8)qNR_4R_5$, $C_{2-10}$ alkenyl $C(O)NR_4R_5$, $(CR_8R_8)qC(O)NR_4R_5$, $(CR_8R_8)q\ C(O) NR_4R_{10}$, $S(O)_3R_8$, $(CR_8R_8)qC(O)R_{11}$, $C_{2-10}$alkenylC(O) $R_{11}$, $(CR_8R_8)qC(O)OR_{11}$, $C_{2-10}$alkenylC(O)OR$_{11}$, $(CR_8R_8) qOC(O)R_{11}$, $(CR_8R_8)qNR_4C(O)R_{11}$, $(CR_8R_8)q\ NHS(O)_t R_{13}$, $(CR_8R_8)q\ S(O)_tNR_4R_5$, $(CR_8R_8)qC(NR_4)NR_4R_5$, $(CR_8R_8)q\ NR_4C(NR_5)R_{11}$, or two Y moieties together may form $O—(CH_2)_s—O$ or a 5 to 6 membered saturated or unsaturated ring, and wherein the alkyl, aryl, arylalkyl, heteroaryl, heteroaryl alkyl, heterocyclic, heterocyclicalkyl groups may be optionally substituted;

$R_8$ is hydrogen or $C_{1-4}$ alkyl;
$R_9$ is hydrogen or a $C_{1-4}$alkyl;
$R_{10}$ is $C_{1-10}$ alkyl $C(O)_2R_8$;
$R_{11}$ is hydrogen, optionally substituted $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl;
$R_{13}$ is suitably $C_{1-4}$ alkyl, aryl, aryl $C_{1-4}$alkyl, heteroaryl, heteroaryl$C_{1-4}$alkyl, heterocyclic, or heterocyclic$C_{1-4}$alkyl; or a pharmaceutically acceptable salt thereof.

DETAILED DESCRIPTION OF THE INVENTION

The compounds of Formula (I), may also be used in association with the veterinary treatment of mammals, other than humans, in need of inhibition of IL-8 or other chemokines which bind to the IL-8α and β receptors. Chemokine mediated diseases for treatment, therapeutically or prophylactically, in animals include disease states such as those noted herein in the Methods of Treatment section.

Suitably, $R_b$ is independently hydrogen, $NR_6R_7$, OH, $OR_a$, $C_{1-4}$alkyl, aryl, aryl$C_{1-4}$alkyl, aryl $C_{2-4}$alkenyl, heteroaryl, heteroaryl$C_{1-4}$alkyl, heteroaryl$C_{2-4}$alkenyl, heterocyclic, heterocyclic $C_{1-4}$alkyl, or a heterocyclic $C_{2-4}$alkenyl moiety, all of which moieties may be optionally substituted one to three times independently by halogen, nitro, halosubstituted $C_{1-4}$alkyl, $C_{1-4}$alkyl, amino, mono or di-$C_{1-4}$ alkyl substituted amine, cycloalkyl, cycloalkyl $C_{1-5}$alkyl, $OR_a$, $C(O)R_a$, $NR_aC(O)OR_a$, $OC(O)NR_6R_7$, aryloxy, aryl $C_{1-4}$oxy, hydroxy, $C_{1-4}$alkoxy, $NR_9C(O)R_a$, $S(O)_m$, $R_a$, $C(O)NR_6R_7$, $C(O)OH$, $C(O)OR_a$, $S(O)_tNR_6R_7$, $NHS(O)_tR_a$. Alternatively, the two $R_b$ substituents can join to form a 3–10 membered ring, optionally substituted and containing, in addition to carbon, independently, 1 to 3 $NR_9$, O, S, SO, or $SO_2$ moities which can be optionally substituted.

Suitably, $R_a$ is an alkyl, aryl, aryl$C_{1-4}$alkyl, heteroaryl, heteroaryl $C_{1-4}$alkyl, heterocyclic, or a heterocyclic $C_{1-4}$alkyl moiety, all of which moieties may be optionally substituted.

Suitably, $R_1$ is independently selected from hydrogen; halogen; nitro; cyano; halosubstituted $C_{1-10}$ alkyl, such as $CF_3$, $C_{1-10}$ alkyl, such as methyl, ethyl, isopropyl, or n-propyl, $C_{2-10}$ alkenyl, $C_{1-10}$ alkoxy, such as methoxy, or ethoxy; halosubstituted $C_{1-10}$ alkoxy, such as trifluoromethoxy, azide, $(CR_8R_8)q\ S(O)_tR_4$, wherein t is 0, 1 or 2, hydroxy, hydroxy $C_{1-4}$alkyl, such as methanol or ethanol, aryl, such as phenyl or naphthyl, aryl $C_{1-4}$ alkyl, such as benzyl, aryloxy, such as phenoxy, aryl $C_{1-4}$ alkyloxy, such as benzyloxy; heteroaryl, heteroarylalkyl, heteroaryl $C_{1-4}$ alkyloxy; aryl $C_{2-10}$ alkenyl, heteroaryl $C_{2-10}$alkenyl, heterocyclic $C_{2-10}$ alkenyl, $(CR_8R_8)qR_4R_5$, $C_{2-10}$ alkenyl $C(O)NR_4R_5$, $(CR_8R_8)qC(O)NR_4R_5$, $(CR_8R_8)qC(O)NR_4R_{10}$, $S(O )_3H$, $S(O )_3R_8$, $(CR_8R_8)qC(O)R_{11}$, $C_{2-10}$ alkenyl $C(O)R_{11}$, $C_{2-10}$ alkenyl $C(O)OR_{11}$, $(CR_8R_8)q\ C(O)R_{11}$, $(CR_8R_8)qC(O)OR_{11}$, $(CR_8R_8)q\ OC(O)R_{11}$, $(CR_8R_8)qNR_4C(O)R_{11}$, $(CR_8R_8)qC(NR_4)NR_4R_5$, $(CR_8R_8)q\ NR_4C(NR_5)R_{11}$, $(CR_8R_8)qNHS(O)_tR_{13}$, $(CR_8R_8)qS(O)_tNR_4R_5$. All of the aryl, heteroaryl, and heterocyclic-containing moieties may be optionally substituted as defined herein below.

For use herein the term "the aryl, heteroaryl, and heterocyclic containing moieties" refers to both the ring and the alkyl, or if included, the alkenyl rings, such as aryl, arylalkyl, and aryl alkenyl rings. The term "moieties" and "rings" may be interchangeably used throughout.

Suitably, $R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O, N and S.

Suitably, $R_8$ is independently hydrogen or $C_{1-4}$ alkyl.

Suitably, $R_9$ is hydrogen or a $C_{1-4}$ alkyl;

Suitably, q is 0 or an integer having a value of 1 to 10.

Suitably, $R_{10}$ is $C_{1-0}$ alkyl $C(O)_2R_8$, such as $CH_2C(O)_2H$ or $CH_2C(O)_2CH_3$.

Suitably, $R_{11}$ is hydrogen, $C_{1-4}$ alkyl, aryl, aryl $C_{1-4}$ alkyl, heteroaryl, heteroaryl $C_{1-4}$alkyl, heterocyclic, or heterocyclic $C_{1-4}$alkyl.

Suitably, $R_{12}$ is hydrogen, $C_{1-10}$ alkyl, optionally substituted aryl or optionally substituted arylalkyl.

Suitably, $R_{13}$ is $C_{1-4}$alkyl, aryl, arylalkyl, heteroaryl, heteroaryl $C_{1-4}$alkyl, heterocyclic, or heterocyclic$C_{1-4}$alkyl, wherein all of the aryl, heteroaryl and heterocyclic containing moieties may all be optionally substituted.

Suitably, Y is independently selected from hydrogen; halogen; nitro; cyano; halosubstituted $C_{1-10}$ alkyl; $C_{1-10}$alkyl; $C_{2-10}$ alkenyl; $C_{1-10}$ alkoxy; halosubstituted $C_{1-10}$ alkoxy; azide; $(CR_8R_8)q\ S(O)_tR_a$; hydroxy; hydroxy$C_{1-4}$alkyl; aryl; aryl $C_{1-4}$ alkyl; aryloxy; aryl$C_{1-4}$ alkyloxy; heteroaryl; heteroarylalkyl; heteroaryl $C_{1-4}$alkyloxy; heterocyclic, heterocyclic $C_{1-4}$alkyl; aryl $C_{2-10}$ alkenyl; heteroaryl $C_{2-10}$ alkenyl; heterocyclic $C_{2-10}$ alkenyl; $(CR_8R_8)q\ NR_4R_5$; $C_{2-10}$alkenyl $C(O)NR_4R_5$; $(CR_8R_8)q\ C(O)NR_4R_5$; $(CR_8R_8)q\ C(O)NR_4R_{10}$; $S(O)_3H$; $S(O)_3R_8$; $(CR_8R_8)q\ C(O)R_{11}$; $C_{2-10}$ alkenyl $C(O)R_{11}$; $C_{2-10}$ alkenyl $C(O)OR_{11}$; $(CR_8R_8)q\ C(O)OR_{12}$; $(CR_8R_8)q\ OC(O)R_{11}$; $(CR_8R_8)qC(NR_4)NR_4R_5$; $(CR_8R_8)q\ NR_4C(NR_5)R_{11}$; $(CR_8R_8)q\ NR_4C(O)R_{11}$; $(CR_8R_8)q\ NHS(O)_tR_{13}$; or $(CR_8R_8)q\ S(O)_tNR_4R_5$; or two Y moieties together may form $O—(CH_2)_s—O$ or a 5 to 6 membered saturated or unsaturated ring. The aryl, heteroaryl and heterocyclic containing moieties noted above may all be optionally substituted as defined herein.

Suitably s is an integer having a value of 1 to 3.

When Y forms a dioxybridge, s is preferably 1. When Y forms an additional unsaturated ring, it is preferably 6 membered resulting in a naphthylene ring system. These ring systems may be substituted 1 to 3 times by other Y moieties as defined above.

Suitably, $R_a$ is an alkyl, aryl $C_{1-4}$ alkyl, heteroaryl, heteroaryl-$C_{1-4}$alkyl, heterocyclic, or a heterocyclic$C_{1-4}$alkyl, wherein all of these moieties may all be optionally substituted.

Y is preferably a halogen, $C_{1-4}$alkoxy, optionally substituted aryl, optionally substituted aryloxy or arylalkoxy, methylene dioxy, $NR_4R_5$, thio $C_{1-4}$alkyl, thioaryl, halosubstituted alkoxy, optionally substituted $C_{1-4}$alkyl, or hydroxy alkyl. Y is more preferably mono-substituted halogen, disubstituted halogen, mono-substituted alkoxy, disubstituted alkoxy, methylenedioxy, aryl, or alkyl, more preferably these groups are mono or di-substituted in the 2'- position or 2'-, 3'-position.

While Y may be substituted in any of the ring positions, n is preferably one. While both $R_1$ and Y can both be hydrogen, it is preferred that at least one of the rings is substituted, preferably both rings are substituted.

As used herein, "optionally substituted" unless specifically defined shall mean such groups as halogen, such as fluorine, chlorine, bromine or iodine, hydroxy; hydroxy substituted $C_{1-10}$alkyl, $C_{1-10}$alkoxy, such as methoxy or ethoxy, $S(O)_m'C_{1-10}$ alkyl, wherein m' is 0, 1 or 2, such as methyl thio, methyl sulfonyl or methyl sulfonyl; amino, mono & di-substituted amino, such as in the $NR_4R_5$ group, $NHC(O)R_4$, $C(O)NR_4R_5$, $COOR_4$, $S(O)_tNR_4R_5$, $NHS(O)_tR_{20}$, $C_{1-10}$alkyl, such as methyl, ethyl, propyl, isopropyl, or t-butyl, halosubstituted $C_{1-10}$ alkyl, such $CF_3$, an optionally substituted aryl, such as phenyl, or an optionally substituted arylalkyl, such as benzyl or phenethyl, optionally substituted heterocylic, optionally substituted heterocyclicalkyl, optionally substituted heteroaryl, optionally substituted heteroaryl alkyl, wherein these aryl, heteroaryl, or heterocyclic moieties may be substituted one to two times by halogen; hydroxy; hydroxy substituted alkyl, $C_{1-10}$ alkoxy; $S(O)_m$ $C_{1-10}$ alkyl; amino, mono & di-substituted alkyl amino, such as in the $NR_4R_5$ group; $C_{1-10}$alkyl, or halosubstituted $C_{1-10}$ alkyl, such as $CF_3$.

$R_{20}$ is suitably $C_{1-4}$alkyl, aryl, aryl $C_{1-4}$alkyl, heteroaryl, heteroaryl$C_{1-4}$alkyl, heterocyclic, or heterocyclic$C_{1-4}$alkyl.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation. Suitable pharmaceutically acceptable cations are well known to those skilled in the art and include alkaline, alkaline earth, ammonium and quaternary ammonium cations.

The following terms, as used herein, refer to:

"halo" - all halogens, that is chloro, fluoro, bromo and iodo.

"$C_{1-10}$alkyl" or "alkyl" - both straight and branched chain moieties of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic moiety, preferably of 3 to 8 carbons, including but not limited to cyclopropyl, cyclopentyl, cyclohexyl, and the like.

"alkenyl" is used herein at all occurrences to mean straight or branched chain moiety of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl" - phenyl and naphthyl;

"heteroaryl" (on its own or in any combination, such as "heteroaryloxy", or "heteroaryl alkyl") - a 5–10 membered aromatic ring system in which one or more rings contain one or more heteroatoms selected from the group consisting of N, O, or S, such as, but not limited, to pyrrole, pyrazole, furan, thiophene, quinoline, isoquinoline, quinazolinyl, pyridine, pyrimidine, oxazole, tetrazole, thiazole, thiadiazole, triazole, imidazole, or benzimidazole.

"heterocyclic" (on its own or in any combination, such as "heterocyclicalkyl") - a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, thiomorpholine, or imidazolidine. Furthermore, sulfur may be optionally oxidized to the sulfone or the sulfoxide.

"arylalkyl" or "heteroarylalkyl" or "heterocyclicalkyl" is used herein to mean $Cl_{1-10}$ alkyl, as defined above, attached to an aryl, heteroaryl or heterocyclic moiety, as also defined herein, unless otherwise indicated.

"sulfinyl" - the oxide S (O ) of the corresponding sulfide, the term "thio" refers to the sulfide, and the term "sulfonyl" refers to the fully oxidized $S(O)_2$ moiety.

"wherein two $R_1$ moieties (or two Y moieties) may together form a 5 or 6 membered saturated or unsaturated ring" is used herein to mean the formation of an aromatic ring system, such as naphthalene, or is a phenyl moiety having attached a 6 membered partially saturated or unsaturated ring such as a $C_6$ cycloalkenyl, i.e. hexene, or a $C_5$ cycloalkenyl moiety, such as cyclopentene.

Illustrative compounds of Formula (I) include:

N-(2-Hydroxyl-3-aminosulfonyl4-chlorophenyl)-N'-(2-bromophenyl) urea;

N-(2-Hydroxy-3-aminosulfonyl4-chlorophenyl)-N'(2,3-dichlorophenyl) urea;

N-(2-Hydroxy-3-N"-benzylaminosulfonyl-4-chlorophenyl)-N'-(2-bromophenyl) urea;

N-(2-Hydroxy-3-N"-benzylaminosulfonyl-4-chlorophenyl)-N'(2,3-dichlorophenyl) urea;

N-[2-Hydroxy-3-(N",N"-dimethyl)-aminosulfonyl-4-chlorophenyl]-N'(2,3-dichlorophenyl) urea;

N-(2-Hydroxy-3-N",N"-dimethylaminosulfonyl-4-chlorophenyl)-N'-(2-bromophenyl) urea;

N-(2-Hydroxy-3-N"-methylaminosulfonyl-4-chlorophenyl)-N'-(2-bromophenyl) urea;

N-(2-Hydroxy-3-N"-methylaminosulfonyl-4-chlorophenyl)-N'(2,3-dichlorophenyl) urea;

N-[2-Hydroxy-3-[N-(methoxycarbonylmethyl) aminosulfonyl-4-chlorophenyl]-N'(2,3-dichlorophenyl) urea;

N-[2-Hydroxy-3-(N"-(2-methoxylcarbonyl)-methyl)-aminosulfonyl-4-chlorophenyl]-N'-(2-bromophenyl) urea;

N-[2-Hydroxy-3-[(N"-2-carboxymethyl)-aminosulfonyl]-4-chlorophenyl]-N'-(2,3-dichlorophenyl) urea;

N-[2-Hydroxy-3-(N"-2-carboxymethyl)-aminosulfonyl-4-chlorophenyl]-N'(2-bromophenyl) urea;

N-[2-Hydroxy-3-aminosulfonyl-4-chlorophenyl]-N'-(2-chlorophenyl) urea;

N-[2-Hydroxy-3-aminosulfonyl-4-chlorophenyl]-N'phenyl urea;

N-(2-Hydroxy-3-aminosulfonyl-4-chlorophenyl)-N'-(2-phenoxyphenyl) urea;

N-(2-Hydroxy-3-[N'''-(3-carboxyethyl)-aminosulfonyl-4-chlorophenyl)-N'(2-bromophenyl) urea;

N-[2-Hydroxy-3-(isopropylaminosulfonyl)-4-chlorophenyl]-N'-(2-bromophenyl) urea;

N-[2-Hydroxy-3-(isopropylaminosulfonyl)-4-chlorophenyl]-N'-(2-chlorophenyl) urea;

N-[2-Hydroxy-3-(isopropylaminosulfonyl)-4-chlorophenyl]-N'-(2,3-dichlorophenyl) urea;

N-(4-chloro-2-hydroxy-3-aminosulfonylphenyl)-N'(2-methoxyphenyl) urea;

N-(4-chloro-2-hydroxy-3-aminosulfonylphenyl)-N'(2,3-methylenedioxy phenyl) urea;

N-(2-benzyloxyphenyl)-N'(4-chloro-2-hydroxy-3-aminosulfonylphenyl) urea;

N-[3-(N"-allylaminosulfonyl)-4-chloro-2-hydroxyphenyl]-N'(2,3-dichlorophenyl) urea;

N-[4-chloro-2-hydroxy-3-[N"-(2-trifluoroethyl) aminosulfonyl]phenyl-N'-(2,3-dichlorophenyl) urea;

N-(2,3-dichlorophenyl)-N'[2-hydroxy-4-methoxy-3-N"-(phenylaminosulfonyl)phenyl] urea;

N-(2-bromophenyl)-N'-[2-hydroxy-4-methoxy-3-N"-(phenylaminosulfonyl)phenyl] urea;

N-[4-chloro-2-hydroxy-3-[N"-(2-methoxyethyl) aminosulfonyl]phenyl]-N'(2,3-dichlorophenyl) urea;

N-(2-bromophenyl)-N'-[4-chloro-2-hydroxy-3-[N"-(2-methoxyethyl)aminosulfonyl]phenyl] urea;

N-(2-bromophenyl)-N'-[4-chloro2-hydroxy-3-(4-morpholinylsulfonyl)phenyl] urea;

N-[4-chloro-2-hydroxy-3-(4-morpholinylsulfonyl) phenyl]-N'-(2,3-dichlorophenyl) urea;

N-[3-[N"-[3-(tert-butoxycarbonylamino)propyl] aminosulfonyl]-4-chloro-2-hydroxyphenyl]-N'-(2,3-dichlorophenyl) urea;

N-(2-bromophenyl)-N'-[3-[N"-[3-(tert-butoxycarbonylamino)propyl]aminosulfonyl]-4-chloro-2-hydroxyphenyl] urea;

N-[3-[N"-(3-aminopropyl)aminosulfonyl]-4-chloro-2-hydroxyphenyl]-N'-(2-bromophenyl) urea trifluoroacetate;

N-[3-[N-(3-aminopropyl)aminosulfonyl]-4-chloro-2-hydroxyphenyl]-N'-(2-bromophenyl) urea hydrochloride;

N-[3-[N"-(3-aminopropyl)aminosulfonyl]-4-chloro-2-hydroxyphenyl]-N'-(2,3-dichlorophenyl) urea trifluoroacetate;

N-(2-bromophenyl)-N'-[3-[N"-[2-(tert-butoxycarbonylamino)ethyl]aminosulfonyl]-4-chloro-2-hydroxyphenyl] urea;

N-[3-[N"-(2-aminoethyl)aminosulfonyl]-4-chloro-2-hydroxyphenyl]-N'(2-bromophenyl) urea;

N-(2-bromophenyl)-N'-[3-[[4-(tert-butoxycarbonyl) piperazin-1-yl]sulfonyl]-4-chloro-2-hydroxyphenyl] urea;

N-[3-[[4-(tert-butoxycarbonyl)piperazin-1-yl] sulfonyl]-4-chloro-2-hydroxyphenyl]-N'-(2,3-dichlorophenyl) urea;

N-[4-chloro-2-hydroxy-3-(1-piperazinylsulfonyl) phenyl]-N'-(2,3-dichlorophenyl) urea trifluoroacetate;

N-(2-bromophenyl)-N'-[4-chloro-2-hydroxy-3-(piperazin-1-ylsulfonyl)phenyl] urea trifluoroacetate;

N-[4-chloro-2-hydroxy-3-[N"-(3-methylthiopropyl) aminosulfonyl]phenyl]-N'-(2,3-dichlorophenyl) urea;

N-(2-bromophenyl)-N'-[4-chloro-2-hydroxy-3-[N"-(3-methylthiopropyl)aminosulfonyl]phenyl] urea;

N-(4-chloro-2-hydroxy-3-aminosulfonylphenyl)-N'-(2,3-dichlorophenyl) urea potasium salt;

N-(4-chloro-2-hydroxy-3-aminosulfonylphenyl)-N'(2,3-dichlorophenyl) urea sodium salt;

N-(2-bromophenyl)-N'[4-chloro-3-[N",N"-di-(2-methoxyethyl)aminosulfonyl]-2-hydroxyphenyl] urea;

N-[4-chloro-3-[N",N"-di-(2-methoxyethyl) aminosulfonyl]-2-hydroxyphenyl]-N'(2,3-dichlorophenyl) urea;

N-(2-bromophenyl)-N'[4-chloro-3-[N"-[2-(dimethylamino)ethyl]aminosulfonyl]-2-hydroxyphenyl] urea hydrochloride;

N-[4-chloro-3-(N"-[2-(dimethylamino)ethyl] aminosulfonyl-2-hydroxyphenyl]-N'-(2,3-dichlorophenyl) urea hydrochloride;

N-[4-chloro-2-hydroxy-3-[N"-[3-(methylsulfonyl)propyl]aminosulfonyl]phenyl]-N'-(2,3-dichlorophenyl) urea;

N-(2-bromophenyl)-N'-[4-chloro-2-hydroxy-3-[N"-[3-(methylsulfonyl)propyl]aminosulfonyl]phenyl] urea;

N-[4-chloro-2-hydroxy-3-[N"-[2-(morpholinyl)ethyl]aminosulfonyl]phenyl]-N'-(2,3-dichlorophenyl) urea hydrochloride;

N-[4-chloro-2-hydroxy-3-[N"-[2-(morpholinyl)ethyl]aminosulfonyl]phenyl]-N'-(2-chlorophenyl) urea hydrochloride;

N(2-bromophenyl)-N'-[4-chloro-2-hydroxy-3-[N"-[2-(4-morpholinyl)ethyl]aminosulfonyl]phenyl] urea;

N-[4-chloro-2-hydroxy-3-(4-thiomorpholinylsulfonyl)phenyl]-N'-(2,3-dichlorophenyl) urea;

N-(2-bromophenyl)-N'-[4-chloro-2-hydroxy-3-(4-thiomorpholinylsulfonyl)phenyl] urea;

N-(2-bromophenyl)-N'-[4-chloro-3-[N",N"-di-(2-hydroxyethyl)aminosulfonyl-2-hydroxyphenyl] urea;

N-[4-chloro-3-[N",N"-di-(2-hydroxyethyl)aminosulfonyl]-2-hydroxyphenyl]-N'-(2,3-dichlorophenyl) urea, N -[4-chloro-2-hydroxy-3-[N"-[3-(methylsulfinyl)propyl]aminosulfonyl]phenyl]-N'-(2,3-dichlorophenyl) urea;

N-(2-bromophenyl)-N'-[4-chloro-2-hydroxy-3-[N"-[3-(methylsulfinyl)propyl]aminosulfonylphenyl] urea;

N-(2-bromophenyl)-N'-[3-[N"-[(1-tert-butoxycarbonylpiperidin-4-yl)methyl]aminosulfonyl]-4-chloro2-hydroxyphenyl] urea, N-[3-[N"-[(1-tert-butoxycarbonylpiperidin-4-yl)methyl]aminosulfonyl]-4-chloro-2-hydroxyphenyl]-N'-(2,3-dichlorophenyl) urea;

N-[4-chloro-2-hydroxy-3-(1-oxidothiomorpholinosulfonyl)phenyl]-N'-(2,3-dichlorophenyl) urea;

N-(2-bromophenyl)-N'-[4-chloro-2-hydroxy-3-(1-oxidothiomorpholinosulfonyl)phenyl] urea;

N-[4-chloro2-hydroxy-3-[N"-[(piperidine-4-yl)methyl]aminosulfonyl]phenyl]-N'-(2,3-dichlorophenyl) urea trifluoroacetate;

N-(2-bromophenyl)-N'-[4-chloro-2-hydroxy-3-[N"-[(piperidin-4-yl)methyl]aminosulfonyl]phenyl] urea hydrochloride;

N-[3-(1-azetidinylsulfonyl)-4-chloro-2-hydroxyphenyl]-N'-(2-bromophenyl) urea;

N-[3-(1-azetidinylsulfonyl)-4-chloro-2-hydroxyphenyl]-N'-(2-chlorophenyl) urea;

N -[3-(1-azetidinylsulfonyl)-4-chloro-2-hydroxyphenyl]-N'-(2,3-dichlorophenyl) urea;

N-(2-bromophenyl)-N'-[4-chloro-3-(N",N"-dimethylaminosulfonyl)-2-hydroxyphenyl] urea potassium salt;

N-(2-bromophenyl)-N'-[4-chloro-3-(N",N"-dimethylaminosulfonyl)-2-hydroxyphenyl] urea sodium salt;

N-(2-bromophenyl)-N'[4-chloro-3-(N"-cyclopropylaminosulfonyl)-2-hydroxyphenyl) urea);

N-[4-chloro-3-(N"-cyclopropylaminosulfonyl)-2-hydroxyphenyl]-N'-(2-chlorophenyl) urea;

N-[4-chloro-3-(N"-cyclopropylaminosulfonyl)-2-hydroxyphenyl]-N'-(2,3-dichlorophenyl) urea;

N-(2-bromophenyl)-N'-[4-chloro-2-hydroxy-3-(N"-propylaminosulfonylphenyl] urea;

N-[4-chloro-2-hydroxyl-3-(N"-propylaminosulfonyl)phenyl]-N'-(2,3-dichlorophenyl) urea;

N [4-choro-2-hydroxyl-3-(N"-propylaminosulfonyl)phenyl]-N'-(2-chlorophenyl) urea;

N-(2-bromophenyl)-N [4-chloro-3-(N"-ethylaminosulfonyl])-2-hydroxyphenyl] urea;

N-[4-chloro-3-(N"-ethylaminosulfonyl)-2-hydroxyphenyl]-N'-(2-chlorophenyl) urea;

N-[4-chloro-3-(N"-ethylaminosulfonyl)-2-hydroxyphenyl]-N'(2,3-dichlorophenyl) urea;

N-(2-bromophenyl)-N'[3-[N"-[5-(tert-butoxycarbonylamino)-5-carboxylpentyl]aminosulfonyl]-4-chloro-2-hydroxyphenyl] urea;

N-[3-[N"-[5-(tert-butoxycarbonylamino)-5-carboxylpentyl]aminosulfonyl]-4-chloro-2-hydroxyphenyl]-N'-(2,3-dichlorophenyl) urea;

N-[3-[N"-[5-(tert-butoxycarbonylamino)-5-carboxylpentyl]aminosulfonyl]4-2-chloro-hydroxyphenyl]-N'(2-chlorophenyl) urea;

N-(2-bromophenyl)-N'[4-chloro-2-hydroxy-3-[N"-(2-hydroxyethyl)aminosulfonyl] urea;

N-(2,3-dichlorophenyl)-N'-[4-chloro-2-hydroxy-3-[N"-(2-hydroxyethyl)aminosulfonyl] urea;

N-(2-bromophenyl)-N'[3-[N"-[[(2-bromophenylamino)carboxyl]ethyl]aminosulfonyl]-4-chloro-2-hydroxyphenyl] urea;

N-[3-[N"-(2-benzyloxyethyl)aminosulfonyl]-4-chloro-2-hydroxyphenyl]-N'-(2 bromophenyl) urea;

N-[2-Hydroxy-3-(N"-cyclopropylmethylaminosulfonyl)-4-chlorophenyl]-N'-(2,3-dichlorophenyl) urea;

N -[2-Hydroxy-3-(N"-cyclopropylmethylaminosulfonyl)-4-chlorophenyl]-N'-(2 chlorophenyl) urea;

N-[2-Hydroxy-3-(N"-cyclopropylmethylaminosulfonyl)-4-chlorophenyl]-N'(2 bromophenyl) urea;

N-[2-Hydroxy-3-(N"-methoxy-N"-methylaminosulfonyl)-4-chlorophenyl]-N'-(2-bromophenyl) urea;

N-[2-Hydroxy-3-(N"-methoxy-N"-methylaminosulfonyl)-4-chlorophenyl]-N'-(2 chlorophenyl) urea;

N-[2-Hydroxy-3-(N"-methoxy-N"-methylaminosulfonyl)-4-chlorophenyl]-N'(2,3 dichlorophenyl) urea;

N-[2-Hydroxy-3-(N"-pyrrolidinylsulfonyl)-4-chlorophenyl]-N'-(2,3-dichlorophenyl) urea;

N-[2-Hydroxy-3-(N"-pyrrolidinylsulfonyl)-4-chlorophenyl]-N'-(2-bromophenyl) urea;

N-[2-Hydroxy-3-(N"-pyrrolidinylsulfonyl)-4-chlorophenyl]-N'-(2-chlorophenyl) urea;

N-(2-bromophenyl)-N'-[4-chloro-2-hydroxy-3-[(4-pyridinylaminosulfonyl]phenyl] urea;

N-[4-chloro-2-hydroxy-3-[(4-pyridinylaminosulfonyl]phenyl]-N'-(2,3-dichlorophenyl) urea;

N-(2-bromophenyl)-N'-[4-chloro-2-hydroxy-3-[[[2-(tetrahydro-2-furanyl)methyl]aminosulfonyl]phenyl] urea;

N-[4-chloro-2-hydroxy-3-[[[2-(tetrahydro-2-furanyl)methyl]aminosulfonyl]phenyl]-N'-(2,3-dichlorophenyl) urea;

N-(2-bromophenyl)-N'- [4-chloro-2-hydroxy-3-[[[(2R)-(tetrahydro-2-furanyl)methyl]aminosulfonyl]phenyl] urea; and N-[4-chloro-2-hydroxy-3-[[[(2R)-(tetrahydro-2-furanyl)methyl]aminosulfonyl]phenyl]-N'-(2,3-dichlorophenyl) urea;

N-(2-bromophenyl)-N'-[4-chloro-2-hydroxy-3-[[[(2S)-(tetrahydro-2-furanyl)methyl]aminosulfonyl]phenyl] urea;

N-[4-chloro-2-hydroxy-3-[[[(2S)-(tetrahydro-2-furanyl)methyl]aminosulfonyl]phenyl]-N'-(2,3-dichlorophenyl) urea;

N-(2-bromophenyl)-N'[4-chloro-2-hydroxy-3-(N"-cyclopentylaminosulfonyl)phenyl]urea N-[4-chloro-2-hydroxy-3-(N"-cyclopentylaminosulfonyl)phenyl]-N'-(2,3-dichlorophenyl) urea, and N-(2-chlorophenyl)-N'-4-chloro-2-hydroxy-3-(N"-cyclopentylaminosulfonyl)phenyl]urea N-(2-bromophenyl)-N'[4-chloro-2-hydroxy-3-(N"-isoxazolidinylaminosulfonyl) phenyl]urea N-[4-chloro-2-hydroxy-3-(N"-isoxazolidinylaminosulfonyl)phenyl]-N'-(2,3-dichlorophenyl)urea N-(2-chlorophenyl)-N'-[4-chloro-2-hydroxy-3-(N"-isoxazolidinylaminosulfonyl) phenyl]urea N-( 2-bromophenyl)-N'-[4-chloro-2-hydroxy-3-(N"-tetrahydroisoxazylaminosulfonyl) phenyl]urea N-[4-chloro-2-hydroxy-3-(N"-tetrahydroisoxazylaminosulfonyl)phenyl]-N'-(2,3-dichlorophenyl)urea N-(2-chlorophenyl)-N'[4-chloro-2-hydroxy-3-N"-(tetrahydroisoxazylaminosulfonyl) phenyl]urea N-(2-bromophenyl)-N[4-chloro-2-hydroxy-3-[(2-isopropoxyethyl)aminosulfonyl]phenyl] urea N-[4-chloro-2-hydroxy-3-[(2-isopropoxyethyl) aminosulfonylphenyl]-N'-(2,3-dichlorophenyl) urea N-[4-chloro-2-hydroxy-3-[(2-isopropoxyethyl) aminosulfonylphenyl]-N'-(2-chlorophenyl) urea N-(2-bromophenyl)-N'-[4-chloro-2-hydroxy-3-[(2-ethoxyethyl)aminosulfonyl]phenyl] urea N-[4-chloro-2-hydroxy-3-[(2-ethoxyethyl) aminosulfonyl]phenyl]-N'-(2,3-dichlorophenyl) urea N-[4-chloro-2-hydroxy-3-[(2-ethoxyethyl) aminosulfonyl]phenyl]-N'-(2chlorophenyl) urea N-(2-bromophenyl)-N'-[4-chloro-2-hydroxy-3-[(2-methoxycarbonyl)azetidin-1yl]sulfonylphenyl] urea N-[4-chloro-2-hydroxy-3-[(2-methoxycarbonyl)azetidin-1-yl]sulfonylphenyl]-N'-(2,3-dichlorophenyl) urea N-[4-chloro-2-hydroxy-3-[(2-carboxy)-azetidin-1-yl]sulfonylphenyl]-N'-(2,3-dichlorophenyl) urea N-(2-bromophenyl)-N'-[4-chloro-2-hydroxy-3-[N"-[3-(4-morpholinyl)propyl]aminosulfonyl]phenyl] urea hydrochloride N-[4-chloro-2-hydroxy-3-[N"-[3-(4-morpholinyl)propyl)-aminosulfonyl]phenyl]-N'-(2,3-dichlorophenyl) urea hydrochloride and N-[4-chloro-2-hydroxy-3-[N"-[3-(4-morpholinyl)propyl]aminosulfonyl]phenyl]-N'-(2-chlorophenyl) urea hydrochloride N-(2-bromophenyl)-N'-[4-chloro-2-hydroxy-3-[S-(–)-(2-methoxymethyl)pyrrolidin-1-yl]sulfonylphenyl] urea N-(2-bromophenyl)-N'-[4-chloro-2-hydroxy-3-[S-(–)-(2-hydroxymethyl)pyrrolidin-1-yl]sulfonylphenyl] urea N-[4-chloro-2-hydroxy-3-[S-(–)-(2-methoxymethyl)pyrrolidin-1-yl]sulfonylphenyl]-N'-(2,3-dichlorophenyl) urea N-[4-chloro-2-hydroxy-3-[S-(–)-(2-hydroxymethyl)-pyrrolidin-1-ylsulfonyl]phenyl]-N'-(2,3-dichlorophenyl) urea N-[4-chloro-2-hydroxy-3-[S-(–)-(2-methoxymethyl)-pyrrolidin-1-yl]sulfonylphenyl]-N'-(2-chlorophenyl) urea N-[4-chloro-2-hydroxy-3-[S-(–)-(2-hydroxymethyl)-pyrrolidin-1-yl]sulfonylphenyl]-N'-(2-chlorophenyl) urea N-(2-bromophenyl)-N'-[4-chloro-2-hydroxy-3-[S-(2-methoxycarbonyl)pyrrolidin-1-yl]sulfonylphenyl] urea N-(2-bromophenyl)-N'-[4-chloro-2-hydroxy-3-[S-(2-carboxy)pyrrolidin-1 -yl]sulfonylphenyl] urea N-(2-bromophenyl)-N'[3-[N"-(tert-butyl)aminosulfonyl] 4-chloro-2-hydroxyphenyl] urea N-[3-[N"-(tert-butyl)aminosulfonyl]4-chloro-2-hydroxyphenyl]-N'-(2,3-dichlorophenyl) urea and N-[3-[N"-(tert-butyl)aminosulfonyl]-4-chloro-2-hydroxyphenyl]-N'-(2-chlorophenyl) urea N-[3-[N"-[5-(tert-butoxycarbonylamino)-5-carboxypentyl]aminosulfonyl]4-chloro-2-hydroxyphenyl]-N'-(2-chlorophenyl) urea N-[3-[N"-(5-amino-5-carboxypentyl)aminosulfonyl]4-chloro-2-hydroxyphenyl]-N'-(2-chlorophenyl) urea hydrochloride N-[3-[N"-(5-amino-5-carboxypentyl)aminosulfonyl]-4-chloro-2-hydroxyphenyl]-N'-(2,3-dichlorophenyl) urea hydrochloride N-[3-[N"-(5-amino-5-carboxypentyl)aminosulfonyl]-4-chloro-2-hydroxyphenyl]-N'-(2-bromophenyl) urea hydrochloride N-[4-chloro-3-(1,1-dioxidothiomorpholinosulfonyl)-2-hydroxyphenyl]-N'-(2,3-dichlorophenyl) urea N-(2-bromophenyl)-N'[4-chloro-3-(1,1-dioxidothiomorpholinosulfonyl)-2-hydroxyphenyl] urea N-[4-chloro-3-(1,1-dioxidothiomorpholinosulfonyl)-2-hydroxyphenyl]-N'-(2-chlorophenyl) urea N-3-[N"-[2-(tert-butoxycarbonylamino)ethyl]aminosulfonyl]-4-chloro-2-hydroxyphenyl]-N'-(2,3-dichlorophenyl) urea N-[3-[N"-(2-aminoethyl)aminosulfonyl]-4-chloro-2-hydroxyphenyl]-N'-(2,3-dichlorophenyl) urea trifluoroacetate N-[3-[N"-[2-(tert-butoxycarbonylamino)ethyl]aminosulfonyl]-4-chloro-2-hydroxyphenyl]-N'-(2-chlorophenyl) urea N-[3-[N"-(2-aminoethyl)aminosulfonyl]-4-chloro-2-hydroxyphenyl]-N'-(2-chlorophenyl) urea trifluoroacetate N-[4-chloro-2-hydroxy-3-(N",N"-dimethylaminosulfonyl)phenyl]-N'-(2-chlorophenyl) urea.

N-[4-chloro-2-hydroxy-3-(aminosulfonyl)phenyl]-N'(2-bromo-3-fluorophenyl) urea

N-[4-chloro-2-hydroxy-3-(aminosulfonyl)phenyl]-N'(2-chloro-3-fluorophenyl) urea

N-(2-bromophenyl)-N'-[4-chloro-3-[(1-ethyl-pyrrolidin-2-yl)methylaminosulfonyl]-2-hydroxyphenyl] urea hydrochloride N-[4-chloro-3-[(1-ethyl-pyrrolidin-2-yl)methylaminosulfonyl]-2-hydroxyphenyl]N'-(2,3-dichlorophenyl) urea hydrochloride N-[4-chloro-3-[(1-ethyl-pyrrolidin-2-yl)methylaminosulfonyl]-2-hydroxyphenyl]-N'-(2-chlorophenyl) urea hydrochloride or a pharmaceutically acceptable salt thereof.

METHODS OF PREPARATION

The compounds of Formulas (I) to (VII) may be obtained by applying synthetic procedures, some of which are illustrated in the Schemes below. The synthesis provided for in these Schemes is applicable for the producing compounds of Formulas (I) to (VII), having a variety of different R, $R_1$, and Z groups which are reacted, employing optional substituents which are suitably protected, to achieve compatibility with the reactions outlined herein. Subsequent deprotection, in those cases, then affords compounds of the nature generally disclosed. Once the urea nucleus has been established, further compounds of these formulas may be prepared by applying standard techniques for functional group interconversion, well known in the art.

Scheme 1

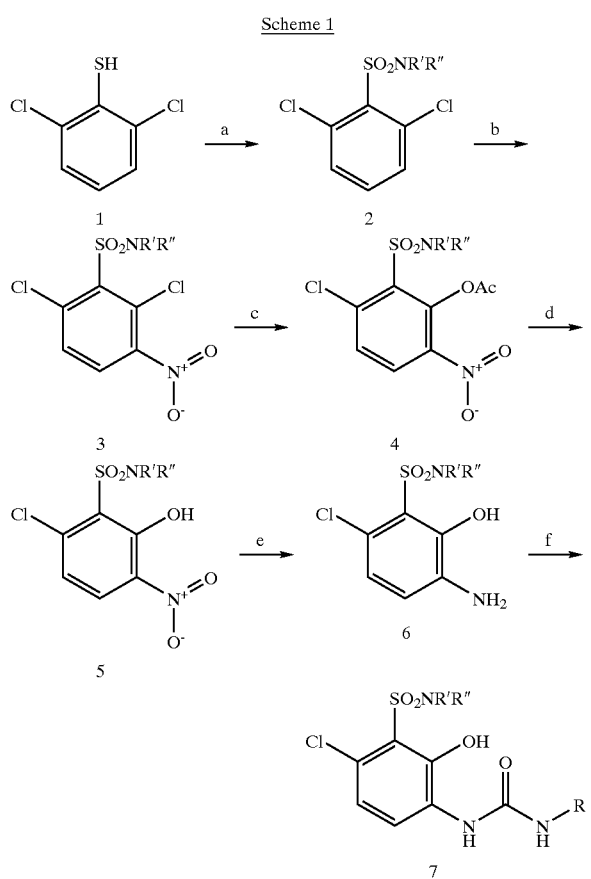

a)i)NCS, AcOH, H$_2$O, ii NR'R"H, pyr b)H$_2$SO$_4$, HNO$_3$ c)NaOAc, 18-crown-6 d)H$_2$SO$_4$, MeOH e) Pd/C, H$_2$ f)RCNO, DMF The desired 4-chloro-N-(3-sulfonamido-2-hydroxyphenyl)-N"-phenyl urea can be synthesized from the commercially available 2,6-dichlorothiophenol using the procedure elaborated in Scheme 1. The thiol can be oxidized to the corresponding sulfonyl halide using a halogenating agent, such as NCS, NBS, Cl$_2$ or B.C.$_{.2}$, in the presence of a protic solvent, such as water, acetic acid, or an alcohol or combination thereof. The yield may be increased if a buffering agent, such as sodium or potassium acetate is included in the reaction mixture, and the reaction is conducted at or below room temperature. The corresponding sulfonyl halide can then be condensed with an amine in presence of a base such as pyridine, triethyl amine, potassium carbonate or sodium hydride to form the analogous sulfonamide 2-scheme 1. The dichlorosulfonamide 2-scheme 1 can be nitrated using strong nitrating conditions such as nitric acid in sulfuric acid to form the aromatic nitro compound 3-scheme 1. The chlorine ortho to the nitro group can be selectively hydrolyzed using acetate salt such as sodium acetate in the presence of a crown ether, such as 18-crown-6, to form the acetate 4-scheme 1. The acetate group can be hydrolyzed under acidic conditions in an alcohol solvent such as methanol or ethanol with a catalytic amount of acid to form the phenol 5-scheme 1. The nitro can be reduced by conditions well known in the art such as hydrogen and palladium on carbon, tin chloride in methanol, zinc in acetic acid or thiol to form the corresponding aniline 5-scheme 1. The aniline can then be coupled with a commercially available isocyanate or thioisocyanate to form the desired urea or thio urea. Alternatively the desired isocyanates can be made by condensing the amine with triphosgene in the presence of base (such as potassium carbonate) or by reacting the carboxylic acid with diphenyl phosphorazide in the presence of a base (such as triethyl amine).

Scheme 2

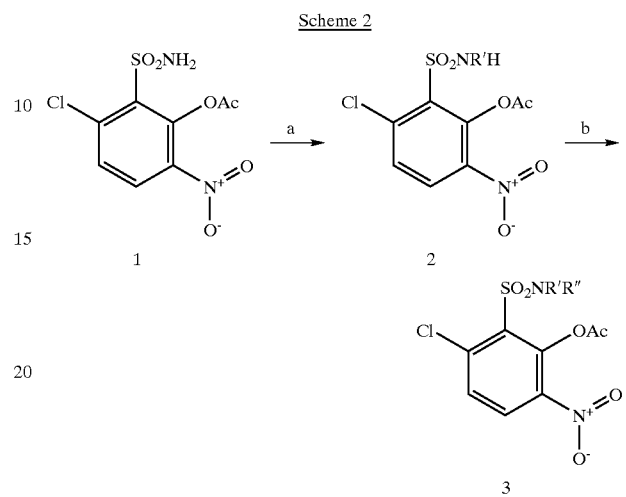

a)NaH, R'X b)NaH R"X

If the sulfonamide 1-scheme 2 (3-scheme 1) is unfunctionalized R'=R"=H then it can be functionalized as required herein, by alkylation. The sulfonamide is deprotonated using a base such as sodium hydride and then alkylated using an alkyl halide such as benzyl bromide or methyl iodide form 2-scheme 2. The sulfonamide can then be alkylated a second time using sodium hydride and another alkyl halide to form 3-scheme 2. This compound can then be converted to the desired urea using the process elaborated in scheme 1.

Scheme 3

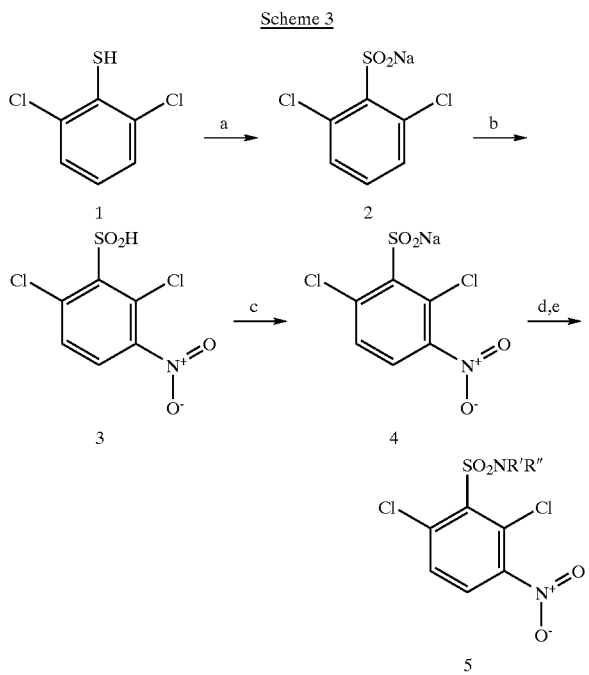

a)i)NCS, AcOH, H$_2$O ii)NaOH MeOH b)H$_2$SO$_4$,HNO$_3$ c)NaOH MeOH d) PCl$_5$, POCl$_3$ e)NHR'R", Et$_3$N

An alternative route to 5-scheme 3 (3-scheme 1) is outlined above, in scheme 3 wherein the commercially available 2,6-dichloro thiol can be oxidized to the sulfonyl halide using a halogenating agent such as NCS, NBS, chlorine or bromine in the presence of a protic solvent such as alcohol, acetic acid or water. The sulfonyl halide can be hydrolyzed by using a metal hydroxide such as sodium or potassium hydroxide to form the corresponding sulfonic acid salt. The sulfonic acid salt can then be nitrated under nitration conditions such as nitric acid in a solvent of strong acid such as sulfuric acid to form the nitro phenyl sulfonic acid 3-scheme 3. The sulfonic acid 3-scheme 3 can be converted to the sulfonamide 5-scheme 3 using a three step procedure involving the formation of the metal salt using a base such as sodium hydroxide, sodium hydride or sodium carbonate to form 4-scheme 3. The sulfonic acid salt is then converted to the sulfonyl chloride using $PCl_5$ with $POCl_3$ as a solvent. The sulfonyl chloride can then be converted to the corresponding sulfonamide using the desired amine HNR'R" in triethyl amine at temperatures ranging from −78° C. to 60° C. to form the corresponding sulfonamide 5-scheme 3 (3-scheme 1). The sulfonamide 5-scheme 3 can be further elaborated by the methods contained in scheme 1. This method is not limited to the 2,6-dichlorophenyl thiol it can also be applied to the 2,6-difluorophenyl thiol, 2,6-dibromophenyl thiol and the 2,6-diiodophenyl thiol. The halogens in these compounds can be converted to the corresponding cyano, amino, thiol, or alkoxy compounds by nucleophilic displacement reactions using nucleophiles such as alkyl thiolates, alkoxides, amine and cyanides. The halogens can also be further functionalized by palladium coupling and carbonylation reactions, well known in the art, to form the corresponding amido, carbonyl, alkenyl, alkyl, phenyl and heterocyclic substituted products as required by Formula (I) to (VII).

Novel intermediates of the present invention involve compounds of formula (II), (III), (IV), (V), (VI) and (VII):

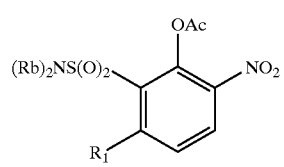

(II)

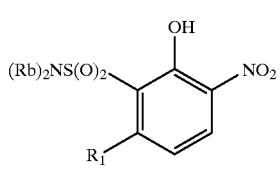

(III)

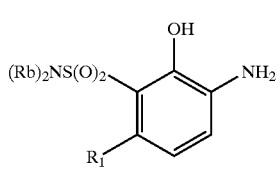

(IV)

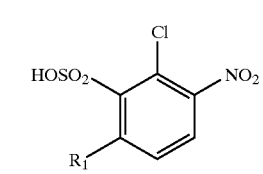

(V)

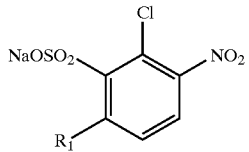

(VI)

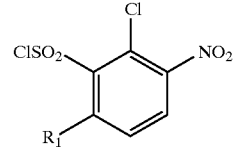

(VII)

wherein $R_1$ is not hydrogen.

Novel synthetic steps disclosed by the present invention include the conversion of a chloro compound of formula (VII) to the phenol of formula (III) using sodium acetate and 18-C-6 followed by hydrolysis with sulfuric acid and methanol and the same transformation achieved in one step using sodium hydride and water in THF.

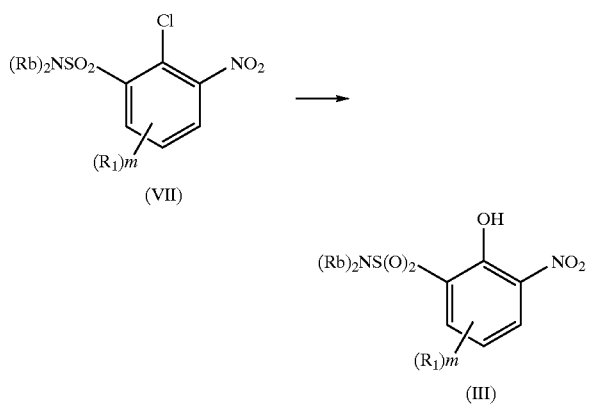

A second novel synthetic step involves the nitration of the sulfonic acid or sodium salt of formula (VIII) to the nitro compound of formula (IX) using nitric acid, in sulfuric acid.

R=H or Na

SYNTHETIC EXAMPLES

The invention will now be described by reference to the following examples, which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C). Mass spectra were performed upon a VG Zab mass spectrometer using fast atom bombardment, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant. The purification, yields and spectral characteristics for each individual compound are listed below.

Example 1

Preparation of N(4-chloro-2-hydroxy-3-aminosulfonylphenyl)-N'-(2,3-dichlorophenyl) urea sodium salt, and N-(2-bromophenyl)-N'-(4-chloro-2-hydroxy-3-aminosulfonylphenyl) urea 2,6-Dichlorobenzenesulfonyl chloride Into a mixture of 200 milliliters (hereinafter "mL") of acetic acid, water and dichloromethane (3/1/4, v/v/v), 2,6-dichlorobenzenethiol (10.0 grams (hereinafter "g"), 55.8 millimoles (hereinafter "mmol"), N-chlorosuccinimide (37.28 g, 279 mmol) and potassium acetate (2.29 g, 27.9 mmol) were added. The resulting mixture was stirred at 0° C., then warmed to room temperature overnight. The mixture was then diluted with 200 mL of dichloromethane, and washed with water (100 mL×3). The organic layer was dried ($Na_2SO_4$) and concentrated to give the desired product (11 g, 80%). $^1$H NMR ($CDCl_3$): δ 7.57 (d, 2H), 7.47 (t, 1H).

2,6-Dichlorobenzenesulfonamide

A solution of 2,6-dichlorobenzenesulfonyl chloride (10.50 g, 42.77 mmol) in 100 mL of pyridine was added dropwise to 100 mL of pyridine while anhydrous ammonia gas was bubbled through the solution. After 4 hours at 0° C., the mixture was acidified to pH>1 with 6N aq. HCl, then extracted with ethyl acetate. The combined organic layer was then dried ($Na_2SO_4$) and concentrated to give the desired product (8.69 g, 90%). EI-MS (m/z) 225.0, 227.1 (M$^-$).

2,6-Dichloro-3-nitrobenzenesulfonamide

Into a solution of 2,6-dichlorobenzenesulfonamide (7.8 g, 34.5 mmol) in 30 mL of concentrated sulfuric acid at 0°, nitric acid (1.74 mL, 41.4 mmol) was added dropwise. The mixture was stirred at 02 C., for 2 hours, then 200 mL of water was added to produce a precipitate. The resulting mixture was filtered. The white solid was collected, washed with water and dried in vacuo to give the desired product (7.17 g, 76%). $^1$H NMR (DMSO-$d_6$): δ 8.25 (s, 2H), 8.20 (d, 1H), 7.92 (d, 1H).

2-Acetyl-6-chloro-3-nitrobenzenesulfonamide

A solution of 2,6-dichloro-3-nitrobenzenesulfonamide (2.04 g, 7.5 mmol), potassium acetate (2.21 g, 22.5 mmol) and 18-crown-6 (5.95 g, 22.5 mmol) in 50 mL of dimethyl sulfoxide was heated to 45° C., for 7 days. The mixture was acidified with 1N aq. HCl, and extracted with ethyl acetate. The organic layer was concentrated to give the crude material. Column chromatography on silica gel, eluting with ethyl acetate/hexane/acetic acid (50/49/1, v/v/v) gave the desired product (1.67 g, 76%). EI-MS (m/z) 293.1, 295.1 (M$^-$).

6-Chloro-2-hydroxy-3-nitrobenzenesulfonamide

A solution of 2-acetyl6-chloro-3-nitrobenzenesulfonamide (1.72 g, 5.83 mmol), chlorotrimethylsilane (2 mL) and fuming sulfuric acid (0.5 mL) in methanol was heated to reflux for 20 hours. The solvent was evaporated. The residue was diluted with ethyl acetate and washed with water. The organic layer was then dried ($Na_2SO_4$) and concentrated to give the desired product (1.0 g, 68%). EI-MS (m/z) 251.1, 253.2 (M$^-$).

3-Amino-6-chloro-2-hydroxybenzenesulfonamide

To a solution of 6-chloro-2-hydroxy-3-nitrobenzenesulfonamide (1.1 g, 4.36 mmol) in ethyl acetate, was added 10% Pd/C (500 mg). The mixture was flushed with argon, and then stirred under a hydrogen atmosphere at balloon pressure for 4 hours at room temperature. The mixture was filtered through celite and the celite was washed with methanol. The solvent was evaporated to give the desired product (0.9g, 93%). EI-MS (m/z) 221.1, 223.1 (M$^-$).

N-(4-Chloro-2-hydroxy-3-aminosulfonylphenyl)-N'-(2,3-dichlorophenyl) urea

A solution of 3-amino-6-chloro-2-hydroxybenzenesulfonamide (0.88 g, 3.9 mmol) and 2,3-dichlorophenylisocyanate (0.62 mL, 4.6 mmol) in 5 mL of N,N-dimethyl-formamide was stirred at room temperature for 20 hours. The mixture was diluted with ethyl acetate and washed with water to give the crude material. Purification by column chromatography on silica gel, eluting with ethyl acetate/hexane (30/70 to 50/50, v/v), followed by recrystallization from dichloromethane and hexane, gave the desired product (1.18 g, 74%). mp 241–242° C.

N-(2-Bromophenyl)-N'-(4-chloro-2-hydroxy-3-aminosulfonylphenyl) urea

A solution of 3-amino-6-chloro-2-hydroxybenzenesulfonamide (65 mg, 0.29 mmol) and 2,3-dichlorophenylisocyanate (45 μL, 0.36 mmol) in 2 mL of N,N-dimethyl-formamide was stirred at room temperature for 20 hours. The mixture was diluted with ethyl acetate and washed with water to give the crude material. Purification by column chromatography on silica gel, eluting with ethyl acetate/hexane (30/70 to 40/60, v/v), gave the desired product (50 mg, 41%). EI-MS (m/z) 418.2, 420.2, 422.2 (M$^-$).

N-(4-chloro-2-hydroxy-3-aminosulfonylphenyl)-N'-(2,3-dichlorophenyl) urea sodium salt To a solution of N-(4-chloro-2-hydroxy-3-aminosulfonylphenyl)-N'-(2,3-dichlorophenyl) urea (1.47g, 59 mmol) in 150 mL of acetone was added 2.46 mL of aq. NaOH solution (1.45 M). The mixture was stirred for 16 hours at room temperature and the solvent was evaporated. The residue was recrystallized from acetone and dichloromethane to give the desired product (1.41 g, 91%). $^1$H NMR (DMSO-$d_6$): δ 9.27 (s, 2H), 8.01 (m, 3H), 7.77 (d, 1H), 7.26 (m, 2H), 6.05 (d, 1H)

Examples 2 & 3

Preparation of N-[3-(N"-benzylaminosulfonyl)-4-chloro-2-hydroxyphenyl]-N'-(2,3-dichlorophenyl) urea and N-[3-(N"-benzylaminosulfonyl)-4-chloro-2-hydroxyphenyl]-N'-(2-bromophenyl) urea N-Benzyl-2-acetyl-6-chloro-3-nitro-benzenesulfonamide A mixture of 2-acetyl-6-chloro-3-nitrobenzenesulfonamide (500 mg, 1.69 mmol), potassium carbonate (469 mg, 3.39 mmnol) and benzyl bromide (0.24 mL, 2.0 mmol) in 20 mL of N,N-dimethylformamide was heated to 75° C for 24 hours. The mixture was acidified with 1 N aq. HCl, then extracted with ethyl acetate. The solvent was concentrated to give the crude material. Column chromatography on silica gel, eluting with ethyl acetate/hexane/acetic acid (50/49/1, v/v/v), gave the desired product (274 mg, 42%). EI-MS (m/z) 383.3, 385.3 (M$^-$).

N-Benzyl-6-chloro-2-hydroxy-3-nitrobenzenesulfonamide

A solution of N-benzyl-2-acetyl-6-chloro-3-nitrobenzenesulfonamide (225 mg, 0.59 mmol), 0.1 mL of chlorotrimethylsilane and 2 drops of fuming sulfuric acid in ethanol was heated to reflux for 20 hours. The solvent was evaporated. The residue was diluted with ethyl acetate and washed with water. The organic layer was then dried ($Na_2SO_4$) and concentrated to give the desired product (189 mg, 94%). $^1$H NMR (DMSO-$d_6$): δ 7.92 (d, 1H), 7.18 (m, 5H), 6.93 (d, 1H), 4.15 (s, 2H).

N-Benzyl-3-amino-6-chloro-2-hydroxybenzenesulfonamide

To a solution of N-benzyl-6-chloro-2-hydroxy-3-nitrobenzenesulfonamide (180 mg, 0.52 mmol) in ethyl acetate, was added 10% Pd/C (70 mg). The mixture was flushed with argon, then stirred under a hydrogen atmosphere at balloon pressure for 1 hour at room temperature.

The mixture was filtered through celite and the celite was washed with methanol. The solvent was evaporated to give the desired product (140 mg, 85%). $^1$H NMR (DMSO-$d_6$): δ 8.73 (t, 1H), 7.24 (m, 5H), 6.78 (d, 1H), 4.09 (d, 2H).

N-[3-(N"-Benzylaminosulfonyl)-4-chloro-2-hydroxyphenyl]-N'(2,3-dichlorophenyl) urea A solution of N-benzyl-3-amino-6-chloro-2-hydroxybenzenesulfonamide (54 mg, 0.17 mmol) and 2,3-dichlorophenylisocyanate (34 μL, 0.26 mmol) in 2 mL of N,N-dimethylformamide was stirred at room temperature for 20 hours. The mixture was diluted with ethyl acetate and washed with water to give the crude material. Purification by column chromatography on silica gel, eluting with ethyl acetate/hexane (60/40, v/v), gave the desired product (10 mg, 12%). EI-MS (m/z) 498.2, 500.1, 502.1 (M$^-$).

N-[3-(N"-Benzylaminosulfonyl)-4-chloro-2-hydroxyphenyl]-N'(2-bromophenyl) urea

A solution of N-benzyl-3-amino-6-chloro-2-hydroxybenzenesulfonamide (80 mg, 0.26 mmol) and 2-bromophenylisocyanate (47 μL, 0.38 mmol) in 2 mL of N,N-dimethylformamide was stirred at room temperature for 20 hours. The mixture was diluted with ethyl acetate and washed with water to give the crude material. Purification by column chromatography on silica gel, eluting with ethyl acetate/hexane (30/70 to 70/30, v/v), gave the desired product (80 mg, 61%). EI-MS (m/z) 508.1, 510.2, 512.2 (M$^-$).

Examples 4 & 5

Preparation of N-[4chloro-3-(N",N"-dimethylaminosulfonyl)-2-hdroxyphenyl]-N'-(2,3-dichlorophenyl) urea and N-(2-bromophenyl)-N'--8 4-chloro-3-(N",N"-dimethylaminosulfonyl)-2-hydroxyphenyl] urea N,N-dimethyl-6-chloro-2-hydroxy-3-nitrobenzenesulfonamide To a mixture of 2-acetyl-6-chloro-3-nitrobenzenesulfonamide (300 mg, 1.02 mmol) and sodium hydride (122 mg, 3.06 mmol) in 10 mL of N,N-dimethylformamide, was added iodomethane (0.64 mL, 10.2 mmol). The mixture was stirred at room temperature for 20 hours. The resulting mixture was acidified with 1 N aq. HCl, then extracted with ethyl acetate. The solvent was concentrated to give the crude material. Column chromatography on silica gel, eluting with ethyl acetate/hexane/acetic acid (50/49/1, v/v/v), gave the desired product (140 mg, 49%). $^1$H NMR (DMSO-$d_6$): δ 8.05 (d, 1H), 7.03 (d, 1H), 2.87 (s, 6H).

N,N-Dimethyl-3-amino-6-chloro-2-hydroxybenzenesulfonamide.

To a solution of N,N-dimethyl-6-chloro-2-hydroxy-3-nitrobenzenesulfonamide (140 mg, 0.50 mmol) in ethyl acetate, was added 10% Pd/C (50 mg). The mixture was flushed with hydrogen, then stirred under a hydrogen atmosphere at balloon pressure for 1.5 hours at room temperature. The mixture was filtered through celite and the celite was washed with methanol. The solvent was evaporated to give the desired product (100 mg, 80%). $^1$H NMR (DMSO-$d_6$): δ 6.87 (d, 1H), 6.80 (d, 1H), 2.82 (s, 6H).

N-[4-Chloro-3-(N",N"-dimethylaminosulfonyl)-2-hydroxyphenyl]-N'-(2,3-dichlorophenyl) urea.

A solution of N,N-dimethyl-3-amino-6-chloro-2-hydroxybenzenesulfonamide (80 mg, 0.32 mmol) and 2,3-dichlorophenylisocyanate (50 μL, 0.38 mmol) in 2 mL of N,N-dimethylformamide was stirred at room temperature for 20 hours. The mixture was diluted with ethyl acetate and washed with water to give the crude material. Purification by column chromatography on silica gel, eluting with ethyl acetate/hexane (20/80, v/v), followed by recrystallization from ethyl acetate and hexane, gave the desired product (63 mg, 45%). $^1$H NMR (DMSO-$d_6$): δ 10.51 (s, 1H), 9.34 (s, 1H), 9.27 (s, 1H), 8.29 (d, 1H), 7.32 (m, 2H), 7.16 (d, 1H), 2.87 (s, 6H).

N-(2-Bromophenyl)-N'-[4-chloro-3-(N",N"-dimethylaminosulfonyl)-2-hydroxyphenyl] urea.

A solution of N,N-dimethyl-3-amino-6-chloro-2-hydroxybenzenesulfonamide (80 mg, 0.32 mmol) and 2-bromophenylisocyanate (47 μL, 0.38 mmol) in 2 mL of N,N-dimethylformamide was stirred at room temperature for 20 hours. The mixture was diluted with ethyl acetate and washed with water to give the crude material. Purification by column chromatography on silica gel, eluting with ethyl acetate/hexane (20/80, v/v), followed by recrystallization from ethyl acetate and hexane, gave the desired product (88 mg, 62%). EI-MS (m/z) 446.2, 448.3, 450.3 (M$^-$).

Examples 6 & 7

Preparation of N-[4-chloro-2-hydroxy-3-(N"-methylaminosulfonyl)phenyl]-N'-(2,3-dichlorophenyl) urea and N-(2-bromophenyl)-N'-[4-chloro-2-hydroxy-3-(N"-methylaminosulfonyl) phenyl] urea N-Methyl-2-acetyl-6-chloro-3-nitrobenzenesulfonamide.

To a mixture of 2-acetyl-6-chloro-3-nitrobenzenesulfonamide (300 mg, 1.02 mmol) and sodium hydride (53 mg, 1.32 mmol) in 10 mL of N,N-dimethylformamide, iodomethane (70 μL, 1.12 mmol) was added. The mixture was stirred at room temperature for 66 hours. The mixture was acidified with 1 N aq. HCl, then extracted with ethyl acetate. The solvent was concentrated to give the crude material. Column chromatography on silica gel, eluting with ethyl acetate/hexane/acetic acid (50/49/1, v/v/v), gave the desired product (185 mg, 59%). EI-MS (m/z) 307.3, 309.3 (M$^-$).

N-Methyl-6-chloro-2-hydroxy-3-nitrobenzenesulfonamide.

A solution of N-methyl-2-acetyl-6-chloro-3-nitrobenzenesulfonamide (170 mg, 0.55 mmol), 0.5 mL of chlorotrimethylsilane and 3 drops of fuming sulfuric acid in ethanol was heated to reflux for 20 hours. The solvent was evaporated. The residue was diluted with ethyl acetate and washed with water. The organic layer was then dried ($Na_2SO_4$) and concentrated to give the desired product (160 mg, >100%). EI-MS (m/z) 265.2, 267.2 (M$^-$).

N-Methyl-3-amino-6-chloro-2-hydroxybenzenesulfonamide.

To a solution of N-methyl-6-chloro-2-hydroxy-3-nitrobenzenesulfonamide (140 mg, 0.53 mmol) in ethyl acetate, was added 10% Pd/C (60 mg). The mixture was flushed with argon, then stirred under a hydrogen atmosphere at balloon pressure for 1.5 hours at room temperature. The mixture was filtered through celite and the celite was washed with methanol. The solvent was evaporated to give the desired product (160 mg, >100%). $^1$H NMR (DMSO-$d_6$): δ 7.95 (bs, 1H), 6.85 (d, 1H), 6.79 (d, 1H), 2.48 (d, 3H).

N-[4-chloro-2-hydroxy-3-(N"-methylaminosulfonyl) phenyl]-N'-(2,3-dichlorophenyl) urea A solution of N-methyl-3-amino-6-chloro-2-hydroxybenzenesulfonamide (70 mg, 0.29 mmol) and 2,3-dichlorophenylisocyanate (57 μL, 0.44 mmol) in 2 mL of N,N-dimethylformamide was stirred at room temperature for 66 hours. The mixture was diluted with ethyl acetate and washed with water to give the crude material. Purification by column chromatography on silica gel, eluting with ethyl acetate/hexane (30/70, v/v), gave the desired product (60 mg, 49%, three steps). EI-MS (m/z) 422.3, 424.3, 426.3 (M$^-$).

N'-(2-bromophenyl)-N'-4-chloro-2-hydroxy-3-(N"-methylaminosulfonyl)phenyl] urea

A solution of N-methyl-3-amino-6-chloro-2-hydroxybenzenesulfonamide (70 mg, 0.29 mmol) and 2-bromophenylisocynate (55 µL, 0.44 mmol) in 2 mL of N,N-dimethylformamide was stirred at room temperature for 66 hours. The mixture was diluted with ethyl acetate and washed with water to give the crude material. Purification by column chromatography on silica gel, eluting with ethyl acetate/hexane (30/70, v/v), gave the desired product (85 mg, 67%, three steps). EI-MS (m/z) 432.2, 434.2, 436.3 (M⁻).

Example 8, 9, 10 & 11

Preparation of N-[4-chloro-2-hydroxy-3-[N"-[2-(methoxycarbonyl)-methyl]aminosulfonyl]phenyl]-N'-(2,3-dichlorophenyl) urea, N[3-[N"-(2-carboxymethyl)aminosulfonyl]-4-chloro-2-hydroxyphenyl-N'-(2,3-dichlorophenyl) urea.

N-(2-bromophenyl )-N'-[4-chloro-2-hydroxy-3-[N"-[2-(methoxycarbonyl)methyl]-aminosulfonyl]phenyl] urea, and N-(2-bromophenyl)-N'-[3-[N"-(2-carboxymethyl)aminosulfonyl]-4-chloro-2-hydroxyphenyl] urea N-[2-(methoxycarbonyl)methyl]-2-acetyl-6-chloro-3-nitrobenzenesulfonamide To a mixture of 2-acetyl-6-chloro-3-nitrobenzenesulfonamide (300 mg, 1.02 mmol) and sodium hydride (81 mg, 2.02 mmol) in 10 mL of N,N-dimethylformamide, was added methyl bromoacetate (106 µL, 1.12 mmol). The mixture was heated to 80° C. for 20 hours, followed by adding more sodium hydride (81 mg, 2.02 mmol) and stirring at room temperature for 66 hours. The resulting mixture was acidified with 1 N aq. HCl, then extracted with ethyl acetate. The solvent was concentrated to give the crude material. Column chromatography on silica gel, eluting with ethyl acetate/hexane/acetic acid (60/39/1, v/v/v), gave the desired product (350 mg, 95%). $^1$H NMR (DMSO-d$_6$): δ 7.76 (d, 1H), 6.12 (d, 1H), 4.57 (s, 2H), 3.66 (s, 3H), 2.22 (s, 3H).

N-[2-(methoxycarbonyl)methyl]-6-chloro-2-hydroxy-3-nitrobenzenesulfonamide

A solution of N-[2-(methoxycarbonyl)methyl]-2-acetyl-6-chloro-3-nitrobenzenesulfonamide (350 mg, 0.95 mmol), 0.5 mL of chlorotrimethylsilane and 3 drops of fuming sulfuric acid in methanol was heated to reflux for 20 hours. The solvent was evaporated. The residue was diluted with ethyl acetate and washed with water. The organic layer was then dried (Na$_2$SO$_4$) and concentrated to give the desired product (182 mg, 59%). EI-MS (m/z) 323.0, 325.0 (M$^{31}$ ).

N-[2-(methoxycarbonyl)methyl]-3-amino-6-chloro-2-hydroxybenzenesulfonamide

To a solution of N-[2-(methoxycarbonyl)methyl]-6-chloro-2-hydroxy-3-nitrobenzenesulfonamide (170 mg, 0.52 mmol) in ethyl acetate, was added 10% Pd/C (80 mg). The mixture was flushed with hydrogen, then stirred under a hydrogen atmosphere at balloon pressure for 3 hours at room temperature. The mixture was filtered through celite and the celite was washed with methanol. The solvent was evaporated to give a mixture of the desired product and impurity. The mixture was used for next step without further purification. $^1$H NMR (DMSO-d$_6$): 8δ 8.68 (m, 1H), 6.85 (d, 1H), 6.79 (d, 1H), 3.83 (s, 2H), 3.53 (s, 3H).

N-[4-chloro-2-hydroxy-3-[N"-[2-(methoxycarbonyl) methyl]aminosulfonyl]phenyl]-N'(2,3- dichlorophenyl) urea A solution of N-[2-(methoxycarbonyl)methyl]-3-amino-6-chloro-2-hydroxybenzene-sulfonamide (0.26 mmol) and 2,3-dichlorophenylisocyanate (41 µL, 0.31 mmol) in 2 mL of N,N-dimethylformamide was stirred at room temperature for 20 hours. The mixture was diluted with ethyl acetate and washed with water to give the crude material. Purification by column chromatography on silica gel, eluting with ethyl acetate/hexane (40/60, v/v), gave the desired product (35 mg, 28% for two steps). EI-MS (m/z) 479.9, 482.0, 483.9 (M⁻).

N-[3-[N"-(2-carboxymethyl)aminosulfonyl]-4-chloro-2-hydroxyphenyl]-N'-(2,3-dichlorophenyl) urea A mixture of N-[4-chloro-2-hydroxy-3-[N"-[2-(methoxycarbonyl)methyl]-aminosulfonyl]phenyl]-N'-(2,3-dichlorophenyl) urea (20 mg, 0.041 mmol) and lithium hydroxide monohydrate (40 mg, 0.95 mmol) in 5 mL of methanol (95%) was stirred at room temperature for 20 hours. The mixture was acidified with 1 N aq. HCl to produce white precipitate. The resulting mixture was then filtered, the white solid was collected and dried in vacuo to give the desired product (15 mg, 78%). EI-MS (m/z) 465.9, 467.9, 469.9 (M⁻)

N-(2-bromophenyl)-N'-[4-chloro-2-hydroxy-3-[N"-[2-(methoxycarbonyl)methyl]-aminosulfonyl]phenyl] urea A solution of N-[2-(methoxycarbonyl)methyl]-3-amino-6-chloro-2-hydroxybenzenesulfonamide (0.26 mmol) and 2-bromophenylisocyanate (38 µL, 0.31 mmol) in 2 mL of N,N-dimethylformamide was stirred at room temperature for 20 hours. The mixture was diluted with ethyl acetate and washed with water to give the crude. Purification by column chromatography on silica gel, eluting with ethyl acetate/hexane (30/70, v/v), gave the desired product (40 mg, 31% for two steps). EI-MS (m/z) 489.9, 491.9, 493.9 (M⁻).

N-(2-bromophenyl)-N'-[3-[N"-(2-carboxymethyl) aminosulfonyl]4-chloro-2-hydroxyphenyl] urea A mixture of N-(2-bromophenyl)-N'-(4-chloro-2-hydroxy-3-[N"-[2-(methoxycarbonyl)methyl] aminosulfonyl]phenyl] urea (15 mg, 0.03 mmol) and lithium hydroxide monohydrate (20 mg, 0.48 mmol) in 5 mL of methanol (95%) was stirred at room temperature for 20 hours. The mixture was acidified with 1 N aq. HCl to produce white precipitate. The resulting mixture was then filtered, the white solid was collected and dried in vacuo to give the desired product (10 mg, 70%). 476.1, 478.1, 490.1 (M⁻).

Using analogous methods to those indicated above the following additional compound have been prepared:

Example 12

N-(4-chloro-2-hydroxy-3-aminosulfonylphenyl)-N'-(2-chlorophenyl) urea

A solution of 3-amino-6-chloro-2-hydroxybenzenesulfonamide (40mg, 0.18mmol) and 2-chlorophenylisocyanate (33 mg, 0.22 mmol) in 1 mL of N,N-dimethyl-formamide was stirred at room temperature for 18 hours. The mixture was diluted with ethyl acetate and washed with water to give the crude material. Purification by column chromatography on silica gel, eluting with ethyl acetate/hexane (30/70, v/v), followed by recrystallization from acetone and hexane, gave the desired product (30 mg, 44%). EI-MS (m/z) 374.3, 376.1 (M⁻).

Example 13

Preparation of N-(4-chloro-2-hydroxy-3-aminosulfonylphenyl)-N'-phenyl urea

Following the general procedure for urea formation outlined in example 12, 3-amino-6-chloro-2-hydroxybenzenesulfonamide (40 mg, 0.18 mmol) and phenylisocyanate (32 mg, 0.27 mmol) were coupled to form the desired urea (25 mg, 41%). EI-MS (m/z) 340.3, 342.3 (M⁻).

Example 14

N-(4chloro-2-hydroxy-3-aminosulfonylphenyl)-N'-(2-phenoxyphenyl) urea

Following the general procedure for urea formation outlined in example 12, 3-amino-6-chloro-2-hydroxybenzenesulfonamide (40 mg, 0.18 mmol) and 2-phenoxyphenylisocyanate (46 mg, 0.22 mmol) were coupled to form the desired urea (41 mg, 52%). 1H NMR (DMSO-d$_4$): δ 10.69 (s, 1H), 9.25 (2, 1H), 9.11 (s, 1H), 8.18 (m, 4H), 7.41 (m, 2H), 7.04 (m, 8H), 6.84 (d, 1H).

Example 15 and 16

Preparation of N-[4-chloro-2-hydroxy-3- [N"-(2-methoxyethyl)aminosulfonyl]phenyl]-N'-(2,3-dichlorophenyl) urea sodium salt and N-(2-bromophenyl)-N'-[4-chloro-2-hydroxy-3-[N"-(2-methoxyethyl)-aminosulfonyl]phenyl] urea The following is the general procedure for sulfonamide formation N-(2-methoxyethyl)-2,6-dichloro-3-nitrobenzenesulfonamide Into a solution of 2,6-dichloro-3-nitrobenzenesulfonyl chloride (600mg, 2.06mmol) in 15 mL of dichloromethane at −78° C was added dropwise a solution of 2-methoxyethylamine (155 mg, 2.06 mmol) and triethylamine (770µL, 5.15mmol) in 10 mL of dichloromethane.

The mixture was warmed to room temperature and stirred for 16 hours. The mixture was acidified to pH>1 with 1 N aq. HCl, then extracted with ethyl acetate. The combined organic layer was then concentrated to give the crude material. Column chromatography on silica gel, eluting with ethyl acetate/hexane (30/70, v/v/), gave the desired (640mg, 94%). EI-MS (m/z) 327.1, 329.1 (M⁻).

The following is the general procedure for the hydrolysis of dichlorosulfonamide to phenol N-(2-methoxyethyl)-6-chloro-2-hydroxy-3-nitrobenzenesulfonamide A mixture of N-(2-methoxyethyl)-2,6-dichloro-3-nitrobenzenesulfonamide (490 mg, 1.49 mmol), 60% sodium hydride (179 mg, 4.47 mmol) and water (27 µL, 1.49 mmol) was heated to 35° C. while kept at argon atmosphere for 3 days. The reaction was monitored by ¹H NMR. 0.1 equivalent water was added to the mixture when the reaction was not completed. The solvent was evaporated when the reaction almost completed indicated by ¹H NMR. The residue was diluted with ethyl acetate and washed with 1 N aq. HCl. The solvent was concentrated to give the crude material. Column chromatography on silica gel, eluting with ethyl acetate/hexane/acetic acid (40/58/2, v/v/v), gave the desired product (270mg, 58%). EI-MS (m/z) 309.1, 311.1 (M⁻).

The following is the general procedure for the hydrogenation of nitro compound to aniline N-(2-methoxyethyl)-3-amino-6-chloro-2-hydroxybenzenesulfonamide To a solution of N-(2-methoxyethyl)-6-chloro-2-hydroxy-3-nitrobenzenesulfonamide (260 mg, 0.84 mmol) in ethyl acetate, was added 10% Pd/C (100 mg). The mixture was flushed with argon, and then stirred under a hydrogen atmosphere at balloon pressure for 3 hours at room temperature. The mixture was filtered through celite and the celite was washed with methanol. The solvent was evaporated to give the desired product (210 mg, 89%). EI-MS (m/z) 281.1, 283.1 (M⁻).

The following is the general procedure for urea formation N-[4-chloro-2-hydroxy-3-[N"-(2-methoxyethyl)aminosulfonyl]phenyl]-N'(2,3-dichlorophenyl) urea A solution of N-(2-methoxyethyl)-3-amino-6-chloro-2-hydroxybenzenesulfonamide (772 mg, 2.75 mmol) and 2,3-dichlorophenylisocyanate (560 mg, 3.03 mmol) in 2 mL of N,N-dimethylformamide was stirred at room temperature for 18 hours. The mixture was diluted with ethyl acetate and washed with water to give the crude material. Purification by column chromatography on silica gel, eluting with ethyl acetate/hexane (30/70, v/v), followed by recrystallization from acetone and hexane, gave the desired product (720 mg, 56%). Element Analysis Theory: C 41.00%, H 3.44%, N 8.96%, Found: C 40.77%, H 3.28%, N 8.83%.

The following is the general procedure for sodium salt formation N-[4-chloro-2-hydroxy-3-[N"-(2-methoxyethyl)aminosulfonyl]phenyl]-N'-(2,3-dichlorophenyl) urea, sodium salt To a solution of N[4-chloro-2-hydroxy-3-[N"-(2-methoxyethyl)aminosulfonyl]-phenyl]-N'-(2,3-dichlorophenyl) urea (307 mg, 0.66 mmol) in 30 mL of acetone was added 1.20 mL of aq. NaOH solution (0.54 M). The mixture was stirred for 16 hours at room temperature and the solvent was evaporated. The residue was recrystallized from acetonitrile to give the desired product (288 mg, 89%). ¹H NMR (DMSO-d$_6$): δ 9.31 (s, 1H), 9.27 (s, 1H), 8.00 (d, 1H), 7.78 (d, 1H), 7.26 (m, 2H), 6.05 (d, 1H), 3.36 (t, 2H), 3.20 (s, 3H), 2.80 (m, 2H).

N-(2-bromophenyl)-N'[4-chloro-2-hydroxy-3-[N"-(2-methoxyethyl)-aminosulfonyl]phenyl] urea Following the general procedure for urea formation outlined in example 15, N-(2-methoxyethyl)-3-amino-6-chloro-2-hydroxybenzenesulfonamide (140 mg, 0.50 mmol) and 2-bromophenylisocyanate (119 mg, 0.60 mmol) were coupled to form the desired urea (174 mg, 72%). EI-MS (m/z) 476.0, 478.0, 479.9 (M⁻).

Example 17

Preparation of N-[4-chloro2-hydroxy-3-(3-carboxyethylaminosulfonyl)phenyl]-N'-(2-chlorophenyl) urea.

a) N-(3-ethoxycarbonylethyl)-2,6-dichloro-3-nitrobenzenesulfonamide

Following the general procedure for sulfonamide formation outlined in example 15, 2,6-dichloro-3-nitrobenzenesulfonyl chloride (1.5 g, 5.17 mmol), β-alanine ethyl ester (0.95 mL, 6.2 mmol) and triethylamine (1.8 mL, 12.9 mmol) were reacted to form the desired product (1.8 g, 94%). EI-MS m/z 370 (M-H)⁻.

b) N-(3-carboxyethyl)-6-chloro-2-hydroxy-3-nitrobenzenesulfonamide

Following the general hydrolysis procedure outlined in example 15, N-(3-ethoxycarbonylethyl)-2,6-dichloro-3-nitrobenzenesulfonamide (1.82 g, 4.9 mmol), NaH (60%, 588 mg, 14.7 mmol) and water (106 mg, 5.88 mmol) were reacted to form the desired product (1.0 g, 63%). EI-MS m/z 323.5 (M-H)⁻.

c) N (3-carboxyethyl)-3-amino-6-chloro-2-hydroxybenzenesulfonamide

Following the general hydrogenation procedure outlined in example 15, N-(3-carboxyethyl)-6-chloro-2-hydroxy-3-nitrobenzenesulfonamide (100 mg, 0.3 mmol) was reduced with hydrogen and Pd/C (100 mg) to form the desired product (62 mg, 68 %). EI- MS m/z 293.5 (M-H)⁻.

d) N-[4-chloro-2-hydroxy-3-(3-carboxyethylaminosulfonyl) phenyl]-N'(2-bromophenyl1) urea Following the general procedure for urea formation outlined in example 15, N-(3-carboxyethyl)-3-amino-6-chloro-2-hydroxybenzenesulfonamide (62 mg, 0.21 mmol) and 2-bromophenylisocyanate (42 mg, 0.21 mmol) were coupled to form the desired urea (35 mg, 34 %). EI-MS m/z 491.7 (M-H)$^-$.

Example 18, 19 and 20

Preparation of N-(2-bromophenyl)-N'-[4-chloro-2-hydroxy-3-(isopropylaminosulfonyl)phenyl] urea, N-[4-chloro-2-hydroxy-3-(isopropylaminosulfonyl) phenyl]-N'-(2-chlorophenyl) urea and N-[4-chloro-2-hydroxy-3-(isopropylaminosulfonyl)phenyl]-N'-(2,3-dichlorophenyl) urea.

a) N-isopropyl-2,6-dichloro-3-nitrobenzenesulfonamide

Following the general procedure for sulfonamide formation outlined in example 15, 2,6-dichloro-3-nitrobenzenesulfonyl chloride (1.5 g, 5.17 mmol), isopropylamine (0.44 m, 5.17 mmol) and triethylamine (1.08 mL, 7.76 mmol) were reacted to form the desired product (1.3 g, 81 %). EI-MS m/z 312 (M-H)$^-$.

b) N-isopropyl-6-chloro-2-hydroxy-3-nitrobenzenesulfonamide

Following the general hydrolysis procedure outlined in example 15, N-isopropyl-2,6-dichloro-3-nitrobenzenesulfonamide (1.3 g, 4.15 mmol), NaH (60%, 500 mg, 12.45 mmol) and water (89 mg, 4.98 mmol) were reacted to form the desired product (0.7 g, 57%). EI- MS m/z 293.5 (M-H)$^-$.

c) N-isopropyl-3-amino-6-chloro-2-hydroxybenzenesulfonamide

Following the general hydrogenation procedure outlined in example 15, N-isopropyl-6-chloro-2-hydroxy-3-nitrobenzenesulfonamide (0.7 g, 2.38 mmol) was reduced with hydrogen and Pd/C (0.7 g) to form the desired product (0.62 g, 98 %). EI-MS m/z 263.5 (M-H)$^-$.

d) N-(2-bromophenyl)-N'-4-chloro-2-hydroxy-3-(isopropylaminosulfonyl)phenyl] urea Following the general procedure for urea formation outlined in example 15, N-isopropyl-3-amino-6-chloro-2-hydroxybenzenesulfonamide (220 mg, 0.88 mmol) and 2-bromophenylisocyanate (174 mg, 0.88 mmol) were coupled to form the desired urea (110 mg, 29%). EI-MS m/z 461.7 (M-H)$^-$.

e) N-[4-chloro-2-hydroxy-3-(isopropylaminosulfonyl) phenyl]-N'-(2,3-dichlorophenyl) urea.

Following the general procedure for urea formation outlined in example 15, N-isopropyl-3-amino-6-chloro-2-hydroxybenzenesulfonamide (188 mg, 0.75 mmol) and 2,3-dichlorophenylisocyanate (141 mg, 0.75 mmol) were coupled to form the desired urea (104 mg, 32%). EI-MS m/z 451.7 (M-H)$^-$.

f) N-[4-chloro-2-hydroxy-3-(isopropylaminosulfonyl) phenyl]-N'-(2-chlorophenyl) urea Following the general procedure for urea formation outlined in example 15, N-isopropyl-3-amino-6-chloro-2-hydroxybenzenesulfonamide (220 mg, 0.88 mmol) and 2-chlorophenylisocyanate (135 mg, 0.88 mmol) were coupled to form the desired urea (110 mg, 32%). EI-MS m/z417.1 (M-H)$^-$.

Example 21

N-(4-chloro-2-hydroxy-3-aminosulfonylphenyl)-N'-(2-methoxyphenyl) urea

Following the general procedure for urea formation outlined in example 12, 3-amino-6-chloro-2-hydroxybenzenesulfonamide (40 mg, 0.18 mmol) and 2-methoxyphenylisocyanate (33 mg, 0.22 mmol) ) were coupled to form the desired urea (23 mg, 34%). EI-MS (m/z) 370.3, 372.1(M).

Example 22

N-(4-chloro-2-hydroxy-3-aminosulfonylphenyl)-N'-(2,3-methylenedioxyphenyl) urea 2,3-(methylenedioxy)benzoic acid A solution of 2,3-(methylenedioxy)benzaldehyde (160mg, 1.06mmol), potassium carbonate (960 mg, 6.9 mmol) and 2.4mL of hydrogen peroxide (30–32 wt.% solution in water) in 10 mL of methanol was stirred for 16 hours at room temperature. The mixture was washed with diethyl ether. The water layer was acidified with 1 N aq. HCl to pH>1, then extracted with ethyl acetate. The organic layer was dried over MgSO$_4$, then concentrated to give the desired product (170mg, 96%). EI-MS (m/z) 164.8 (M$^-$).

N-(4-chloro-2-hydroxy-3-aminosulfonylphenyl)-N'(2,3-methylenedioxyphenyl) urea

A mixture of 2,3-(methylenedioxy)benzoic acid (170mg, 1.02mmol), diphenylphosphoryl azide (338 mg, 1.23 mmol) and triethylamine (0.17mL, 1.23 mmol) was stirred at room temperature for 3 days. The mixture was concentrated. To the residue in 1 mL of N,N-dimethylformamide was added 3-amino-6-chloro-2-hydroxybenzenesulfonamide (40 mg, 0.18 mmol). The resulting mixture was stirred at room temperature for 16 hours. Purification by column chromatography on silica gel, eluting with ethyl acetate/hexane (50/50, v/v), gave the desired product (40 mg, 10%). EI-MS (m/z) 386.2, 388.2 (M$^-$).

Example 23

N-(2-benzyloxyphenyl)-N'-(4-chloro-2-hydroxy-3-aminosulfonylphenyl) urea

Following the general procedure for urea formation outlined in example 12, 3-amino-6-chloro-2-hydroxybenzenesulfonamide (52 mg, 0.23 mmol) and 2-benzyloxyphenylisocyanate (40 mg, 0.17 mmol) were coupled to form the desired urea (20 mg, 26%). EI-MS (m/z) 446.2, 448.3, 450.2 (M$^-$).

Example 24

N-[3-(N''-allylaminosulfonyl)-4-chloro-2-hydroxyphenyl]-N'-(2,3-dichlorophenyl) urea N-allyl-2-acetyl-6-chloro-3-nitro-benzenesulfonamide A mixture of 2-acetyl-6chloro-3-nitrobenzenesulfonamide (150 mg, 0.51 mmol), potassium carbonate (84 mg, 0.61 mmol) and allyl bromide (0.18mL, 2.mmol) in 3 mL of N, N-dimethylformamide was heated to 60° C. for 4 days. The mixture was acidified with 1 N aq. HCl, then extracted with ethyl acetate. The solvent was concentrated to give the crude material. Colurnt chromatography on silica gel, eluting with ethyl acetate/hexane/acetic acid (50/49/1, v/v/v), gave the desired product (40 mg, 12%). EI-MS (m/z) 333.3, 335.2 (M$^-$).

N-allyl-6-chloro-2-hydroxy-3-nitrobenzenesulfonamide

A solution of N-allyl-2-acetyl-6-chloro-3-nitrobenzenesulfonamide (30 mg, 009 mmol), 0.mL of chlorotrimethylsilane and 2 drops of fuming sulfuric acid in ethanol was heated to reflux for 20 hours. The solvent was evaporated. The residue was diluted with ethyl acetate and washed with water. The organic layer was then dried (Na, SO$_4$) and concentrated to give the desired product (26 mg, 100%). $^1$H NMR (MeOD-d$_4$): δ 8.01(d, 1H), 7.20 (d, 1H), 5.70 (m, 1H), 5.16 (m, 1H), 5.05 (m, 1H), 3.62 (m, 2H).

N-allyl-3-amino-6-chloro2-hydroxybenzenesulfonamide

A solution of N-allyl-6-chloro-2-hydroxy-3-nitrobenzenesulfonamide (25 mg, 0.09 mmol) and tin (II) chloride dihydrate (101 mg, 0.44mmol) in 5 mL of ethanol was stirred at room temperature. The mixture was concentrated, the residue was diluted with ethyl acetate and 10% aq. NaHCO$_3$. The organic layer was dried over Na$_2$SO$_4$ and concentrated to give the crude product (20 mg) which was carried on to the next step without purification. EI-MS (m/z) 263.1, 265.2 (M$^-$).

N-[3-(N"-allylaminosulfonyl)4-chloro-2-hydroxyphenyl]-N'-(2,3-dichlorophenyl) urea A solution of crude N-allyl-3-amino-6-chloro-2-hydroxybenzenesulfonamide (20 mg) and 2,3-dichlorophenylisocyanate (12 μL, 0.09 mmol) in 1 mL of N,N-dimethylformamide was stirred at room temperature for 20 hours. The mixture was diluted with ethyl acetate and washed with water to give the crude material. Purification by column chromatography on silica gel, eluting with ethyl acetate/hexane (30/70, v/v), gave the desired product (10 mg, 29% for two steps). EI-MS (m/z) 450.2, 452.2, 454.1 (M$^-$).

Example 25

Preparation of N-[4-chloro-2-hydroxy-3-[N"-(2-trifluoroethyl)aminosulfonyl]phenyl]-N'-(2,3-dichlorophenyl) urea 2,6-Dichloro-3-nitrobenzenesulfonic acid Lithium hydroxide hydrate (12.64 g, 0.301 mol) was added to a solution of 2,6-dichlorobenzenesulfonyl chloride (35.53 g, 0.146 mol) in MeOH (600 mL) and the reaction was allowed to stir at room temperature for 3 hr. The reaction mixture was filtered to remove suspended solids and then concentrated. The resulting solid was dried in vacuo overnight to remove any residual MeOH. The solid was then dissolved in H$_2$SO$_4$ (300 mL) and chilled in an ice bath. A solution of H$_2$S0$_4$ (35 mL) and HNO$_3$ (13.2 mL) was slowly added to the above reaction over 90 min. The reaction was allowed to warm up to room temperature overnight and then slowly poured into ice water (1200 mL) and extracted with EtOAc. The combined organic layers were dried (MgSO$_4$) and concentrated to yield 2,6-dichloro-3-nitrobenzenesulfonic acid (44.35 g, 99%) as the dihydrate. EI-MS (m/z) 270 (M-H)$^-$.

2,6-Dichloro-3-nitrobenzenesulfonyl chloride

Potassium hydroxide (12.07 g, 0.215 mol) was added to a solution of 2,6-dichloro-3-nitrobenzenesulfonic acid dihydrate (44.35 g, 0.144 mol) in MeOH (850 mL) and the reaction was allowed to stir at room temperature for 14 hr. The reaction mixture was concentrated and the resulting solid was dried in vacuo overnight. To this was added PCl$_5$ (30.00 g, 0.144 mol) followed by POCl$_3$ (475 mL) and the mixture was refluxed overnight. The reaction was then cooled to room temperature and concentrated. The resulting mixture was taken up in EtOAc and chilled in an ice bath. Ice chunks were slowly added to the reaction mixture to quench any leftover PClI. When bubbling ceased, water was added and the reaction mix was extracted with EtOAc. The organic layer was dried (MgSO$_4$) and concentrated to yield 2,6-Dichloro-3-nitrobenzenesulfonyl chloride (40.42 g, 97%). $^1$H NMR (DMSO-d$_6$) δ 7.88 (d, 1H), 7.75 (d, 1H).

N-(2-trifluoroethyl)-2,6-dichloro-3-nitrobenzenesulfonamide

Following the general procedure for sulfonamide formation outlined in example 15, 2,6-dichloro-3-nitrobenzenesulfonyl chloride (560 mg, 1.93 mmol), 2-trifluoroethylamine hydrochloride (261 mg, 1.93 mmol) and triethylamine (0.89mL, 5.79 mmol) were reacted to form the desired product (490 mg, 72%). EI-MS (m/z) 351.1, 353.1 (M$^-$).

N-(2-trifluoroethyl)-6chloro-2-hydroxy-3-nitrobenzenesulfonamide

To a solution N-(2-trifluoroethyl)-2,6-dichloro-3-nitrobenzenesulfonamide (130 mg, 0.36 mmol) in 5mL of tetrahydrofuran was added 60% NaH (43 mg, 1.08 mmol) and methanol (15 μL, 0.36 mmol). The mixture was stirred for 16 hours at room temperature. Purification by column chromatography on silica gel, eluting with ethyl acetate/hexane/acetic acid (49/50/1, v/v/v), gave the desired product (44 mg, 33%). EI-MS (m/z) 333.1, 335.1 (M$^-$).

N-(2-trifluoroethyl)-3-amino-6-chloro-2-hydroxybenzenesulfonamide

Following the general hydrogenation procedure outlined in example 15,

N-(2-trifluoroethyl)-6-chloro-2-hydroxy-3-nitrobenzenesulfonamide (40 mg, 0.12 mmol) was reduced with hydrogen and 10% Pd/C (20 mg) to form the desired product (36 mg, 100%). EI-MS (m/z) 303.1, 305.1 (M$^-$).

N[4-chloro-2-hydroxy-3-[N"-(2-trifluoroethyl) aminosulfonyl]phenyl]-N'(2,3-dichlorophenyl) urea Following the general procedure for urea formation outlined in example 15, N-(2-trifluoroethyl)-3-amino-6-chloro-2-hydroxybenzenesulfonamide (36 mg, 0.12 mmol) and 2,3-dichlorophenylisocyanate (27 mg, 0.14 mmol) were coupled to form the desired urea (23 mg, 38%). $^1$H NMR (MeOD-d$_4$): δ 8.28 (d, 1H), 8.05 (m, 1H), 7.24 (m, 2H), 7.05 (d, 1H), 3.79 (m, 2H).

Example 26 and 27

Preparation of N-(2,3-dichlorophenyl)-N'-[2-hydroxy-4-methoxy-3-(N"-phenylaminosulfonyl) phenyl] urea and N-(2-bromophenyl)-N'-[2-hydroxy-4-methoxy-3-(N'-phenylaminosulfonyl) phenyl] urea N-phenyl-2,6-dichloro-3-nitrobenzenesulfonamide Following the general procedure for sulfonamide formation outlined in example 15, 2,6-dichloro-3-nitrobenzenesulfonyl chloride (540 mg, 1.85 mmol), aniline (173 mg, 1.85 mmol) and triethylamine (0.61 mL, 5.55 mmol) were reacted to form the desired product (1 30 mg, 20%). $^1$NMR (MeOD-d$_4$): δ7.65 (d, 1H), 7.58 (d, 1H), 7.40 (t, 2H), 7.15 (m, 3H).

N-phenyl-2-hydroxy-6-methoxy-3-nitrobenzenesulfonamide

Following the hydrolysis procedure outlined in example 25, N-phenyl-2,6-dichloro-3-nitrobenzenesulfonamide (130 mg, 0.37 mmol), 60% NaH (44 mg, 1.11 mmol) and methanol (15 μL, 0.37 mmol) were reacted. The crude mixture (70 mg) was carried on to the next step without purification.

N-phenyl-3-amino-2-hydroxy-6-methoxybenzenesulfonamide

Following the general hydrogenation procedure outlined in example 15, crude N-phenyl-2-hydroxy-6-methoxy-3-nitrobenzenesulfonamide (70 mg) was reduced with hydrogen and 10% Pd/C (35 mg). The crude mixture was carried on to the next step without purification.

N-(2,3-dichlorophenyl)-N!42-hydroxy-4-methoxy-3-(N"-phenylaminosulfonyl)-phenyl] urea Following the general procedure for urea formation outlined in example 15, crude N-phenyl-3-amino-2-hydroxy-6-methoxybenzenesulfonamide and 2,3- dichlorophenylisocyanate (43 mg, 0.23 mmol) were coupled to form the desired urea (3.5 mg, 4% for 3 steps). EI-MS (m/z) 480.2, 482.1 (M⁻).

N-(2-bromophenyl)-N'[2-hydroxy4-methoxy-3-(N"-phenylaminosulfonyl)-phenyl] urea

Following the general procedure for urea formation outlined in example 15, crude N-phenyl-3-amino-2-hydroxy-6-methoxybenzenesulfonamide and 2-bromophenylisocyanate (46 mg, 0.23mmol) were coupled to form the desired urea (5.mg, 5.6%). EI-MS (m/z) 490.1, 492.1 (M⁻).

Example 30 and 31

Preparation of N-(2-bromophenyl)-N'-[4-chloro-2-hydroxy-3-(4-morpholinylsulfonyl)phenyl] urea and N-[4-chloro-2-hydroxy-3-(4-morpholinylsulfonyl) phenyl]-N'-(2,3-dichlorophenyl) urea 2,6-dichloro- -(4-morpholinylsulfonyl)-3-nitrobenzene Following the general procedure for sulfonamide formation outlined in example 15, 2,6-dichloro-3-nitrobenzenesulfonyl chloride (500 mg, 1.72 mmol), morpholine (150 mg, 1.72 mmol) and triethylamine(479 μL, 3.44 mmol) were reacted to form the desired product (430 mg, 73%). LC-MS (m/z) 341.0 (M⁻).

6-chloro-2-hydroxy- I -(4-morpholinylsulfonyl)-3-nitrobenzene

Following the general hydrolysis procedure outlined in example 15, 2,6-dichloro-1-(4-morpholinylsulfonyl)-3-nitrobenzene (410 mg, 1.20 mmol), 60 % NaH (144 mg, 3.6 mmol) and water (26 μL, 1.44 mmol) were reacted to form the desired product (220 mg, 57%). EI-MS (m/z) 321.1, 323.1 (M⁻).

4-chloro-2-hydroxy-3-(4-morpholinylsulfonyl)aniline

Following the general hydrogenation procedure outlined in example 15, 6-chloro-2-hydroxy-1-(4-morpholinylsulfonyl)-3-nitrobenzene (210 mg, 0.65 mmol) was reduced with hydrogen and Pd/C (100 mg) to form the desired product (180 mg, 95%). ¹H NMR (MeOD-d₄): δ 6.28 (mn, 2H), 3.68 (t, 4H), 3.30 (t, 4H).

N-(2-bromophenyl)-Nu[4-chloro-2-hydroxy-3-(4-morpholinylsulfonyl)phenyl] urea

Following the general procedure for urea formation outlined in example 15, 4-chloro-2-hydroxy-3-(4-morpholinylsulfonyl)aniline (90 mg, 0.31 mmol) and 2-bromophenylisocyanate(46 μL, 0.37 mmol) were coupled to form the desired urea (81 mg, 53%). EI-MS (m/z) 487.76, 489.75, 491.74 (M⁻).

N-[4-chloro-2-hydroxy-3-(4-morpholinylsulfonyl)phenyl]-N'-(2,3-dichlorophenyl) urea Following the general procedure for urea formation outlined in example 15, 4-chloro-2-hydroxy-3-(4-morpholinylsulfonyl)aniline (90 mg, 0.31 mmol) and 2,3-dichlorophenylisocyanate (70 μL, 0.37 mmnol) were coupled to form the desired urea (77 mg, 52%). EI-MS (m/z) 477.68, 479.72, 481.63 (M⁻).

Example 32 and 36

Preparation of N-[3-[N"-[3-(tert-butoxycarbonylamino)-propyl]aminosulfonyl]4-chloro-2-hydroxyphenyl]-N'-(2,3-dichlorophenyl) urea and N-[3-[N"-(3-aminopropyl)aminosulfonyl]-4-chloro-2-hydroxyphenyl]-N'-(2,3-dichlorophenyl) urea trifluoroacetate N-[3-(tert-butoxycarbonylamino)propyl]-2,6-dichloro-3-nitrobenzenesulfonamide Following the general procedure for sulfonamide formation outlined in example 15, 2,6-dichloro-3-nitrobenzenesulfonyl chloride (1.0 g, 3.44 mmnol), t-butyl N-(3-aminopropyl)carbamate (0.60 mg, 3.44 mmol) and triethylamine(960 μL, 6.88 mmol) were reacted to form the desired product (1.44 g, 98%). EI-MS (m/z) 426.1, 428.1, 430.1 (M-H)⁻.

N-[3-(tert-butoxycarbonylamino)propyl]-6-chloro-2-hydroxy-3-nitrobenzenesulfonamide Following the general hydrolysis procedure outlined in example 15, N-[3-(tert-butoxycarbonylamino)propyl]-2,6-dichloro-3-nitrobenzenesulfonamide (450 mg, 1.05 mmol), 60% NaH (168 mg, 4.2 mmol) and water (21 μL, 1.15 mmol) were reacted to form the desired product (250 mg, 58%). EI-MS (m/z) 408.1, 410.1 (M-H)⁻.

N-[3-(tert-butoxycarbonylamino)propyl]-3-amino-6-chloro-2-hydroxybenzenesulfonamide Following the general hydrogenation procedure outlined in example 15, N-[3-(tert-butoxycarbonylamino)propyl]-6-chloro-2-hydroxy-3-nitrobenzene-sulfonamide (250 mg, 0.61 mmol) was reduced with hydrogen and 10% Pd/C (100 mg) to form the desired product (220 mg, 95%). ¹H NMR (MeOD-d₄): δ 6.82 (m, 2H), 3.06 (t, 2H), 2.92 (t, 2H), 1.60 (m, 2H), 1.41 (s, 9H).

N-[3-[N"-[3-(tert-butoxycarbonylamino)propyl] aminosulfonyl]-4-chloro-2-hydroxyphenyl]- N'-(2,3-dichlorophenyl) urea Following the general procedure for urea formation outlined in example 15, N-[3-(tert-butoxycarbonylamino) propyl]-3-amino-6-chloro-2-hydroxybenzenesulfonamide (110 mg, 0.29 mmol) and 2,3-dichlorophenylisocyanate (65 mg, 0.35 mmol) were coupled to form the desired urea (90 mg, 55%). EI-MS (m/z) 565.64, 567.74, 569.60 (M⁻).

The following is the general procedure for Boc deprotection

N-[3-[N"-(3-aminopropyl)aminosulfonyl]-4-chloro-2-hydroxyphenyl]-N'(2,3-dichlorophenyl) urea trifluoroacetate A solution of N[³-[N"-[3-(tert-butoxycarbonylamino) propyl]aminosulfonyl]-4-chloro-2-hydroxyphenyl]-N'-(2,3-dichlorophenyl) urea (33 mg, 0.058 mmol) in 1 mL of trifluoroacetic acid was stirred at room temperature for 30 min. The solvent was concentrated. The residue was diluted with methanol, then concentrated. The process was repeated twice to give crude material. Recrystallization from methanol and water produced desired product (23 mg, 68%). EI-MS (m/z) 466.7, 468.8, 470.8 (M⁻).

Example 33, 34 and 35

Preparation of N-(2-bromophenyl)-N'-[3-[N"-[3-(tert-butoxycarbonylamino) propyl]aminosulfonyl]-4-chloro-2-hydroxyphenyl] urea, N-[3-[N"-(3-aminopropyl)aminosulfonyl]-4-chloro-2-hydroxyphenyl]-N'-(2-bromophenyl) urea trifluoroacetate and N-[3-[N"-(3-aminopropyl) aminosulfonyl]-4-chloro-2-hydroxyphenyl]-N'-(2 bromophenyl) urea hydrochloride N-(2-bromophenyl)-N'-[3-[N"-[3-(tert-butoxycarbonylamino)propyl]-aminosulfonyl]4-chloro-2-hydroxyphenyl] urea Following the general procedure for urea formation outlined in example 15, N-[3-(tert-butoxycarbonylamino)propyl]-3-amino-6-chloro-2-hydroxybenzenesulfonamide (110 mg, 0.29 mmol) and 2-bromophenylisocyanate (69 mg, 0.35 mmol) were coupled to form the desired urea (140 mg, 84 %). EI-MS (m/z) 575.53, 577.61, 579.62 (M⁻).

N-[3-[N"-(3-aminopropyl)aminosulfonyl]-4-chloro-2-hydroxyphenyl]-N'-(2-bromophenyl) urea trifluoroacetate Following the general procedure for Boc deprotection outlined in example 36, N-(2-bromophenyl)-N'[3-[N"-[3-(t-butoxycarbonylamino)propyl]aminosulfonyl]-4-chloro-2-hydroxyphenyl] urea (21 mg, 0.036 mmol) was stirred in 1 mL of trifluoroacetic acid to from the desired product (16 mg, 75%). $^1$H NMR (MeOD-d$_4$): δ 8.28 (d, 1H), 7.80 (d, 1H), 7.59 (d, 1H), 7.33 (t, 1H), 7.07 (d, 1H), 7.02 (d, 1H) 3.05 (m, 4H) 1.87 (m, 2H).

N-[3-[N"-(3-aminopropyl)aminosulfonyl]-4-chloro-2-hydroxyphenyl]-N'-(2-bromophenyl) urea hydrochloride A solution of N-(2-bromophenyl)-N'-[3-[N"-[3-(tert-butoxycarbonylamino)-propyl]aminosulfonyl]-4-chloro-2-hydroxyphenyl] urea (59 mg, 0.102 mmol) in 1 mL of 4.0 M HCl in 1,4-dioxane was stirred at room temperature for 10 min. The solvent was concentrated. Recrystallization from acetone and hexane produced desired product (45 mg, 85%). LC-MS 477.0 (M$^+$).

Example 37 and 38

Preparation of N-(2-bromophenyl)-N'-[3-[N"-[2-(tert-butoxycarbonylamino)ethyl]aminosulfonyl]-4-chloro-2-hydroxyphenyl] urea and N-[3-[N"-(2-aminoethyl)aminosulfonyl]-4-chloro-2-hydroxyphenyl]-N'-(2-bromophenyl) urea t-butyl N-(2-aminoethyl)carbamate A solution of ethylenediamine (3.0 g, 49.9 mmol), di-tert-butyl-dicarbonate (3.63 g, 16.6 mmol) and triethylamine (6.95 mL, 49.9 mmol) in 100 mL of dichloromethane was stirred at room temperature for 16 hours. The mixture was filtered to remove the solid produced during reaction. The filtrate was washed with water, dried over MgSO$_4$, concentrated and dried in vacuo to give the desired product (1.79 g, 67%). LC-MS 160.97 (M$^+$).

N-[2-(tert-butoxycarbonylamino)ethyl]-2,6-dichloro-3-nitrobenzenesulfonamide

Following the general procedure for sulfonamide formation outlined in example 15, 2,6-dichloro-3-nitrobenzenesulfonyl chloride (1.0 g, 3.44 mmol), t-butyl N-(2-aminoethyl)carbamate (0.5 g, 3.44 mmol) and triethylanine(0.72 mL, 5.16 mmol) were reacted to form the desired product (1.29 g, 90%). $^1$H NMR (MeOD-d$_4$): δ 7.93 (d, 1H), 7.78 (d, 1H), 3.12 (m, 4H), 1.41 (s, 9H).

N-(2-(tert-butoxycarbonylamino)ethyl]-6-chloro-2-hydroxy-3-nitrobenzenesulfonamide Following the general hydrolysis procedure outlined in example 15, N-[2-(tert-butoxycarbonylamino)ethyl]-2,6-dichloro-3-nitrobenzenesulfonamide (1.63 g, 3.94 mmol), 60% NaH (630 mg, 15.8 mmol) and water (71 μL, 3.94 mmol) were reacted to form the desired product (200 mg, 13%). $^1$H NMR (MeOD-d$_4$): δ 8.10 (d, 1H), 7.21 (d, 1H), 3.15 (t, 2H), 3.08 (t, 2H), 1.41 (s, 9H).

N-[2-(tert-butoxycarbonylamino)ethyl]-3-amino-6-chloro-2-hydroxybenzenesulfonamide Following the general hydrogenation procedure outlined in example 15, N-[2-(tert-butoxycarbonylamino)ethyl]-6-chloro-2-hydroxy-3-nitrobenzenesulfonamide (200 mg, 0.51 mmol) was reduced with hydrogen and 10% Pd/C (100 mg) to form the desired product (170 mg, 92%). $^1$H NMR (MeOD-d$_4$): δ 6.84 (m, 2H), 3.15 (t, 2H), 2.95 (t, 2H), 1.42 (s, 9H).

N-(2-bromophenyl)-N'-[3-[N"-[2-(tert-butoxycarbonylamino)ethyl]-aminosulfonyl3-4-chloro-2-hydroxyphenyl] urea Following the general procedure for urea formation outlined in example 15, N-[2-(tert-butoxycarbonylamino)ethyl]-3-amino-6-chloro-2-hydroxybenzenesulfonamide (170 mg, 0.47 mmol) and 2-bromophenylisocyanate (92 mg, 0.47 mmol) were coupled to form the desired urea (I20 mg, 49%). LC-MS 565.0 (M$^+$).

N-[3-[N"-(2-aminoethyl)aminosulfonyl]-4-chloro-2-hydroxyphenyl]-N'-(2-bromophenyl) urea trifluoroacetate Following the general procedure for Boc deprotection outlined in example 36, N-(2-bromophenyl)-N'[3-[N"-[2-(tert-butoxycarbonylamino)ethyl]aminosulfonyl]4-chloro-2-hydroxyphenyl] urea (80 mg, 0.14 mmol) was stirred in trifluoroacetic acid to form the desired product (22 mg, 34%). LC-MS 465.0 (M$^+$).

Example 39 and 42

Preparation of N-(2-bromophenyl)-N'-[3-[[4-(tert-butoxycarbonyl)piperazin-1-yl]sulfonyl]-4-chloro-2-hydroxyphenyl] urea and N-(2-bromophenyl)-N'-[4-chloro-2-hydroxy-3-(piperazin-1-yl)sulfonylphenyl] urea trifluoroacetate 1-[4-(tert-butoxycarbonyl)piperazin-1-yl]sulfonyl-2,6-dichloro-3-nitrobenzene Following the general procedure for sulfonamide formation outlined in example 15, 2,6-dichloro-3-nitrobenzenesulfonyl chloride (500 mg, 1.72 mmol), tert-butyl 1-piperazinecarboxylate (320 mg, 1.72 mmol) and triethylamine (479 μL, 3.44 mmol) were reacted to form the desired product (650 mg, 84%). LC-MS (m/z) 440.2 (M$^+$).

1-[4-(tert-butoxycarbonyl)piperazin-1-yl]sulfonyl-6-chloro-2-hydroxy-3-nitrobenzene Following the general hydrolysis procedure outlined in example 15, 1-[4-(tert-butoxycarbonyl)piperazin-1-yl]sulfonyl-2,6-dichloro-3-nitrobenzene (200 mg, 0.45 mmol), 60% NaH (54 mg, 1.35 mmol) and water (8μL, 0.45 mmol) were reacted to form the desired product (60 mg, 32%). EI-MS (m/z) 420.1, 422.1 (M$^+$).

3-[4-(tert-butoxycarbonyl)piperazin-1-yl]sulfonyl-4-chloro-2-hydroxyaniline

Following the general hydrogenation procedure outlined in example 15, 1-[4-(tert-butoxycarbonyl)piperazin-1-yl]sulfonyl-6-chloro-2-hydroxy-3-nitrobenzene (256 mg, 0.61 mmol) was reduced with hydrogen and 10% Pd/C (120 mg) to form the desired product (220 mg, 93%). $^1$H NMR (MeOD-d$_4$): δ 6.84 (m, 2H), 3.45 (m, 4H), 3.27 (m, 4H), 1.43 (s, 9H).

N-(2-bromophenyl)-N'-[3-[[4-(tert-butoxycarbonyl)piperazin-1-yl]sulfonyl]-4-chloro-2-hydroxyphenyl] urea Following the general procedure for urea formation outlined in example 15, 3-[4-(tert-butoxycarbonyl)piperazin-1-yl]sulfonyl-4-chloro-2-hydroxyaniline (110 mg, 0.28 mmol) and 2-bromophenylisocyanate (67 mg, 0.34 mmol) were coupled to form the desired urea (60 mg, 36%). Element Analysis Theory: C 44.80%, H 4.44%, N 9.50%, Found: C 44.65%, H 4.15%, N 9.20%.

N-(2-bromophenyl)-N'-[4-chloro-2-hydroxy-3-(piperazin-1-yl)sulfonylphenyl) urea trifluoroacetate Following the general procedure for Boc deprotection outlined in example 36, N-(2-bromophenyl)-N'-[3-[[4-(tert-butoxycarbonyl)piperazin-1-yl]sulfonyl]4-chloro-2-hydroxyphenyl] urea (10 mg, 0.019 mmol) was stirred in trifluoroacetic acid to form the desired product (5 mg, 49%).

¹H NMR (MeOD-d₄): δ 8.28 (d, 1H), 7.91 (d, 1H), 7.60 (d, 1H), 7.33 (t, 1H), 7.14 (d, 1H), 7.02 (d, 1H) 3.64 (t, 4H) 3.33 (m, 4H).

Example 40 and 41

Preparation N-[3-[4-(tert-butoxycarbonyl)piperazin-1-yl]sulfonyl-4-chloro-2-hydroxyphenyl]-N'-(2,3-dichlorophenyl) urea and N-[4-chloro-2-hydroxy-3-(piperazin-1-yl)sulfonylphenyl]-N'-(2,3-dichlorophenyl) urea trifluoroacetate N-[3-[4-(tert-butoxycarbonyl)piperazin-1-yl]sulfonyl4-chloro-2-hydroxyphenyl]-N'-(2,3- dichlorophenyl) urea Following the general procedure for urea formation outlined in example 15, 3-[4-(tert- butoxycarbonyl)piperazin-1-yl]sulfonyl4-chloro-2-hydroxyaniline (110 mg, 0.28 mmol) and 2,3-dichlorophenylisocyanate (64 mg, 0.34 mmol) were coupled to form the desired urea (34 mg, 25%). EI-MS (m/z) 576.65, 578.65, 580.67 (M⁻).

N-[4-chloro-2-hydroxy-3-(piperazin-1-yl) sulfonylphenyl]-N'-(2,3-dichlorophenyl) urea trifluoroacetate Following the general procedure for Boc deprotection outlined in example 36, N-[3-[4-(tert-butoxycarbonyl) piperazin-1-yl]sulfonyl-4-chloro-2-hydroxyphenyl]-N'-(2,3-dichlorophenyl) urea (20 mg, 0.034 mmol) was stirred in trifluoroacetic acid to form the desired product (13.5 mg, 66%). EI-MS (m/z) 481.7, 483.7, 485.7 (M⁺).

Example 43, 51 and 60

Preparation of N-[4-chloro-2-hydroxy-3-[N"-(3-methylthiopropyl)aminosulfonyl]phenyl]-N'-(2,3-dichlorophenyl) urea, N-[4-chloro-2-hydroxy-3-[N"-[3-(methylsulfonyl)propyl]aminosulfonyl]phenyl]-N'-(2,3-dichlorophenyl) urea, and N-[4-chloro-2-hydroxy-3-[N"-[3-(methylsulfinyl)propyl]aminosulfonyl]phenyl]-N'-(2,3-dichlorophenyl) urea N-(3-methylthiopropyl)-2,6-dichloro-3-nitrobenzenesulfonamide Following the general procedure for sulfonamide formation outlined in example 15, 2,6- dichloro-3-nitrobenzenesulfonyl chloride (2 g, 6.88 mmol), 3-(methylthio)propylamine (0.72 g, 6.88 mmol) and triethylamine (1.92 mL, 13.76 mmol) were reacted to form the desired product (2.07 g, 82%). ¹H NMR (MeOD-d₄): δ 7.93 (d, 1H), 7.79 (d, 1H), 3.16 (t, 2H), 2.47 (t, 2H), 2.00 (s, 3H), 1.76 (m, 2H).

N(3-methylthiopropyl)-6-chloro-2-hydroxy-3-nitrobenzenesulfonamide

Following the general hydrolysis procedure outlined in example 15, N-(3-methylthiopropyl)-2,6-dichloro-3-nitrobenzenesulfonamide (1.0 g, 2.78 mmol), 60% NaH (330 mg, 8.13 mmol) and water (59 µL, 3.25 mmol) were reacted to form the desired product (650 mg, 69%). EI-MS (m/z) 339.86, 341.84 (M⁻).

N(3-methylthiopropyl)-3-amino-6-chloro-2-hydroxybenzenesulfonamide

Following the general hydrogenation procedure outlined in example 15,

N-(3- methylthiopropyl)-6-chloro-2-hydroxy-3-nitrobenzenesulfonamide (300 mg, 0.88 mmol) was reduced with hydrogen and 10% Pd/C (150 mg) to form the desired product (250 mg, 91%). ¹H NMR (MeOD-d₄): δ 6.84 (d, 1H), 6.77 (d, 1H), 2.93 (t, 2H), 2.40 (t, 2H), 1.89 (s, 3H), 1.63 (m, 2H).

N-[4-chloro-2-hydroxy-3-[N"-(3-methylthiopropyl)aminosulfonyl]phenyl]-N'-(2,3-dichlorophenyl) urea Following the general procedure for urea formation outlined in example 15, N-(3-methylthiopropyl)-3-amino-6-chloro-2-hydroxybenzenesulfonamide (250 mg, 0.80 mmol) and 2,3dichlorophenylisocyanate (1 82 mg, 0.97 mmol) were coupled to form the desired urea (278 mg, 70%). 1H NMR (MeOD-d₄): δ 8.29 (d, 1H), 8.06 (d, 1H), 7.24 (m, 2H), 7.05 (d, 1H), 3.07 (t, 2H), 2.48 (t, 2H), 1.98 (s, 3H) 1.74 (m, 2H).

N-[4-chloro-2-hydroxy-3-[N"-[3-(methylsulfonyl)propyl]aminosulfonyl]phenyl]-N'-(2,3-dichlorophenyl) urea A solution of N-[4-chloro-2-hydroxy-3-[N"-(3-methylthiopropyl)aminosulfonyl]-phenyl]-N'-(2,3-dichlorophenyl) urea (50 mg, 0.11mmol) and oxone (93 mg, 0.15 mmol) in acetonitrile (13 mL) and water (7 mL) was stirred for 3 days at room temperature. The mixture was diluted with ethyl acetate and washed with water to give the crude material. Purification by column chromatography on silica gel, eluting with ethyl acetate/hexane/acetic acid (49/50/1, v/v/v), followed by recrystallization from acetone and hexane, gave the desired product (46 mg, 87%). EI-MS (m/z) 527.53, 529.57, 531.55 (M⁺).

N-[4-chloro-2-hydroxy-3-[N"-[3-(methylsulfinyl)propyl]aminosulfonyl]phenyl]-N'-(2,3-dichlorophenyl) urea A solution of N-[4chloro-2-hydroxy-3-[N"-(3-methylthiopropyl)aminosulfonyl]-phenyl]-N'-(2,3-dichlorophenyl) urea (50 mg, 0.10 mmol) and sodium periodate (26 mg, 0.12mmol) in acetonitrile (6 mL) and water (2 mL) was stirred for 3 days at room temperature. The mixture was diluted with ethyl acetate and washed with water to give the crude material. Recrystallization from acetone and hexane gave the desired product (42 mg, 81%). ¹H NMR (DMSO-d₆): δ 9.32 (s, 1H), 9.27 (s, 1H), 8.59 (s, 1H), 8.29 (d, 1H), 8.07 (m, 1H), 7.33 (m, 2H), 7.13 (d, 1H), 3.00 (m, 2H), 2.75 (m, 1H), 2.65 (m, 1H), 2.47 (s, 3H), 1.79 (m, 2H).

Example 44, 52 and 61

Preparation of N-(2-bromophenyl)-N'-[4-chloro-2-hydroxy-3-[N"-(3-methylthiopropyl)aminosulfonyl] phenyl] urea, N-(2-bromophenyl)-N'-[4-chloro-2-hydroxy-3-[N"-[3-(methylsulfonyl)propyl]-aminosulfonyl]phenyl] urea and N-(2-bromophenyl)-N'-[4-chloro-2-hydroxy-3-[N"-[3-(methylsulfinyl)propyl]aminosulfonyl]phenyl] urea N-(2-bromophenyl)-N'-[4-chloro-2-hydroxy-3-[N"-(3-methylthiopropyl)-aminosulfonyl]phenyl] urea Following the general procedure for urea formation outlined in example 15, N-(3-methylthiopropyl)-3-amino-6-chloro-2-hydroxybenzenesulfonamide (250 mg, 0.80 mmol) and 2-bromophenylisocyanate (191 mg, 0.97 mmol) were coupled to form the desired urea (300 mg, 74%). ¹H NMR (MeOD-d₄): δ 8.28 (d, 1H), 7.91 (d, 1H), 7.58 (d, 1H), 7.32 (t, 1H), 7.05 (d, 1H), 7.00 (t, 1H), 3.08 (t, 2H), 2.48 (t, 2H), 1.98 (s, 3H), 1.74 (m, 2H).

N-(2-bromophenyl)-N'[4-chloro-2-hydroxy-3-[N"-[3-(methylsulfonyl)propyl]-aminosulfonyl]phenyl] urea Following the oxidation procedure outlined in example 51, N-(2-bromophenyl)-N'-[4-chloro-2-hydroxy-3-[N"-(3-methylthiopropyl)aminosulfonyl]phenyl] urea (50 mg, 0.10 mmol) and oxone (91 mg, 0.15 mmol) were reacted to give the desired product (41 mg, 77%). Element Analysis Fond: C 37.58%, H 3.37%, N 7.59%, Theory: C 37.75%, H 3.54%, N 7.77%.

N-(2-bromophenyl)-N'4-chloro-2-hydroxy-3-[N"-[3-(methylsulfinyl)propyl]-aminosulfonyl]phenyl] urea Following the oxidation procedure outlined in example 61, N-(2-bromophenyl)-N'-[4-chloro-2-hydroxy-3-[N"-(3-methylthiopropyl)-aminosulfonyl]phenyl] urea (50 mg, 0.12 mmol) and sodium periodate (25 mg, 0.12 mmol) were reacted to give the desired product (8 mg, 16%). LC-MS 526.0 (M⁺).

Example 47, 58, 48 and 59

Preparation of N-(2-bromophenyl)-N'-[4-chloro-3-[N",N"-di-(2-methoxyethyl)aminosulfonyl]-2-hydroxyphenyl] urea, N-(2-bromophenyl)-N'-[4-chloro-3-[N",N"-di-(2-hydroxyethyl)aminosulfonyl]-2-hydroxyphenyl] urea, N-[4-chloro3-[N",N"-di-(2-methoxyethyl)-aminosulfonyl]-2-hydroxyphenyl]N'-(2,3-dichlorophenyl) urea and N-[4-chloro-3-[N",N"-di-(2-hydroxyethyl)aminosulfonyl]-2-hydroxyphenyl]-N'-(2,3-dichlorophenyl) urea N,N-di-(2-methoxyethyl)-2,6-dichloro-3-nitrobenzenesulfonamide Following the general procedure for sulfonamide formation outlined in example 15, 2,6-dichloro-3-nitrobenzenesulfonyl chloride (1.82 g, 6.26 mmol), bis(2-methoxyethyl)amine (830 mg, 6.26 mmol) and triethylamine(1.7mL, 12.52 mmol) were reacted to form the desired product (2.16 g, 89%). LC-MS (m/z) 387.2 ($M^+$).

N,N-di-(2-methoxyethyl)-6-chloro-2-hydroxy-3-nitrobenzenesulfonamide

Following the general hydrolysis procedure outlined in example 15, N,N-di-(2-methoxyethyl)-2,6-dichloro-3-nitrobenzenesulfonamide (800 mg, 2.07 mmol), 60% NaH (248 mg, 6.21 mmol) and water (45 μL, 2.48 mmol) were reacted to form the desired product (420 mg, 55%). EI-MS (m/z) 366.89, 368.81 ($M^-$).

N,N-di-(2-methoxyethyl)-3-amino-6-chloro-2-hydroxybenzenesulfonamide

Following the general hydrogenation procedure outlined in example 15, N,N-di-(2-methoxyethyl)-6chloro-2-hydroxy-3-nitrobenzenesulfonamide (100 mg, 0.27mmol) was reduced with hydrogen and 10% Pd/C (50 mg) to form the desired product (80 mg, 87%). $^1$H NMR (MeOD-$d_4$): δ 6.85 (m, 2H), 3.58 (t, 4H), 3.47 (t, 4H), 3.21 (s, 6H).

N-(2-bromophenyl)-N'4-chloro-3-[N",N"-di-(2-methoxyethyl)aminosulfonyl]-2-hydroxyphenyl] urea Following the general procedure for urea formation outlined in example 15, N,N-di-(2-methoxyethyl)-3-amino-6-chloro-2-hydroxybenzenesulfonamide (40 mg, 0.12 mmol) and 2-bromophenylisocyanate (23 mg, 0.12 mmol) were coupled to form the desired urea (39 mg, 61%). EI-MS (m/z) 534.6, 536.6 ($M^-$)

N-(2-bromophenyl)-N'-[4-chloro-3-[N",N"-di-(2-hydroxyethyl)aminosulfonyl]-2-hydroxyphenyl] urea A solution of N-(2-bromophenyl)-N'[4-chloro-3-[N",N"-di-(2-methoxyethyl)-aminosulfonyl]-2-hydroxyphenyl] urea (9.9 mg, 0.018 mmol) and aluminum bromide (4.2 mg, 0.018 mmol) in 2 mL of ethanethio was stirred for 16 hours at room temperature. The mixture was concentrated. The residue was diluted with ethyl acetate, then washed with 1 N aq. HCl, the organic layer was dried over $MgSO_4$ and concentrated. Recrystallization from acetone and methanol gave the desired product (4 mg, 44%). $^1$H NMR (MeOD-$d_4$): δ 8.30 (d, 1H), 7.92 (d 1H), 7.59 (d, 1H), 7.33 (t, 1H), 7.07 (d, 1H), 7.01 (t, 1H), 3.68 (t, 414), 3.51 (m, 4H).

N-[4-chloro-3-[N",N"-di-(2-methoxyethyl)aminosulfonyl]-2-hydroxyphenyl]-N'(2,3-dichlorophenyl) urea Following the general procedure for urea formation outlined in example 15, N,N-di-(2-methoxyethyl)-3-amino-6-chloro-2-hydroxybenzenesulfonamide (40 mg, 0.12 mmol) and 2,3-dichlorophenylisocyanate (22mg, 0.12 mmol) were coupled to form the desired urea (55 mg, 87%). $^1$H NMR (MeOD-$d_4$): 8δ 8.27 (m, 1H), 8.03 (m, 1H), 7.23 (m, 2H), 7.03 (m, 1H), 3.61 (m, 4H), 3.45 (m, 4H), 3.23 (s, 6H).

N-[4chloro-3-[N",N"-di-(2-hydroxyethyl)aminosulfonyl]-2-hydroxyphenyl]-N'-(2,3-dichlorophenyl) urea Following the deprotection procedure outlined in example 58, N-[4-chloro-3-[N",N"-di-(2-methoxyethyl)aminosulfonyl]-2-hydroxyphenyl]-N'(2,3-dichlorophenyl) urea (15 mg, 0.028 mmol) and aluminum bromide (18.7 mg, 0.07 mmol) were reacted to give the desired product (2 mg, 14%). LC-MS 500.0 ($M^+$).

Example 49 and 50

Preparation of N-(2-bromophenyl)-N'-[4-chloro-3-[N'-[2-(dimethylamino)ethyl]aminosulfonyl]-2-hydroxyphenyl] urea hydrochloride and N-[4-chloro-3-[N"-[2-(dimethylamino)ethyl)-aminosulfonyl]-2-hydroxyphenyl]-N'-(2,3-dichlorophenyl) urea hydrochloride N-[2-(dimethylamino)ethyl]-2,6-dichloro-3-nitrobenzenesulfonamide Following the general procedure for sulfonamide formation outlined in example 15, 2,6-dichloro-3-nitrobenzenesulfonyl chloride (400 mg, 1.38 mmol), N,N-dimethylethylenediamine (121 mg, 1.38 mmol) and triethylamine(0.39mL, 2.76 mmol) were reacted to form the crude product (480 mg) which was carried on to the hydrolysis without purification.. EI-MS (m/z) 341.88 ($M^-$).

N-[2-(dimethylamino)ethyl]-6-chloro-2-hydroxy-3-nitrobenzenesulfonamide

Following the general hydrolysis procedure outlined in example 15, crude N-[2-(dimethylamino)ethyl]-2,6-dichloro-3-nitrobenzenesulfonamide (480 mg), 60% NaH (168 mg, 4.2 mmol) and water (25 μL, 1.4 mmol) were reacted. The crude product (80 mg) was carried on to the next step without purification. EI-MS (m/z) 321.98, 323.96 ($M^-$).

N-[2-(dimethylamino)ethyl]-3-amino-6-chloro-2-hydroxybenzenesulfonamide

Following the general hydrogenation procedure outlined in example 15, crude N-[2-(dimethylamino)ethyl]-6-chloro-2-hydroxy-3-nitrobenzenesulfonamide (80 mg) was reduced with hydrogen and 10% Pd/C (40 mg) to form the crude product (70 mg) which was carried on to form urea without purification.

N-(2-bromophenyl)-N'-4-chloro-3-[N"-[2(dimethylamino)ethyl]aminosulfonyl]-2-hydroxyphenyl] urea hydrochloride Following the general procedure for urea formation outlined in example 15, crude N-2-(dimethylamino)ethyl]-3-amino-6-chloro-2-hydroxybenzenesulfonamide (35 mg) and 2-bromophenylisocyanate (28 mg, 0.14mmol) were coupled to form the desired urea (12 mg, 20% for four steps). EI-MS (m/z) 490.7, 492.7, 494.7 ($M^+$).

N-[4-chloro-3-[N"-[2-(dimethylamino)ethyl]aminosulfonyl]-2-hydroxyphenyl]-N'-(2,3-dichlorophenyl) urea hydrochloride Following the general procedure for urea formation outlined in example 15, crude N-2-(dimethylamino)ethyl]-3-amino-6-chloro-2-hydroxybenzenesulfonamide (35 mg) and 2,3-dichlorophenylisocyanate (26 mg, 0.1 4 mmol) were coupled to form the desired urea (5.8 mg, 10% for four steps). EI-MS (m/z) 482.80, 484.78 ($M^+$).

Example 53, 54 and 55

Preparation of N-[4-chloro-2-hydroxy-3-[N"-[2-(morpholinyl)ethyl]aminosulfonyl]phenyl]-N'-(2,3-dichlorophenyl) urea hydrochloride, N-[4-chloro-2-hydroxy-3-[N"-[2-(morpholinyl)ethyl]-aminosulfonyl]phenyl]-N'-(2-chlorophenyl) urea hydrochloride and N-(2-bromophenyl)-N'-[4-chloro-2-hydroxy-3-[N"-[2-(4-morpholinyl)ethyl]-aminosulfonyl]phenyl] urea N-[2-(morpholinyl)ethyl]-2,6-dichloro-3-nitrobenzenesulfonamide Following the general procedure for sulfonamide formation outlined in example 15, 2,6-dichloro-3- nitrobenzenesulfonyl chloride (600 mg, 2.07 mmol), 4-(2-aminoethyl) morpholine (269 mg, 2.07 mmol) and triethylamine (0.58mL, 4.13 mmol) were reacted to form the desired product (593 mg, 75%). LC-MS (m/z) 384.0 (M+).

N-(2-(morpholinyl)ethyl]-6-chloro-2-hydroxy-3-nitrobenzenesulfonamide

Following the general hydrolysis procedure outlined in example 15, N-[2-(morpholinyl)ethyl]-2,6-dichloro-3-nitrobenzenesulfonamide (400 mg, 1.04 mmol), 60% NaH (125 mg, 3.12 mmol) and water (23 μL, 1.25 mmol) were reacted to form the crude product (600 mg) which was carried onto the hydrogenation without purification. EI-MS (m/z) 363.95, 365.94 (M−).

N-[2-(morpholinyl)ethyl]-3-amino-6-chloro-2-hydroxybenzenesulfonamide

Following the general hydrogenation procedure outlined in example 15, crude N-[2-(morpholinyl)ethyl]-6-chloro-2-hydroxy-3-nitrobenzenesulfonamide (300 mg) was reduced with hydrogen and 10% Pd/C (80 mg) to form the crude product (300 mg) which was carried onto the urea step without purification. EI-MS (m/z) 338.93, 340.98 (M+).

N-[4-chloro-2-hydroxy-3-[N"-[2-(morpholinyl)ethyl] aminosulfonyl]phenyl]-N'(2,3-dichlorophenyl) urea hydrochloride Following the general procedure for urea formation outlined in example 15, crude N-[2-(morpholinyl)ethyl]-3-amino-6-chloro-2-hydroxybenzenesulfonamide (115 mg) and 2,3-dichlorophenylisocyanate (49 mg, 0.26mmol) were coupled to form the desired urea (23 mg, 15% for 3 steps). EI-MS (m/z) 522.72, 524.65, 526.70 (M+).

N-[4-chloro-2-hydroxy-3-[N"-[2-(morpholinyl)ethyl] aminosulfonyl]phenyl]-N'(2-chlorophenyl) urea hydrochloride Following the general procedure for urea formation outlined in example 15, crude N-[2-(morpholinyl)ethyl]-3-amino-6-chloro-2-hydroxybenzenesulfonamide (183 mg) and 2-chlorophenylisocyanate (40 mg, 0.26 mmol) were coupled to form the desired urea (50 mg, 39% for 3 steps). LC-MS 489.2 (M+).

N-(2-bromophenyl)-N'-[4-chloro-2-hydroxy-3-[N"-[2-(4-morpholinyl)ethyl]aminosulfonyl]phenyl] urea Following the general procedure for urea formation outlined in example 15, N-[2-(morpholinyl)ethyl]-3-amino-6-chloro-2-hydroxybenzenesulfonamide (150 mg) and 2-bromophenylisocyanate (51 mg, 0.26 mmol) were coupled to form the desired urea (10 mg, 7% for 3 steps). EI-MS (m/z) 535.64, 537.56, 539.61 (M+).

Example 56 and 57

Preparation of N-[4-chloro-2-hydroxy-3-(4-thiomorpholinylsufonyl)phenyl]-N'-(2,3-dichlorophenyl) urea and N-(2-bromophenyl)-N'-[4chloro-2-hydroxy-3-(4-thiomorpholinylsufonyl) phenyl] urea 2,6-dichloro-3-nitro-1-(4-thiomorpholinylsufonyl)benzene Following the general procedure for sulfonamide formation outlined in example 15, 2,6-dichloro-3-nitrobenzenesulfonyl chloride (2.0 g, 6.88mmol), thiomorpholine (710 mg, 6.88 mmol) and triethylamine(1.92mL, 13.76mmnol) were reacted to form the desired product (2.30 g, 94%). $^1$H NMR (MeOD-d$_4$): δ 7.95 (d, 1H), 7.85(d, 1H), 3.68 (t, 4H), 2.69 (t, 4H).

6-chloro-2-hydroxy-nitro-1-(4-thiomorpholinylsufonyl) benzene

Following the general hydrolysis procedure outlined in example 15, 2,6-dichloro-3-nitro-1-(4-thiomorpholinylsufonyl)benzene (1.04 g, 2.91 mmol), 60% NaH (349 mg, 8.73 mmol) and water (63 μL, 3.50 mmol) were reacted to form the desired product (330 mg, 33%). EI-MS (m/z) 336.89, 338.93 (M−).

4chloro-2-hydroxy-3-(4-thiomorpholinylsufonyl)aniline

Following the general hydrogenation procedure outlined in example 15, 6-chloro-2-hydroxy-3-nitro-1-(4-thiomorpholinylsufonyl)benzene (330 mg, 0.97 mmol) was reduced with hydrogen and 10% Pd/C (150 mg) to form the desired product (240 mg, 80%). $^1$H NMR (MeOD-d$_4$): δ 7.08 (d, 1H), 6.98(d, 1H), 3.59 (t, 4H), 2.68 (t, 4H).

N-[4-chloro-2-hydroxy-3-(4-thiomorpholinylsufonyl) phenyl]-N'-(2,3-dichlorophenyl) urea Following the general procedure for urea formation outlined in example 15, 4-chloro-2-hydroxy-3-(4-thiomorpholinylsufonyl)aniline (120 mg, 0.36 mmol) and 2,3-dichlorophenylisocyanate(68 mg, 0.36 mmol) were coupled to form the desired urea (50 mg, 28%). $^1$H NMR (MeOD-d$_4$): δ 8.31 (m, 1H), 8.05 (m, 1H), 7.26 (m, 2H), 7.08 (m, 1H), 3.61 (m, 4H), 2.69 (m, 4H).

N-(2-bromophenyl)-N'-[4-chloro-2-hydroxy-3-(4-thuomorpholinylsulfonyl)-phenyl] urea Following the general procedure for urea formation outlined in example 15, 4-chloro-2-hydroxy-3-(4-thiomorpholinylsufonyl)aniline (120 mg, 0.26 mmol) and 2-bromophenylisocyanate (72 mg, 0.36 mmol) were coupled to form the desired urea (110 mg, 60%). $^1$H NMR (DMSO-d$_6$): δ 9.25 (s, 1H), 8.98 (s, 1H), 8.34 (d, 1H), 7.92 (d, 1H), 7.65 (d, 1H) 7.35 (t, 1H), 7.19 (d, 1H), 7.01 (t, 1H), 3.54 (t, 4H), 2.67 (t, 4H).

Example 45

N-(4-chloro-2-hydroxy-3-aminosulfonylphenyl)-N'-(2,3-dichlorophenyl) urea potasium salt The general procedure outlined in example 15 was followed to give N-(4-chloro-2-hydroxy-3-aminosulfonylphenyl)-N'-(2,3-dichlorophenyl) urea potasium salt; $^1$H NMR (DMSO-d,): δ 9.27 (s, 2H), 8.01 (m, 3H), 7.81 (d, 1H), 7.26 (m, 2H), 6.15 (m, $^1$H).

Example 46

N-(4-chloro-2-hydroxy-3-aminosulfonylphenyl)-N'-(2,3-dichlorophenyl) urea sodium salt The general procedure outlined in example 15 was followed to give N-(4-chloro-2-hydroxy-3-aminosulfonylphenyl)-N'-(2,3-dichlorophenyl) urea sodium salt; $^1$H NMR (DMSO-d$_6$): δ 9.27 (s, 2H), 8.01 (m, 3H), 7.77 (d, 1H), 7.26 (m, 2H), 6.05 (d, 1H).

Example 62, 67, 63 and 66

Preparation of N-(2-bromophenyl)-N'-[3-[N"-[(1-tert-butoxycarbonylpiperidin-4-yl)methyl] aminosulfonyl]-4-chloro-2-hydroxyphenyl] urea, N-(2-bromophenyl)-N'-[4-chloro-2-hydroxy-3-[N"-[(piperidin-4-yl)methyl]aminosulfonyl]phenyl] urea hydrochloride, N-[3-[N"-[(1-tert-butoxycarbonylpiperidin-4-yl)methyl] aminosulfonyl]-4-chloro-2-hydroxyphenyl]-N'-(2,3-dichlorophenyl) urea and N'-chloro-2-hydroxy-3-[N"-[(piperidin-4-yl)methyl]aminosulfonyl]phenyl]-N'-(2,3-dichlorophenyl) urea trifluoroacetate N-[(1-tert-butoxycarbonylpiperidin-4-yl)methyl]-2,6-dichloro-3-nitrobenzenesulfonamide Following the general procedure for sulfonamide formation outlined in example 15, 2,6-dichloro-3- nitrobenzenesulfonyl chloride (1.2 g, 4.13 mmol), N-(tert-butoxycarbonyl)4-aminomethyl piperidine (0.88 g, 4.13 mmol) and triethylamine(0.86mL, 6.20 mmol) were reacted to form the desired product (1.52 g, 79%). LC-MS (m/z) 468.2 (M$^+$).

N-[(1-tert-butoxycarbonylpiperidin4-yl)methyl]-6-chloro-2-hydroxy-3-nitrobenzenesulfonamide Following the general hydrolysis procedure outlined in example 15, N-[(1-tert-butoxycarbonylpiperidin-4-yl) methyl]-2,6dichloro-3-nitrobenzenesulfonamide (800 mg, 1.89 mmol), 60% NaH (227 mg, 5.67 mmol) and water (41 μL, 2.27 mmol) were reacted to form the desired product (495 mg, 58%). EI-MS (m/z) 447.92, 449.84 (M$^-$).

N-[(1-tert-butoxycarbonylpiperidin-4-yl)methyl]-3-amino-6-chloro-2-hydroxybenzenesulfonamide Following the general hydrogenation procedure outlined in example 15, N-[(1-tert-butoxycarbonylpiperidin-4-yl) methyl]-6-chloro-2-hydroxy-3-nitrobenzenesulfonamide (480 mg, 1.07 mmol) was reduced with hydrogen and 10% Pd/C (240 mg). The crude product (460 mg) was carried on to the next step without purification. $^1$H NMR (MeOD-d$_4$): δ 6.86 (m, 2H), 4.00 (d, 2H), 2.83 (m, 2H), 2.78 (m, 2H), 1.60 (m, 3 H), 1.44 (s, 9H), 1.00 (m, 2H).

N-(2-bromophenyl)-N'-[3-[N"-[(I -tert-butoxycarbonylpiperidin-4-yl)methyl]aminosulfonyl]-4-chloro-2-hydroxyphenyl] urea Following the general procedure for urea formation outlined in example 15, crude N-[(1-tert-butoxycarbonylpiperidin-4-yl)methyl]-3-amino6-chloro-2-hydroxybenzenesulfonamide (230 mg) and 2-bromophenylisocyanate (129 mg, 0.65 mmol) were coupled to form the desired urea (110 mg, 30% for two steps). LC-MS (m/z) 619.0 (M$^+$).

N-(2-bromophenyl)-N'-[4-chloro-2-hydroxy-3-[N"-[(piperidin-4-yl)methyl]aminosulfonyl]phenyl] urea hydrochloride A solution of N-(2-bromophenyl)-N'-[3-[N"-[(1-tert-butoxycarbonylpiperidin-4-yl)methyl]aminosulfonyl]-4-chloro-2-hydroxyphenyl] urea (27 mg, 0.044 mmol) in 1.0 mL of 4.1 N HCl in 1,4-dioxane was stirred at room temperature for 10 min. The mixture was concentrated. Recrystallization from acetone and hexane gave desired product (16 mg, 65%). LC-MS (m/z) 519.2 (M$^+$).

N-[3-[N"-[(1-tert-butoxycarbonylpiperidin-4-yl)methyl] aminosulfonyl]4-chloro-2-hydroxyphenyl]-N'-(2,3-dichlorophenyl) urea Following the general procedure for urea formation outlined in example 15, crude N-[(1 -tert-butoxycarbonylpiperidin]yl)methyl]-3-amino-6chloro-2-hydroxybenzenesulfonamide (230 mg) and 2,3-dichlorophenylisocyanate (122 mg, 0.65 mmol) were coupled to form the desired urea (100 mg, 29% for two steps). $^1$H NMR (MeOD-d$_4$): δ 8.29 (d, 1H), 8.05 (m, 1H), 7.25 (m, 2H), 7.06 (d, 1H), 4.35 (d, 2H), 2.83 (m, 2H), 2.49 (mn, 2H), 1.69 (m, 3H), 1.43 (s, 9H), 1.00 (m, 2H).

N-[4-chloro-2-hydroxy-3-[N"-[(piperidin4-yl)methyl] aminosulfonyl]phenyl]-N'-(2,3-dichlorophenyl) urea trifluoroacetate Following the general procedure for Boc deprotection outlined in example 36, N-[3-[N"-[(1-tert-butoxycarbonylpiperidin4-yl)methyl]aminosulfonyl]-4-chloro-2-hydroxyphenyl]-N'-(2,3-dichlorophenyl) urea (20 mg, 0.033 mmol) was stirred in trifluoroacetic acid to form the desired product (9 mg, 44%). LC-MS (m/z) 509.0 (M$^+$).

Example 64, 140, 65 and 141

Preparation of N-[4-chloro-2-hydroxy-3-(1-oxidothiomorpholinosulfonyl)phenyl]-N'-(2,3-dichlorophenyl) urea, N-[4-chloro-2-hydroxy-3-(1-oxidothiomorpholinosulfonyl)phenyl]-N'(2,3-dichlorophenyl) urea sodium salt, N-(2-bromophenyl)-N'-[4-chloro-2-hydroxy-3-(1-oxidothiomorpholinosulfonyl)phenyl] urea and N'-4-chloro-2-hydroxy-3-(1-oxidothiomorpholinosulfonyl)phenyl]-N'-(2-chlorophenyl) urea 6-chloro-2-hydroxy-3-nitro-1-(1-oxidothiomorpholinosulfonyl)benzene A solution of 6-chloro-2-hydroxy-3-nitro-]-(4-thiomorpholinylsufonyl)benzene (100 mg, 0.30 mmol) and sodium periodate (95 mg, 0.44 mmol) in acetonitrile (100 mL) and water (2 ML) was stirred for 3 days at room temperature. The mixture was diluted with ethyl acetate and washed with water, dried over MgSO$_4$ and concentrated to give the desired product (106.4 mg, 100%). EI-MS (m/z) 352.89, 354.87 (M$^-$).

4-chloro-2-hydroxy-3-(1 -oxidothiomorpholinosulfonyl) aniline

Following the general hydrogenation procedure outlined in example 15, 6-chloro-2-hydroxy-3-nitro- 1-(1-oxidothiomorpholinosulfonyl)benzene (103 mg, 0.29mmol) was reduced with hydrogen and 10% Pd/C (59 mg) to form the desired product (89 mg, 95%). LC-MS (m/z) 325.0 (M$^+$).

N-[4-chloro2-hydroxy-3-(1 -oxidothiomorpholinosulfonyl) phenyl]-N'-(2,3-dichlorophenyl) urea Following the general procedure for urea formation outlined in example 15, 4-chloro-2-hydroxy-3-(1-oxidothiomorpholinosulfonyl)aniline (117 mg, 0.35 mmol) and 2,3-dichlorophenylisocyanate (72 mg, 0.38 mmol) were coupled to form the desired urea (79 mg, 44%). $^1$H NMR (DMSO-d$_6$): δ 9.34 (s, 1H), 9.27 (s, 1H), 8.28 (d, 1H), 8.05 (m, 1H), 7.32 (m, 2H), 7.21 (d, 1H), 3.75 (m, 2H), 3.65 (m, 2H), 2.89, (m, 4H).

N-[4-chloro-2-hydroxy-3-(1-oxidothiomorpholinosulfonyl) phenyl]-N'-(2,3-dichlorophenyl) urea sodium salt Following the general procedure for salt formation outlined in example 15, N-[4-chloro-2-hydroxy-3-(1-oxidothiomorpholinosulfonyl)phenyl]-N'-(2,3-dichlorophenyl) urea (275 mg, 0.53 mmol) and 0.50 N aq. NaOH (1.06mL, 0.53mmol) was reacted to give the desired sodium slat (250 mg, 87%). $^1$H NMR (DMSO-d$_6$): δ 9.30 (s, 2H), 8.00 (d, 1H), 7.67 (d, 1H), 7.25 (m, 2H), 5.89 (d, 1H), 3.68 (m., 4H), 2.90 (t, 2H), 2.75 (t, 3H).

N-(2-bromophenyl)-N'-[4-chloro-2-hydroxy-3-(1-oxidothiomorpholinosulfonyl)-phenyl] urea Following the general procedure for urea formation outlined in example 15, 4-chloro-2-hydroxy-3-(1-oxidothiomorpholinosulfonyl)aniline (88 mg, 0.27 mmol) and 2-bromophenylisocyanate (65 mg, 0.33 mmol) were coupled to form the desired urea (65 mg, 46%). LC-MS (m/z) 524.2 (M$^+$).

N-[4-chloro-2-hydroxy-3-(1-oxidothiomorpholinosulfonyl) phenyl]-N'-(2-chlorophenyl) urea Following the general procedure for urea formation outlined in example 15, 4-chloro-2-hydroxy-3-(1-oxidothiomorpholinosulfonyl)aniline (117 mg, 0.35 mmol) and 2-chlorophenylisocyanate (58 mg, 0.28mmol) were coupled to form the desired urea (58 mg, 35%). LC-MS (m/z) 478.0 (M$^+$).

Example 68, 69 and 70

Preparation of N-[3-(1-azetidinylsulfonyl)4-chloro-2-hydroxyphenyl]-N'-(2-bromophenyl) urea, N-[3-(1-azetidinylsulfonyl)-4-chloro-2-hydroxyphenyl]-N'-(2-chlorophenyl) urea and N-[3-(1-azetidinylsulfonyl)-4-chloro-2-hydroxyphenyl]-N'-(2,3-dichlorophenyl) au urea 1-(azetidin-1-yl)sulfonyl-2,6-dichloro-3-nitrobenzene Following the general procedure for sulfonamide formation outlined in example 15, 2,6-dichloro-3-nitrobenzenesulfonyl chloride (1.0 g, 3.44 mmol), azetidine hydrochloride (320 mg, 3.44 mmol) and triethylamine (1.44mL, 10.32 mmol) were reacted to form the desired product (510 mg, 48%). $^1$H NMR (MeOD-d$_4$): δ 7.94 (d, 1H), 7.79 (d, 1H), 4.16 (t, 4H), 2.29 (m, 2H).

1-(azetidin-1-yl)sulfonyl-6-chloro-2-hydroxy-3-nitrobenzene

Following the general hydrolysis procedure outlined in example 15, 1-(azetidin-1-yl)sulfonyl-2,6-dichloro-3-nitrobenzene (510 mg, 1.64mmol), 60% NaH (197 mg, 4.92 mmol) and water (35 μL, 1.97 mmol) were reacted to form the desired product (240 mg, 50%). $^1$H NMR (MeOD-d$_4$): δ 8.09 (d, 1H), 7.25 (d, 1H), 4.15 (t, 4H), 2.29 (m, 2H).

3-(azetidin-1-yl)sulfonyl-4-chloro-2-hydroxyaniline

Following the general hydrogenation procedure outlined in example 15, 1-(azetidin-1-yl)sulfonyl-6-chloro-2-hydroxy-3-nitrobenzene (240 mg, 0.82 mmol) was reduced with hydrogen and 10% Pd/C (110 mg) to form the desired product (215 mg, 100%). 1H NMR (MeOD-d$_4$): δ 6.91 (m, 2H), 4.01 (t, 4H), 2.23 (m, 2H).

N-[3-(1-azetidinylsulfonyl)4-chloro-2-hydroxyphenyl]-N'-(2-bromophenyl) urea Following the general procedure for urea formation outlined in example 15, 3-(azetidin-1-yl)sulfonyl-4-chloro-2-hydroxyaniline (215 mg, 0.82 mmol) and 2-bromophenylisocyanate (195 mg, 0.98 mmol) were coupled to form the desired urea (69 mg, 18%). LC-MS 462.0 (M$^+$).

N-[3-(1-azetidinylsulfonyl)-4-chloro-2-hydroxyphenyl]-N'-(2-chlorophenyl) urea

Following the general procedure for urea formation outlined in example 15, 3-(azetidin- 1-yl)sulfonyl-4-chloro-2-hydroxyaniline (235 mg, 0.9 mmol) and 2-chlorophenylisocyanate (1 34 mg, 0.9 mmol) were coupled to form the desired urea (200 mg, 54%). LC-MS 416.0 (M$^+$).

N-3-(1-azetidinylsulfonyl)4-chloro-2-hydroxyphenyl]-N'-(2,3-dichlorophenyl) urea Following the general procedure for urea formation outlined in example 15, 3-(azetidin-1-yl)sulfonyl-4-chloro-2-hydroxyaniline (235 mg, 0.9 mmol) and 2,3-dichlorophenylisocyanate (169 mg, 0.9 mmol) were coupled to form the desired urea (160 mg, 40%). LC-MS 450.0 (M$^+$).

Example 71

N-(2-bromophenyl)-N'-[4-chloro-3-(N",N"-dimethylaminosulfonyl)-2-hydroxyphenyl] urea potassium salt The general procedure outlined in example 15 was followed to give N-(2-bromophenyl)-N'-[4-chloro-3-(N",N"-dimethylaminosulfonyl)-2-hydroxyphenyl] urea potassium salt; $^1$H NMR (DMSO-d$_6$): δ 9.20 (s, 1H), 8.99 (s, 1H), 7.82 (d, 1H), 7.66 (d, 1H), 7.57 (d, 1H), 7.29 (t, 1H), 6.95 (t, 1H), 5.93 (d, 1H), 2.83 (s, 6H).

Example 72

N-(2-bromophenyl)-N'-[4-chloro-3-(N",N"-dimethylaminosulfonyl)-2-hydroxyphenyl] urea sodium salt The general procedure outlined in example 15 was followed to give N-(2-bromophenyl)-N'-[4-chloro-3-(N",N"-dimethylaminosulfonyl)-2-hydroxyphenyl] urea sodium salt; Element Analysis Theory (1.25 eq. water): C 36.53%, H 3.37%, N 8.52%, Na 4.66%, Found: C 36.32%, H 3.34%, N 8.38%, Na 4.69%.

Example 73, 74 and 75

Preparation of N-(2-bromophenyl)-N'-[4-chloro-3-(N"-cyclopropylaminosulfonyl)-2-hydroxyphenyl) urea, N-[4-chloro-3-(N"-cyclopropylaminosulfonyl)-2-hydroxyphenyl]-N'-(2-chlorophenyl) urea and N-[4-chloro-3-(N"-cyclopropylaminosulfonyl)-2-hydroxyphenyl]-N'-(2,3-dichlorophenyl) urea N-cyclopropyl-2,6-dichloro-3-nitrobenzenesulfonamide Following the general procedure for sulfonamide formation outlined in example 15, 2,6-dichloro-3-nitrobenzenesulfonyl chloride (1.39 g, 4.78 mmol), cyclopropylamine (273 mg, 4.78 mmol) and triethylamine(1.0 mL, 7.17 mmol) were reacted to form the desired product (1.15 g, 77%). $^1$H NMR (MeOD-d$_4$): δ 7.72 (d, 1H), 7.65 (d, 1H), 2.34 (m, 1H), 0.75 (m, 4H).

N-cyclopropyl-6-chloro-2-hydroxy-3-nitrobenzenesulfonamide

Following the general hydrolysis procedure outlined in example 15, N-cyclopropyl-2,6-dichloro-3-nitrobenzenesulfonamide (1.15 g, 3.70 mmol), 60% NaH (444 mg, 11.1 mmol) and water (67 μL, 3.70 mmol) were reacted to form the desired product (740 mg, 68%). $^1$H NMR (MeOD-d$_4$): δ 8.06 (d, 1H), 7.24 (d, 1H), 2.29 (m, 1H), 0.60 (m, 4H).

N-cyclopropyl-3-amino-6-chloro-2-hydroxybenzenesulfonamide

Following the general hydrogenation procedure outlined in example 15, N-cyclopropyl-6-chloro-2-hydroxy-3-nitrobenzenesulfonamide (740 mg, 2.53 mmol) was reduced with hydrogen and 10% Pd/C (350 mg) to form the desired product (660 mg, 99%). $^1$H NMR (MeOD-d$_4$): δ 6.83 (m, 2H), 2.20 (m, 1H), 0.56 (m, 4H).

N-(2-bromophenyl)-N'-chloro-3-(N"-cyclopropylaminosulfonyl)-2-hydroxyphenyl) urea Following the general procedure for urea formation outlined in example 15, N-cyclopropyl-3-amino-6-chloro-2-hydroxybenzenesulfonamide (220 mg, 0.84 mmol) and 2-bromophenylisocyanate (199 mg, 1.01 mmol) were coupled to form the desired urea (135 mg, 35%). LC-MS (m/z) 462.0 (M$^+$).

N-[4-chloro-3-(N"-cyclopropylaminosulfonyl)-2-hydroxyphenyl]-N'-(2-chlorophenyl) urea Following the general procedure for urea formation outlined in example 15, N-cyclopropyl -3-amino-6-chloro-2-hydroxybenzenesulfonamide (220 mg, 0.84 mmol) and 2-chlorophenylisocyanate (155 mg, 1.01 mmol) were coupled to form the desired urea (150 mg, 43%). LC-MS (m/z) 416.2 (M$^+$).

N-[4-chloro-3-(N"-cyclopropylaminosulfonyl)-2-hydroxyphenyl]-N'(2,3-dichlorophenyl) urea Following the general procedure for urea formation outlined in example 15, N-cyclopropyl-3-amino-6-chloro-2-hydroxybenzenesulfonamide (220 mg, 0.84 mmol) and 2,3-dichlorophenylisocyanate (190 mg, 1/01 mmol) were coupled to form the desired urea (176 mg, 46%). LC-MS (m/z) 452.0 (M$^+$).

Example 76, 77 and 78

Preparation of N-(2-bromophenyl)-N'-[4-chloro-2-hydroxy-3-(N''-propylaminosulfonyl)phenyl] urea, N-[4-chloro-2-hydroxy-3-(N''-propylaminosulfonyl)phenyl]-N'-(2,3-dichlorophenyl) urea and N-[4-chloro-2-hydroxyl-3-(N''-propylaminosulfonyl)phenyl]-N'-(2-chlorophenyl) urea N-propyl-2,6-dichloro-3-nitrobenzenesulfonamide Following the general procedure for sulfonamide formation outlined in example 15, 2,6-dichloro-3-nitrobenzenesulfonyl chloride (1.3 g, 4.48 mmol), propylamine (264 mg, 4.48 mmol) and triethylamine(0.94mL, 6.72 mmol) were reacted to form the desired product (10 g, 71%). $^1$H NMR (MeOD-d$_4$): δ7.92 (d, 1H), 7.78 (d, 1H), 3.00 (t, 2H), 1.50 (m, 2H), 0.88 (t, 3H).

N-propyl-6-chloro-2-hydroxy-3-nitrobenzenesulfonamide

Following the general hydrolysis procedure outlined in example 15, N-propyl-2,6-dichloro-3-nitrobenzenesulfonamide (1.0 , 3.19mmol), 60% NaH (393 mg, 3.19 mmol) and water (58 μL, 3.19 mmol) were reacted to form the desired product (650 mg, 69%). LC-MS (m/z) 295.0 (M$^+$).

N-propyl-3-amino-6-chloro-2-hydroxybenzenesulfonamide

Following the general hydrogenation procedure outlined in example 15, N-propyl-6chloro-2-hydroxy-3-nitrobenzenesulfonamide (650 mg, 2.2 mmol) was reduced with hydrogen and 10% Pd/C (320 mg) to form the desired product (560 mg, 96%). $^1$H NMR (MeOD-d$_4$): δ 6.83 (m, 1H), 2.86 (t, 2H), 1.50 (m, 2H), 0.87 (t, 3H).

N-(2-bromophenyl)-N'[4-chloro-2-hydroxy-3-(N''-propylaminosulfonyl)phenyl] urea

Following the general procedure for urea formation outlined in example 15, N-propyl-3-amino-6-chloro-2-hydroxybenzenesulfonamide (186 mg, 0.71 mmol) and 2-bromophenylisocyanate (140 mg, 0.71 mmol) were coupled to form the desired urea (149 mg, 46%). LC-MS (m/z) 464.0 (M$^+$).

N-[4-chloro-2-hydroxy-3-(N''-propylaminosulfonyl)phenyl]-N'(2,3-dichlorophenyl) urea Following the general procedure for urea formation outlined in example 15, N-propyl-3-amino-6-chloro-2-hydroxybenzenesulfonamide (186 mg, 0.71 mmol) and 2,3-dichlorophenylisocyanate (133 mg, 0.71 mmol) were coupled to form the desired urea (259 mg, 81%). LC-MS (m/z) 452.0 (M$^+$).

N-[4-chloro-2-hydroxyl-3-(N''-propylaminosulfonyl)phenyl]-N'(2-chlorophenyl) urea Following the general procedure for urea formation outlined in example 15, N-propyl-3-amino-6-chloro-2-hydroxybenzenesulfonamide (186 mg, 0.71 mmol) and 2-chlorophenylisocyanate (108 mg, 0.71 mmol) were coupled to form the desired urea (148 mg, 50%). LC-MS (m/z) 418.2 (M$^+$).

Example 79, 80 and 81

Preparation of N-(2-bromophenyl)-N'-[4-chloro-3-(N''-ethylaminosulfonyl])-2-hydroxyphenyl] urea, N-[4-chloro-3-(N''-ethylaminosulfonyl)-2-hydroxyphenyl]-N'-(2-chlorophenyl) urea, and N-[4-chloro-3-(N''-ethylaminosulfonyl)-2-hydroxyphenyl]-N'-(2,3-dichlorophenyl) urea N-ethyl-2,6-dichloro-3-nitrobenzenesulfonamide Following the general procedure for sulfonamide formation outlined in example 15, 2,6-dichloro-3-nitrobenzenesulfonyl chloride (800 mg, 2.75 mmol), ethylamine (4.13 mL, 8.26 mmol) and triethylamine(1.5 mL, 8.36 mmol) were reacted to form the desired product (610 mg, 74%). $^1$H NMR (MeOD-d$_4$): δ 7.92 (d, 1H), 7.78 (d, 1H), 3.08 (q, 2H), 1.11 (t, 3H).

N-ethyl-6-chloro-2-hydroxy-3-nitrobenzenesulfonamide

Following the general hydrolysis procedure outlined in example 15, N-ethyl-2,6dichloro-3-nitrobenzenesulfonamide (1.16 g, 3.88mmol), 60% NaH (466 mg, 11.64 mmol) and water (70 μL, 3.88 mmol) were reacted. The crude product (1.34 g) was carried on to the next step without purification. $^1$H NMR (MeOD-d$_4$): δ 8.07 (d, 1H), 7.25 (d, 1H), 3.05 (q, 2H), 1.12 (t, 3H).

N-ethyl-3-amino-6-chloro-2-hydroxybenzenesulfonamide

Following the general hydrogenation procedure outlined in example 15, crude N-ethyl-6-chloro-2-hydroxy-3-nitrobenzenesulfonamide (1.34 g) was reduced with hydrogen and 10% Pd/C (400 mg) to form the desired product (800 mg, 82% for two steps). $^1$H NMR (MeOD-d$_4$): δ 6.85 (d, 1H), 6.78 (d, 1H), 2.85 (q, 2H), 0.95 (t, 3H).

N-(2-bromophenyl)-N'-[4-chloro-3-(N''-ethylaminosulfonyl])-2-hydroxyphenyl] urea Following the general procedure for urea formation outlined in example 15, N-ethyl-3-amino-6-chloro-2-hydroxybenzenesulfonamide (266 mg, 1.06 mmol) and 2-bromophenylisocyanate (211 mg, 1.06 mmol) were coupled to form the desired urea (211 mg, 44%). LC-MS (m/z) 450.0 (M$^+$).

N-[4-chloro-3-(N-ethylaminosulfonyl)-2-hydroxyphenyl]-N'(2-chlorophenyl) urea

Following the general procedure for urea formation outlined in example 15, N-ethyl-3-amino-6-chloro-2-hydroxybenzenesulfonamide (266 mg, 1.06 mmol) and 2-chlorophenylisocyanate (163 mg, 1.06 mmol) were coupled to form the desired urea (142 mg, 33%). LC-MS (m/z) 04.0 (M$^+$).

N-[4-chloro-3-(N''-ethylaminosulfonyl)-2-hydroxyphenyl]-N'(2,3-dichlorophenyl) urea Following the general procedure for urea formation outlined in example 15, N-ethyl-3-amino-6-chloro-2-hydroxybenzenesulfonamide (266 mg, 1.06 mmol) and 2,3-dichlorophenylisocyanate (200 mg, 1.06 mmol) were coupled to form the desired urea (193 mg, 41%). LC-MS (m/z) 440.0 (M$^+$).

Example 82 and 136

Preparation of N-(2-bromophenyl)-N'-[3-[N''-[5-(tert-butoxycarbonylamino)-5-carboxypentyl]aminosulfonyl]-4-chloro-2-hydroxyphenyl] urea and N-[3-[N''-(5-amino-5-carboxypentyl)-aminosulfonyl]-4-chloro-2-hydroxyphenyl]-N'-(2-bromophenyl) urea trifluoroacetate N-[5-(tert-butoxycarbonylamino)-5-metboxycarbonylpentyl]-2,6-dichloro-3-nitrobenzenesulfonamide Following the general procedure for sulfonamide formation outlined in example 15, 2,6-dichloro-3-nitrobenzenesulfonyl chloride (2.0 g, 6.88 mmol), Boc-Lys-OMe acetate (2.206 g, 6.88 mmol) and triethylamine(2.4 mL, 17.2 mmol) were reacted to form the desired product (1.25 g, 35%). $^1$H NMR (MeOD-d$_4$): δ 7.93 (d, 1H), 7.78 (d, 1H), 4.02 (m, 1H), 3.70 (s, 3H), 3.04 (t, 2H), 1.69 (m, 2H), 1.50 (m, 4H), 1.43 (s, 9H).

N-[5-(tert-butoxycarbonylamino)-5-carboxypentyl]-6-chloro-2-hydroxy-3-nitrobenzenesulfonamide Following the general hydrolysis procedure outlined in example 15, N-[5-(tert-butoxycarbonylamino)-5- methoxycarbonylpentyl]-2,6-dichloro-3-nitrobenzenesulfonamide (1.2 g, 2.33 mmol), 60% NaH (379 mg, 9.32mmol) and water (84 μL, 4.66 mmol) were reacted to form the desired product (850 mg, 76%). $^1$H NMR (MeOD-d$_4$): δ 8.05 (d, 1H), 7.22 (d, 1H), 4.00 (m, 1H), 3.01 (t, 2H), 1.72 (m, 2H), 1.50-1.65 (m, 4H), 1.44 (s, 9H).

N-[5-(tert-butoxycarbonylamino)-5-carboxypentyl]-3-amino-6-chloro-2-hydroxybenzenesulfonamide Following the general hydrogenation procedure outlined in example 15, N-[5-(tert-butoxycarbonylamino)-S-carboxypentyl]-6-chloro-2-hydroxy-3-nitrobenzenesulfonamide (204 mg, 0.42mmol) was reduced with hydrogen and 10% Pd/C (100 mg) to form the desired product (189 mg, 100%). $^1$H NMR (MeOD-d$_4$): δ 6.84 (in, I11), 4.08 (m, 1H), 2.92 (t, 2H), 1.75 (m, 2H), 1.55 (m, 4H), 1.44 (s, 9H).

N-(2-bromophenyl)-N'-[3-[N"-[5-(tert-butoxycarbonylamino)-5-carboxypentyl]aminosulfonyl]4-chloro-2-hydroxyphenyl] urea Following the general procedure for urea formation outlined in example 15, N-[5-(tert-butoxycarbonylamino)-5-carboxypentyl]-3-amino-6-chloro-2-hydroxybenzenesulfonamide (189 mg, 0.42 mmol) and 2-bromophenylisocyanate (84 mg, 0.42 mmol) were coupled to form the desired urea (20 mg, 7%). LC-MS (m/z) 651.2 (M$^+$).

N-N3-[N"-(5-amino-5-carboxypentyl)aminosulfonyl]-4-chloro-2-hydroxyphenyl]- N'(2-bromophenyl) urea trifluoroacetate Following the general procedure for Boc deprotection in example 36, N-(2-bromophenyl)-N'[3-[N"-[5-(tert-butoxycarbonylamino)-5-carboxypentyl]-aminosulfonyl]4-chloro-2-hydroxyphenyl] urea (108 mg, 0.17 mmol) was stirred in 1 mL of trifluoroacetic acid to form the desired product (75 mg, 66%). LC-MS (m/z) 551.2 (M$^+$).

Example 83 and 137

Preparation of N-[3-[N"-[5-(tert-butoxycarbonylamino)-5-carboxypentyl] aminosulfonyl]-4-chloro-2-hydroxyphenyl]-N'-(2,3-dichlorophenyl) urea and N-[3-[N"-(5-amino-5-carboxypentyl)aminosulfonyl]-4-chloro-2-hydroxyphenyl]-N'-(2,3-dichlorophenyl) urea hydrochloride N-[3-[N"-[5-(tert-butoxycarbonylamino)-5-carboxypentyl] aminosulfonyl]-4-chloro-2-hydroxyphenyl]-N'-(2,3-dichlorophenyl) urea Following the general procedure for urea formation outlined in example 15, N-[5-(tert-butoxycarbonylamino)-5-carboxypentyl]-3-amino-6-chloro-2-hydroxybenzenesulfonamide (233 mg, 0.518 mmol) and 2,3-dichlorophenylisocyanate (98 mg, 0.518 mmol) were coupled to form the desired urea (100 mg, 30%). LC-MS (m/z) 641.2 (M$^+$).

N-[3-[N"-(5-amino-5-carboxypentyl)aminosulfonyl]4-chloro-2-hydroxyphenyl]-N'-(2,3-dichlorophenyl) urea trifluoroacetate Following the general procedure for Boc deprotection in example 36, N-[3-[N"-[5-(tert-butoxycarbonylamino)-5-carboxypentyl]aminosulfonyl]-4-chloro-2-hydroxyphenyl]-N'-(2,3-dichlorophenyl) urea (100 mg, 0.16 mmol) was stirred in 1 mL of trifluoroacetic acid to form the desired product (78 mg, 74%). LC-MS (m/z) 541.0 (M$^+$).

Example 84 and 85

Preparation of N-(2-bromophenyl)-N'-[4-chloro-2-hydroxy-3-[N"-(2-hydroxyethyl)aminosulfonyl] urea and N-(2-bromophenyl)-N'-[3-[N"-[[(2-bromophenylamino)carboxyuethyl]-aminosulfonyl]-4-chloro-2-hydroxyphenyl] urea 2-benzyloxyethylamine To a solution of ethanolamine (5 g, 81.8 mmol) in 100 mL of dried THF was added 60% NaH (3.27 g, 81.8mmol) at room temperature. The mixture was heated to reflux for 30min, then benzyl chloride (9.32 g, 73.6 mmol) was added. The resulting mixture was refluxed for 3 hours. The mixture was concentrated, the residue was diluted with 1 N aq. HCl, extracted with dichloromethane. The aqueous layer was adjusted to pH>14 with 10% aq. NaOH, extracted with dichloromethane. The organic was dried over MgSO$_4$, concentrated to give desired product (10.11 g, 82%). $^1$H NMR (CDCl$_3$): δ 7.34 (m, 5H), 4.54 (s, 2H), 3.54 (t, 2H), 2.93 (t, 2H).

N-(2-benzyloxyethyl)-2,6-dichloro-3-nitrobenzenesulfonamide

Following the general procedure for sulfonamide formation outlined in example 15, 2,6-dichloro-3-nitrobenzenesulfonyl chloride (2.0 g, 6.88 mmol), 2-benzyloxyethyl amine(1.04 g, 6.88 mmol) and triethylamine(1.92mL, 13.76 mmol) were reacted to form the desired product (2.31 g, 83%). $^1$H NMR (MeOD-d$_4$): δ 7.69 (d, 1H), 7.53 (d, 1H), 7.25 (m, 3H), 7.14 (d, 2H), 4.26 (s, 2H), 3.45 (t, 2H), 3.36 (t, 2H).

N-(2-benzyloxyethyl)-6-chloro-2-hydroxy-3-nitrobenzenesulfonamide

Following the general hydrolysis procedure outlined in example 15, N-(2-benzyloxyethyl)-2,6-dichloro-3-nitrobenzenesulfonamide (2.31 g, 5.71 mmol), 60% NaH (683 mg, 17.1mmol) and water (103 μ, 5.72mmol) were reacted to form the desired product (1.70 g, 77%). LC-MS (m/z) 387.5(M$^+$).

N-(2-hydroxyethyl)-3-amino-6-chloro-2-hydroxybenzenesulfonamide

Following the general hydrogenation procedure outlined in example 15, N-(2-benzyloxyethyl)-6-chloro-2-hydroxy-3-nitrobenzenesulfonamide (366 mg, 0.95 mmol) was reduced with hydrogen and 10% Pd/C (170 mg). The crude product (265 mg) was carried on to the next step without purification.

N-(2-bromophenyl)-N'[4-chloro-2-hydroxy-3-[N"-(2-hydroxyethyl)-aminosulfonyl] urea and N-(2-bromophenyl)-N'-[3-[N"-[[(2-bromophenylamino)carboxy] ethyl]aminosulfonyl]-4-chloro-2-hydroxyphenyl] urea Following the general procedure for urea formation outlined in example 15, crude N-(2-hydroxyethyl)-3-amino-6-chloro-2-hydroxybenzenesulfonamide (265 mg) and 2-bromophenylisocyanate (187 mg, 0.95 mmol) were coupled to form the desired urea 84 (54 mg, 12% for two steps). LC-MS (m/z) 466.0 (M$^+$); and urea 85 (10 mg, 1.6% for two steps). LC-MS (m/z) 663.0 (M$^+$).

Example 86 and 149

Preparation of N-[3-[N"-(2-benzyloxyethyl)-aminosulfonyl]-4-chloro-2-hydroxyphenyl]-N'-(2,3-dichlorophenyl) urea and N-[3-[N"-(2-hydroxyethyl)aminosulfonyl]-4-chloro2-hydroxyphenyl]-N'-(2,3-dichlorophenyl) urea N-(2-benzyloxyethyl)-3-amino-6-chloro-2-hydroxybenzenesulfonamide A mixture of N-(2-benzyloxyethyl)-6-chloro-2-hydroxy-3-nitrobenzenesulfonamide (157 mg, 0.4mmol) in THF (15 mL) and 5% aq. NaHCO$_3$ (10 mL) was stirred at room temperature, sodium dithionite (1.5 g) was added in 0.2 g potion. The mixture was acidified with 1 N aq. HCl, extracted with ethyl acetate. The organic layer was dried over MgSO$_4$ and concentrated to give the desired product (120 mg, 82%). LC-MS (m/z) 357.0 (M$^+$).

N-[3-[N"-(2-benzyloxyethyl)aminosulfonyl]-4-chloro-2-hydroxyphenyl]-N'-(2,3-dichlorophenyl) urea Following the general procedure for urea formation outlined in example 15, N-(2-benzyloxyethyl)-3-amino-6-chloro-2-hydroxybenzenesulfonamide (119 mg, 0.33 mmol) and 2,3-dichlorophenylisocyanate (44 mg, 0.23 mmol) were coupled to form the desired urea (94 mg, 75%). LC-MS (m/z) 546.0 (M$^+$).

N-[3-[N"-(2-hydroxyethyl)aminosulfonyl]4-chloro-2-hydroxyphenyl]-N'-(2,3-dichlorophenyl) urea To a solution of N-[3-[N"-(2-benzyloxyethyl)aminosulfonyl]4-chloro-2-hydroxyphenyl]-N'-(2,3-dichlorophenyl) urea (46 mg, 0.08 mmol) in 3mL of dichloromethane was added iodotrimethylsilane (38 mg, 0.19 mmol). The mixture was stirred for 16 hours at room temperature. Purification by column chromatography on silica gel, eluting with ethyl acetate/hexane (60/40, v/v), gave the desired product (14 mg, 37%). LC-MS (m/z) 455.8 (M$^+$).

Example 87, 88, and 89

Preparation of N-(2-bromophenyl)-N'-[4-chloro-3-(N"-cyclopropylmethylaminosulfonyl)-2-hydroxy phenyl] urea, N-[4-chloro-3-(N"-cyclopropylmethylaminosulfonyl)-2-hydroxyphenyl]-N'(2,3-dichlorophenyl) urea, and N-[4-chloro-3-(N"-cyclopropylmethylaminosulfonyl)-2-hydroxylphenyl]-N'-(2-chlorophenyl)urea N-cyclopropylmethyl-2,6dichloro-3-nitrobenzenesulfonamide Following the general procedure for sulfonamide formation outlined in example 15, 2,6-dichloro-3-nitrobenzenesulfonyl chloride (1.5 g, 5.2 mmol), aminomethyl cyclopropane hydrochloride (0.56 g, 5.2 mmol) and triethylamine (1.8mL, 12.9 mmol) were reacted to form the desired product (1.28 g, 84%). LC-MS m/z 325 (M$^+$).

6-chloro-N-cyclopropylmethyl-2-hydroxy-3-nitrobenzenesulfonamide

Following the general hydrolysis procedure outlined in example 15, N-cyclopropylmethyl-2,6 dichloro-3-nitrobenzenesulfonamide (0.85 g, 2.6 mmol), 80% NaH (0.23 g, 9.88 mmol) and water (56 μL, 3.1 mmol) were reacted to form the desired product (0.58 g, 72%). LC-MS m/z 307 M+).

3-amino-6-chloro-N-cyclopropylmethyl-2-hydroxybenzenesulfonamide

Following the general hydrogenation procedure outlined in example 15, 6-chloro-N-cyclopropylmethyl-2-hydroxy-3-nitrobenzenesulfonamide (0.1 g, 3.2 mmol) was reduced with hydrogen and 10% Pd/C (0.1 g) to form the desired product (0.08 g, 89%). LC-MS m/z 277 (M$^+$).

N-(2-bromophenyl)-N'-4-chloro-3-(N"-cyclopropylmethylaminosulfonyl)-2-hydroxy phenyl]urea Following the general procedure for urea formation outlined in example 15, 3-amino-6-chloro-N-cyclopropylmethyl-2-hydroxybenzenesulfonamide (0.23 g, 0.77 mmol) and 2-bromophenylisocyanate(100 μL, 0.81 mmol) were coupled to form the desired urea (0.19 g, 52%). LC-MS m/z 474(M$^+$).

N-[4-chloro-3-(N"-cyclopropylmethylaminosulfonyl)-2-hydroxyphenyl]-N'-(2,3 dichlorophenyl) urea Following the general procedure for urea formation outlined in example 15, 3-amino-6-chloro-N-cyclopropylmethyl-2-hydroxybenzenesulfonamide (0.23 g, 0.77mmol) and 2,3-dichlorophenylisocyanate (100 μL, 0.76 mmol) were coupled to form the desired urea (0.19 g, 53%). LC-MS m/z 464 (M$^+$).

N-[4-chloro-3-(N"-cyclopropylmethylaminosulfonyl)-2-hydroxyphenyl]-N'-(2-chlorophenyl)urea Following the general procedure for urea formation outlined in example 15, 3-amino-6-chloro-N-cyclopropylmethyl-2-hydroxybenzenesulfonamide (0.23 g, 0.77 mmol) and 2-chlorophenylisocyanate(95 μL, 0.79 mmol) were coupled to form the desired urea (0.07 g, 21%). LC-MS m/z 430 (M$^+$).

Example 90, 91, and 92

Preparation of N-(2-bromophenyl)-N'-[4-chloro-2-hydroxy-3-[N"-methoxy-N"-methylaminosulfonyl) phenyl]urea, N-[4-chloro-2-hydroxy-3-(N"-methoxy-N"-methylaminosulfonyl)phenyl]-N'-(2,3-dichlorophenyl)urea, and N-(2-chlorophenyl)-N'-[4-chloro-2-hydroxy-3-(N"-methoxy-N"-methylaminosulfonyl)phenyl]urea (N-methoxy N-methyl)-2,6dichloro-3-nitrobenzenesulfonamide Following the general procedure for sulfonamide formation outlined in example 15, 2,6-dichloro-3-nitrobenzenesulfonyl chloride (1.5 g, 5.2 mmol), N,O-Dimethylhydroxylamine hydrochloride (0.52 g, 5.3 mmol) and triethylamine (2.0 mL, 14.3 mmol) were reacted to form the desired product (1.04 g, 63%). LC-MS m/z 315 (M$^+$).

(N-methoxy-N-methyl)-6-chloro-2-hydroxy-3-nitrobenzenesulfonamide

Following the general hydrolysis procedure outlined in example 15, (N-methoxy, N-methyl)-2,6-dichloro-3-nitrobenzenesulfonamide (1.0 g, 3.2 mmol), 80% NaH (0.30 g, 9.6 mmol) and water (58 μl, 3.2 mmol) were reacted to form the desired product (0.66 g, 69%). LC-MS m/z 297 (M$^+$).

(N-methoxy-N-methyl)-3-amino-6chloro-2-hydroxybenzenesulfonamide

Following the general hydrogenation procedure outlined in example 15, (N"-methoxy-N"-methyl)-6-chloro-2-hydroxy-3-nitrobenzenesulfonamide (0.66 g, 2.2 mmol) was reduced with hydrogen and 10% Pd/C (0.66 g) to form the desired product (0.50 g, 85%). LC-MS m/z 266.8 (M$^+$).

N-(2-bromophenyl)-N'-[4-chloro-2-hydroxy-3-[N"-methoxy-N"-methylaminosulfonyl)phenyl]urea Following the general procedure for urea formation outlined in example 15, (N"-methoxy-N"-methyl)-3-amino-6-chloro-2-hydroxybenzenesulfonamide (0.15 g, 0.56 mmol) and 2-bromophenylisocyanate (69 μL, 0.56 mmol) were coupled to form the desired urea (0.1 2 g, 45%). LC-MS m/z 464(M$^+$).

N-[4-chloro2-hydroxy-3-(N"-methoxy-N"-methylaminosulfonyl)phenyl]-N'-(2,3-dichlorophenyl)urea Following the general procedure for urea formation outlined in example 15, (N"-methoxy-N"-methyl)-3-amino-6-chloro-2-hydroxybenzenesulfonamide (0.15 g, 0.56 mmol) and 2,3-dichlorophenylisocyanate (74 μL, 0.56 mmol) were coupled to form the desired urea (0.086 g, 34%). LC-MS m/z 454(M⁺).

N-(2-chlorophenyl)-N'-[4-chloro-2-hydroxy-3-(N"-methoxy-N"-methylaminosulfonyl)phenyl]urea Following the general procedure for urea formation outlined in example 15, (N"-methoxy-N"-methyl)-3-amino-6-chloro-2-hydroxybenzenesulfonamide (0.15 g, 0.56 mmol) and 2-chlorophenylisocyanate (68 μL, 0.56 mmol) were coupled to form the desired urea (0.077 g, 33%). LC-MS m/z 420(M⁺).

Example 93, 94, and 95

Preparation of N-(2-bromophenyl)-N'-[4-chloro-2-hydroxy-3-(N"-pyrrolidinylaminosulfonyl)phenyl] urea, N-[4-chloro-2-hydroxy-3-(N"-pyrrolidinylaminosulfonyl)phenyl]-N'-(2,3-dichlorophenyl)urea, and N-(2-chlorophenyl)-N'-[4-chloro-2-hydroxy-3-(N"-pyrrolidinylaminosulfonyl) phenyl]urea (N-pyrrolidinyl)-2,6 dichloro-3-nitrobenzenesulfonamide Following the general procedure for sulfonamide formation outlined in example 15, 2,6-dichloro-3-nitrobenzenesulfonyl chloride (151 g, 5.2 mmol), pyrrolidine (435 μL, 5.2 mmol) and triethylamine(1.1 mL, 7.8 mmol) were reacted to form the desired product (1.16 g, 68%). LC-MS m/z 325(M⁺).

(N-pyrrolidinyl)-6chloro-2-hydroxy-3-nitrobenzenesulfonamide

Following the general hydrolysis procedure outlined in example 15, (N-pyrrolidinyl)-2,6 dichloro-3-nitrobenzenesulfonamide (1.12 g, 3.4mmol), 80% NaH (0.31 g, 10.3 mmol) and water (74 μL, 4.1mmol) were reacted to form the desired product (0.94 g, 69%). LC-MS m/z 307(M⁺).

(N-pyrrolidinyl)-3-amino-6-chloro-2-hydroxybenzenesulfonamide

Following the general hydrogenation procedure outlined in example 15, (N-pyrrolidinyl)-6-chloro-2-hydroxy-3-nitrobenzenesulfonamide (0.73 g, 2.4 mmol) was reduced with hydrogen and 10% Pd/C (0.73 g) to form the desired product (0.69 g, crude). MS m/z (M+H) 276.9, 278.89, 279.88.

N-(2-bromophenyl)-N'-[4-chloro-2-hydroxy-3-(N"-pyrrolidinyl aminosulfonyl)phenyl]urea Following the general procedure for urea formation outlined in example 15, (N-pyrrolidinyl)-3-amino-6-chloro-2-hydroxybenzenesulfonamide (0.23 g, 0.83mmol) and 2-bromophenylisocyanate (102 μL, 0.83 mmol) were coupled to form the desired urea (0.1 g, 26%). LC-MS m/z 476(M⁺).

N-[4-chloro-2-hydroxy-3-(N"-pyrrolidinylaminosulfonyl) phenyl]-N'(2,3-dichlorophenyl)urea Following the general procedure for urea formation outlined in example 15, (N-pyrrolidinyl)-3-amino-6-chloro-2-hydroxybenzenesulfonamide (0.23 g, 0.83mmol) and 2,3-dichlorophenylisocyanate(110 μL, 0.83 mmol) were coupled to form the desired urea (0.1 g, 26%). LC-MS m/z 464(M⁺).

N-(2-chlorophenyl)-N'-[4-chloro-2-hydroxy-3-(N"-pyrrolidinylaminosulfonyl)phenyl]urea Following the general procedure for urea formation outlined in example 15, (N-pyrrolidinyl)-3-amino-6-chloro-2-hydroxybenzenesulfonamide (0.23 g, 0.83mmol) and 2-chlorophenylisocyanate(100 μL, 0.83 mmol) were coupled to form the desired urea (0.1 g, 28%). LC-MS m/z 420(M⁺).

Example 96 and 97

Preparation of N-(2-bromophenyl)-N'-[4-chloro-2-hydroxy-3-[(4-pyridinylaminosulfonyl]phenyl] urea and N-[4-chloro-2-hydroxy-3-[(4-pyridinylaminosulfonyl]phenyl]-N'-(2,3-dichlorophenyl) urea.

N-(4-Pyridinyl)-2,6dichloro-3-nitrobenzenesulfonamide

Following the general procedure for sulfonamide formation outlined in example 15, 2,6-dichloro-3-nitrobenzenesulfonyl chloride (500 mg, 1.72 mmol), 4-aminopyridine (165 mg,1.75 mmol) and triethylamine (0.36mL,2.58 mmol) were reacted to form the desired product (446 mg, 76%). EI-MS m/z 346(M-H)⁻.

N-(⁴-Pyridinyl)-6-chloro-2-hydroxy-3-nitrobenzenesulfonamide

Following the general hydrolysis procedure outlined in example 15, N-(4-pyridinyl)-2,6-dichloro-3-nitrobenzenesulfonamide (540 mg, 1.55 mmol), 80% NaH (217 mg,7.25 mmol) and water (0.045mL, 2.46 mmol) were reacted to form the desired product (170 mg, 33%). EI-MS m/z 328(M-H)⁻.

N-(4-Pyridinyl)-3-amino-6-chloro-2-hydroxybenzenesulfonamide

Following the general hydrogenation procedure outlined in example 15, N-(4-pyridinyl)-6-chloro-2-hydroxy-3-nitrobenzenesulfonamide (22.0 mg, 0.066 mmol) was reduced with hydrogen and Pd/C (10.3 mg) to form the desired product (18.0 mg, 90%). EI-MS m/z 298(M-H)⁻.

N-(2-Bromophenyl)-N'-[4-chloro-2-hydroxy-3-[(4-pyridinylaminosulfonyl]phenyl] urea Following the general procedure for urea formation outlined in example 15 , N-(4-pyridinyl)-3-amino-6-chloro-2-hydroxybenzenesulfonamide (52.6 mg, 0.17 mmol) and 2-bromophenylisocyanate (0.0216mL, 0.17 mmol) were coupled to form the desired urea (66.5 mg, 76%). EI-MS m/z 496(M-H)⁻.

N-[4-Chloro-2-hydroxy-3-[(4-pyridinylaminosulfonylphenyl]-N-(2,3-dichlorophenyl) urea.

Following the general procedure for urea formation outlined in example 15, N-(4-pyridinyl)-3-amino-6-chloro-2-hydroxybenzenesulfonamide (52.6 mg, 0.017 mmol) and 2,3-d dichlorophenylisocyanate (0.023 mL, 0.17 mmol) were coupled to form the desired urea (62.8 mg, 73%). EI-MS m/z 485(M-H)⁻.

Example 98 and 99

N-(2-bromophenyl)-N'-[4-chloro-2-hydroxy-3-[[[2-(tetrahydro-2-furanyl)methyl]aminosulfonyl]phenyl] urea and N-[4-chloro-2-hydroxy-3-[[[2-(tetrahydro-2-furanyl)methyl]aminosulfonyl]phenyl]-N'-(2,3-dichlorophenyl) urea.

N-(2-Tetrahydrofurfuryl)-2,6-dichloro-3-nitrobenzenesulfonamide

Following the general procedure for sulfonamide formation outlined in example 15, 2,6-dichloro-3-nitrobenzenesulfonyl chloride (997 mg, 3.43 mmol), 2-tetrahydrofurfurylamine (0.37 mL, 3.58 mmol) and triethylamine (0.72mL, 5.16 mmol) were reacted to form the desired product (1.04 g, 86%). EI-MS m/z 353(M-H)⁻.

N-(2-Tetrahydrofurfuryl)-6-chloro-2-hydroxy-3-nitrobenzenesulfonamide

Following the general hydrolysis procedure outlined in example 15, N-(2-tetrahydrofurfuryl)-2,6-dichloro-3-nitrobenzenesulfonamide (660 mg, 1.86 mmol), 80% NaH (169 mg, 5.63 mmol) and water (0.035 mL, 1.95 mmol) were reacted to form the desired product (380 mg, 61%). EI-MS m/z 335(M-H)$^-$.

N-(2-Tetrahydrofurfuryl)-3-amino-6-chloro-2-hydroxybenzenesulfonamide

Following the general hydrogenation procedure outlined in example 15, N-(2-tetrahydrofurfuryl)-6-chloro-2-hydroxy-3-nitrobenzenesulfonamide (340 mg, 1.01 mmol) was reduced with hydrogen and Pd/C (158 mg) to form the desired product (304 mg, 98%). EI-MS m/z 305(M-H)$^-$.

N-(2-Bromophenyl)-N'-[4-chloro-2-hydroxy-3-[[[2-(tetrahydro-2-furanyl)methyl]aminosulfonyl]phenyl] urea Following the general procedure for urea formation outlined in example 15, N-(2-tetrahydrofurfuryl)-3-amino-6-chloro-2-hydroxybenzenesulfonamide (152 mg, 0.49 mmol) and 2-bromophenylisocyanate (0.061 mL, 0.49 mmol) were coupled to form the desired urea (98 mg, 40%). EI-MS m/z 504(M-H)$^-$.

N-[4-Chloro-2-hydroxy-3-[I[2-(tetrahydro-2-furanyl)methyl]aminosulfonyl]phenyl]-N'-(2,3-dichlorophenyl) urea Following the general procedure for urea formation outlined in example 15, N-(2-tetrahydrofurfuryl)-3-amino-6-chloro-2-hydroxybenzenesulfonamide (152 mg, 0.49 mmol) and 2,3-dichlorophenylisocyanate (0.065 mL, 0.49 mmol) were coupled to form the desired urea (184 mg, 76%). EI-MS m/z 492(M-H)$^-$.

Example 100 and 101

Preparation of N-(2-bromophenyl)-N'-[4-chloro-2-hydroxy-3-[[[(2R)-(tetrahydro-2-furanyl)methyl]aminosulfonyl]phenyl] urea and N-[4-chloro-2-hydroxy-3-[[[(2R)-(tetrahydro-2-furanyl)methyl]aminosulfonyl]phenyl]-N'-(2,3-dichlorophenyl) urea.

N-((2R)-Tetrahydrofurfuryl)-2,6dichloro-3-nitrobenzenesulfonamide

Following the general procedure for sulfonamide formation outlined in example 15, 2,6-dichloro-3-nitrobenzenesulfonyl chloride (993 mg, 3.41 mmol), (2R)-tetrahydrofurfurylamine (0.36 mL, 3.49 mmol) and triethylamine(0.72 mL, 5.17 mmol) were reacted to form the desired product (1.17 g, 97%). EI-MS m/z 353(M-H)$^-$.

N-((2R)-Tetrahydrofurfuryl)-6chloro-2-hydroxy-3-nitrobenzenesulfonamide

Following the general hydrolysis procedure outlined in example 15, N-((2R)-tetrahydrofurfuryl)-2,6dichloro-3-nitrobenzenesulfonamide (1.17 g, 3.29 mmol), 80% NaH (303 mg, 10.1 mmol) and water (0.063 mL, 3.49 mmol) were reacted to form the desired product (690 mg, 63%). EI-MS m/z 335(M-H)$^-$.

N-((2R)-Tetrahydrofurfuryl)-3-amino-6-chloro-2-hydroxybenzenesulfonamide

Following the general hydrogenation procedure outlined in example 15, N-((2R)-tetrahydrofurfuryl)-6-chloro-2-hydroxy-3-nitrobenzenesulfonamide (660 mg, 1.96 mmol) was reduced with hydrogen and Pd/C (303 mg) to form the desired product (563 mg, 94%). EI-MS mn/z 305(M-H)$^-$.

N-(2-Bromophenyl)-N'-[4-chloro-2-hydroxy-3-[[[(2R)-(tetrahydro-2-furanyl)methyl]aminosulfonyl]phenyl] urea Following the general procedure for urea formation outlined in example 15, N-((2R)-tetrahydrofurfuryl)-3-amino-6-chloro-2-hydroxybenzenesulfonamide (260 mg, 0.85 mmol) and 2-bromophenylisocyanate (0.11 mL, 0.85 mmol) were coupled to form the desired urea (127 mg, 30%). EI-MS m/z 504(M-H)$^-$.

N-[4-Chloro-2-hydroxy-3-[[[(2R)-(tetrahydro-2-furanyl)methyl]aminosulfonyl]phenyl]-N'-(2,3-dichlorophenyl) urea Following the general procedure for urea formation outlined in example 15, N-((2R)-tetrahydrofurfuryl)-3-amino-6-chloro-2-hydroxybenzenesulfonamide (260 mg, 0.85 mmol) and 2,3-dichlorophenylisocyanate (0.11 mL, 0.85 mmol) were coupled to form the desired urea (306 mg, 75%). EI-MS m/z 492(M-H)$^-$.

Example 102 and 103

Preparation of N-(2-bromophenyl)-N'-[4-chloro-2-hydroxy-3-[[[(2S)-(tetrahydro-2-furanyl)methyl]aminosulfonyl]phenyl] urea and N-[4-chloro-2-hydroxy-3-[[[(2S)-(tetrahydro-2-furanyl)methyl]aminosulfonyl]phenyl]-N'-(2,3-dichlorophenyl) urea.

N-((2S)-Tetrahydrofurfuryl)-2,6-dichloro-3-nitrobenzenesulfonamide

Following the general procedure for sulfonamide formation outlined in example 15, 2,6-dichloro-3-nitrobenzenesulfonyl chloride (1.01 g, 3.44 mmol), (2S)-tetrahydrofurfurylamine (0.33 mL, 3.20 mmol) and triethylamine (0.72 mL, 5.17 mmol) were reacted to form the desired product (1.12 g, 99%). EI-MS m/z 353(M-H)$^-$.

N-((2S)-Tetrahydrofurfuryl)-6-chloro-2-hydroxy-3-nitrobenzenesulfonamide

Following the general hydrolysis procedure outlined in example 15, N-((2S)-tetrahydrofurfuryl)-2,6-dichloro-3-nitrobenzenesulfonamide (1.12 g, 3.15 mmol), 80% NaH (284 mg, 9.47 mmol) and water (0.057 mL, 3.16 mmol) were reacted to form the desired product (280 mg, 26%). EI-MS m/z 335(M-H)$^-$.

N-((2S)-Tetrahydrofurfuryl)-3-amino-6-chloro-2-hydroxybenzenesulfonamide

Following the general hydrogenation procedure outlined in example 15, N-((2S)-tetrahydrofurfuryl)-6-chloro-2-hydroxy-3-nitrobenzenesulfonamide (270 mg, 0.80 mmol) was reduced with hydrogen and Pd/C (140 mg) to form the desired product (226 mg, 94%). EI-MS m/z 305(M-H)$^-$.

N-(2-Bromophenyl)-N'-[4-chloro-2-hydroxy-3-[[[(2S)-(tetrahydro-2-furanyl)methyl]aminosulfonyl]phenyl] urea Following the general procedure for urea formation outlined in example 15, N-((2S)-tetrahydrofurfuryl)-3-amino-6-chloro-2-hydroxybenzenesulfonamide (113 mg, 0.37 mmol) and 2-bromophenylisocyanate (0.045 mL, 0.37 mmol) were coupled to form the desired urea (143 mg, 77%). EI-MS m/z 504(M-H)$^-$.

N -[4-Chloro-2-hydroxy-3- [[[(2S)-(tetrahydro-2-furanyl)methyl]aminosulfonyl]phenyl]-N'-(2,3-dichlorophenyl) urea Following the general procedure for urea formation outlined in example 15, N-((2S)-tetrahydrofurfuryl)-3-amino-6-chloro-2-hydroxybenzenesulfonamide (11 3 mg, 0.37 mmol) and 2,3-dichlorophenylisocyanate (0.049 mL, 0.37 mmol) were coupled to form the desired urea (52.5 mg, 29%). EI-MS m/z 492(M-H)$^-$.

Example 104, 105, and 106

Preparation of N-(2-bromophenyl)-N'-[4-chloro-2-hydroxy-3-(N"-cyclopentylaminosulfonyl)phenyl]urea, N-[4-chloro-2-hydroxy-3-(N"-cyclopentylaminosulfonyl)phenyl]-N'-(2,3-dichlorophenyl)urea, and N-(2-chlorophenyl)-N'-[4-chloro-2-hydroxy-3-(N"-cyclopentylaminosulfonyl)phenyl]urea
(N-cyclopentyl)-2,6 dichloro-3-nitrobenzenesulfonamide Following the general procedure for sulfonamide formation outlined in example 15, 2,6-dichloro-3-nitrobenzenesulfonyl chloride (1.6 g, 5.5 mmol), cyclopentylamine (0.54 mL, 5.5 mmol) and triethylamine (1.1 mL, 7.8 mmol) were reacted to form the desired product (1.1 g, 59%). LC-MS m/z 339($M^+$).
(N-cyclopentyl)-6-chloro-2-hydroxy-3-nitrobenzenesulfonamide Following the general hydrolysis procedure outlined in example 15, (N-cyclopentyl)-2,6 dichloro-(3-nitrobenzenesulfonamide (0.7[6] g, 2.2 mmol), 80% NaH (0.22 g, 7.3mmol) and water (45 μL, 2.5 mmol) were reacted to form the desired product (0.49 g, 68%). LC-MS m/z 321($M^+$).
(N-cyclopentyl)-3-amino-6-chloro-2-hydroxybenzenesulfonamide Following the general hydrogenation procedure outlined in example 15, (N-cyclopentyl)-6-chloro-2-hydroxy-3-nitrobenzenesulfonamide (0.54 g, 1.7 mmol) was reduced with hydrogen and 10%,Pd/C (0.54 g) to form the desired product (0.45 g, crude). LC-MS m/z 291($M^+$).
N-(2-bromophenyl)-N'[4-chloro-2-hydroxy-3-(N"-cyclopentylaminosulfonyl)phenyl]urea Following the general procedure for urea formation outlined in example 15, (N-cyclopentyl)-3-amino-6-chloro-2-hydroxybenzenesulfonamide (0.15 g, 0.52 mmol) and 2-bromophenylisocyanate (64 μL, 0.52 mmol) were coupled to form the desired urea (0.1 g, 39%). LC-MS m/z 488($M^+$).
N-[4-chloro-2-hydroxy-3-(N"-cyclopentylaminosulfonyl)phenyl]-N'-(2,3-dichlorophenyl)urea Following the general procedure for urea formation outlined in example 15, (N-cyclopentyl)-3-amino-6-chloro-2-hydroxybenzenesulfonamide (0.15 g, 0.52 mmol) and 2,3-dichlorophenylisocyanate(68 μL, 0.52 mmol) were coupled to form the desired urea (0.10 g, 40%). LC-MS m/z 478 ($M^+$).
N-(2-chlorophenyl)-N'-[4-chloro-2-hydroxy-3-(N"-cyclopentylaminosulfonyl)phenyl]urea Following the general procedure for urea formation outlined in example 15, (N-cyclopentyl)-3-amino-6-chloro-2-hydroxybenzenesulfonamide (0. 15 g, 0.52 mmol) and 2-chlorophenylisocyanate (62 μL, 0.52 mmol) were coupled to form the desired urea (0.1 g, 43%). LC-MS n/z 444($M^+$).

Example 107, 108, and 109

Preparation of N-(2-bromophenyl)-N'-[4-chloro-2-hydroxy-3-(N"-isoxazolidinylaminosulfonyl)phenyl]urea, N-[4chloro-2-hydroxy-3-(N"-isoxazolidinylaminosulfonyl)phenyl]-N'-(2,3-dichlorophenyl)urea, and N-(2-chlorophenyl)-N'-[4chloro-2-hydroxy-3-(N"-isoxazolidinylaminosulfonyl)phenyl]urea
N-(ethoxycarbonyl)isoxazolidine To a solution of KOH (6.4 g, 0.11 mol) and hydroxyurethane (12 g, 0.11 mol) in ethanol (50 mL) was added 1,3-dibromopropane (5.8 mL, 0.057 mol). The resulting suspension was heated at reflux for 1 hour. After the mixture was cooled to room temperature, an additional portion of KOH (3.2 g, 0.055 mol) and of dibromopropane (2.9 mL, 0.028 mol) was added. The mixture was then refluxed for 1 hour, cooled to room temperature, and solvent was evaporated. The residue was suspended in boiling ether three times and filtered. The combined filtrates were dried over sodium sulfate, filtered, and evaporated. A portion of 3 g of the crude product was purified by flush column chromatography (EtOAC/Hexane, gradient elution), yielding 1.18 g of N-(ethoxycarbonyl)isoxazolidine. [1] H NMR (CDCl$_3$) δ 1.15 (t, 3H), 2.15 (q, 2H), 3.55(t, 2H), 3.8 (t, 2H),4.1(q, 2H).
Isoxazolidine hydrochloride N-(ethoxycarbonyl)isoxazolidine (1.18 g, 9.1 mmol) was dissolved in aqueous HCl (6N, 7 mL)and heated at reflux for 2 hours. After being cooled to room temperature, this solution was washed with ether (3x) and then evaporated affording crude isoxazolidine hydrochloride which was recrystalized from ethanol/ether yielding 0.79 g (80%) of isoxazolidine hydrochloride. [1] H NMR (CDCl$_3$; CH$_{3O\ D}$), δ 2.5 (q, 2H), 3.55 (t, 2H), 4.2(t, 2H).
(N-isoxazolidinyl)-2,6-dichloro-3-nitrobenzenesulfonamide Following the general procedure for sulfonamide formation outlined in example 15, 2,6-dichloro-3-nitrobenzenesulfonyl chloride (1.5 g, 5.2 mmol), isoxazolidine hydrochloride (0.56 g, 5.2 mmol) and triethylamine (2.2 mL, 15.5 mmol) were reacted to form the desired product (1.2 g, 71%). LC-MS m/z 327 ($M^+$).
(N-isoxazolidinyl)-6-chloro-2-hydroxy-3-nitrobenzenesulfonamide Following the general hydrolysis procedure outlined in example 15, (N-isoxazolidinyl)-2,6-dichloro-3-nitrobenzenesulfonamide (1.08 g, 3.3 mmol), 80% NaH (0.3 g, m10.0 mol) and water (72 μL, 4 mmol) were reacted to form the desired product (0.79 g, 77%). LC-MS m/z 309 ($M^+$).
(N-isoxazolidinyl)-3-amino-6chloro-2-hydroxybenzenesulfonamide Following the general hydrogenation procedure outlined in example 15, (N-isoxazolidinyl)-6-chloro-2-hydroxy-3-nitrobenzenesulfonamide (0.84 g, 2.7 mmol) was reduced with hydrogen and 10% Pd/C (0.84 g) to form the desired product (0.75 g crude). LC-MS m/z 279($M^+$).
N-(2-bromophenyl)-N'-[4-chloro-2-hydroxy-3-(N"-isoxazolidinylaminosulfonyl)phenyl]urea Following the general procedure for urea formation outlined in example 15, (N-isoxazolidinyl)-3-amino-6-chloro-2-hydroxybenzenesulfonamide (0.25 g, 0.90 mmol) and 2-bromophenylisocyanate (110 μL, 0.90 mmol) were coupled to form the desired urea (0.lg, 23%). LC-MS m/z 476($M^+$).
N[4-chloro-2-hydroxy-3-(N"-isoxazolidinylaminosulfonyl)phenyl]-N'(2,3-dichlorophenyl)urea Following the general procedure for urea formation outlined in example 15, (N-isoxazolidinyl)-3-amino-6chloro-2-hydroxybenzenesulfonamide (0.25 g, 0.90 mmol) and 2,3-dichlorophenylisocyanate (120 μL, 0.91 mmol) were coupled to form the desired urea (0.10 g, 24%). LC-MS m/z 466($M^+$).

N-(2-chlorophenyl)-N'-[4-chloro-2-hydroxy-3-(N"-isoxazolidinylaminosulfonyl)phenyl]urea Following the general procedure for urea formation outlined in example 15, (N-isoxazolidinyl)-3-amino-6-chloro-2-hydroxybenzenesulfonamide (0.25 g, 0.90 mmol) and 2-chlorophenylisocyanate (100 μL, 0.9mmol) were coupled to form the desired urea (0.g, 23%). LC-MS m/z 432($M^+$).

Example 110, 111, and 112

Preparation of N-(2-bromophenyl)-N'-[4-chloro-2-hydroxy-3-(N"-tetrahydroisoxazylaminosulfonyl)phenyl]urea, N-[4-chloro-2-hydroxy-3-(N"-tetrahydroisoxazylaminosulfonyl)phenyl]-N'-(2,3-dichlorophenyl)urea, and N-(2-chlorophenyl)-N'-[4-chloro-2-hydroxy-3-(N"-tetrahydroisoxazylaminosulfonyl)phenyl]urea N-(ethoxycarbonyl)tetrahydroisoxazine To a solution of KOH (3.34 g, 59.6mmol) and hydroxyurethane (6.1 g, 58.5 mmol) in ethanol (25 mL) was added 1,4-dibromobutane (3.5 mL, 29.3 mmol). The resulting suspension was heated at reflux for 1 hour. After the mixture was cooled to room temperature, an additional portion of KOH (1.65 g, 29.4 mmol) and of dibromopropane (1.8 mL, 15 mmol) was added. The mixture was then refluxed for 1 hour, cooled to room temperature, and solvent was evaporated. The residue was suspended in boiling ether three times and filtered. The combined filtrates were dried over sodium sulfate, filtered, and evaporated. A portion of 4 g of the crude product was purified by flush column chromatography (EtOAC/Hexane, gradient elution), yielding 1.85 g of N-(ethoxycarbonyl)tetrahydroisoxazine. $^1$H NMR (CDCl$_3$) δ 1.05 (q, 3H), 1.45 (dd, 2H), 1.55 (dd, 2H), 3.4 (t, 2H), 3.7 (t, 2H), 3.95 (q, 2H).

Tetrahydroisoxazine hydrochloride

N-(ethoxycarbonyl)tetrahydroisoxazine (1.85 g, 11.6 mmol) was dissolved in aqueous HCl (6 N, 7.8 mL) and heated at reflux for 7 hours. After being cooled to room temperature, this solution was washed with ether (3x) and then evaporated affording crude tetraisoxazine hydrochloride which was recrystalized from ethanol]ether yielding 0.74 g (52%) of tetrahydroisoxazine hydrochloride. $^1$H NMR (CH$_3$) δ 1.85 (dd, 2H), 1.95 (dd, 2H), 3.4 (t, 2H), 4.25 (t, 2H).

(N-tetrahydroisoxazyl)-2,6-dichloro-3-nitrobenzenesulfonamide

Following the general procedure for sulfonamide formation outlined in example 15, 2,6-dichloro-3-nitrobenzenesulfonyl chloride(1.75 g, 6.0 mmol), tetrahydroisoxazine hydrochloride (0.63 g, 5.1 mmol) and triethylamine (2.2 mL, 15.5 mmol) were reacted to form the desired product (1.32 g, 75%). LC-MS m/z 341(M$^+$).

(N-tetrahydroisoxazyl)-6-chloro-2-hydroxy-3-nitrobenzenesulfonamide

Following the general hydrolysis procedure outlined in example 15, (N-tetrahydroisoxazyl)-2,6 -dichloro-3-nitrobenzenesulfonamide (0.1 g, 0.29 mmol), 80% NaH (26 mg, 0.88 mmol) and water (6.3 μL, 0.35 mmol) were reacted to form the desired product (50 mg, 53%). LC-MS m/z 323(M$^+$).

(N-tetrahydroisoxazyl)-3-amino-6-chloro-2-hydroxybenzenesulfonamide

Following the general hydrogenation procedure outlined in example 15, (N-tetrahydroisoxazyl)-6-chloro-2-hydroxy-3-nitrobenzenesulfonamide (0.76 g, 2.35 mmol) was reduced with hydrogen and 10% Pd/C (0.76) to form the desired product (0.89 g, crude). LC-MS m/z 293(M$^+$).

Preparation of N-(2-bromophenyl)-N'-[4-chloro-2-hydroxy-3-(N"-tetrahydroisoxazylaminosulfonyl)phenyl]urea Following the general procedure for urea formation outlined in example 15, (N-tetrahydroisoxazyl)-3-amino-6-chloro-2-hydroxybenzenesulfonamide (0.3 g, 1.0 mmol and 2-bromophenylisocyanate (126 μL, 1.0 mmol) were coupled to form the desired urea (0.g, 20%). LC-MS m/z 490(M$^+$).

N-[4chloro-2-hydroxy-3-(N"-tetrahydroisoxazylaminosulfonyl)phenyl]-N'(2,3-dichlorophenyl)urea Following the general procedure for urea formation outlined in example 15, (N-tetrahydroisoxazyl)-3-amino-6-chloro-2-hydroxybenzenesulfonamide (0.3 g, 1.0 mmol) and 2,3-dichlorophenylisocyanate (135 μL, 1.0 mmol) were coupled to form the desired urea (0.10 g, 20%). LC-MS m/z 480(M$^+$).

N-(2-chlorophenyl)-N'-[4-chloro-2-hydroxy-3-(N"-tetrahydroisoxazylaminosulfonyl)phenyl]urea Following the general procedure for urea formation outlined in example 15, (N-tetrahydroisoxazyl)-3-amino-6-chloro-2-hydroxybenzenesulfonamide (0.3 g, 1.0 mmol) and 2-chlorophenylisocyanate (124 μL, 1.0 mmol) were coupled to form the desired urea (0.1 g, 22%). LC-MS m/z 446(M$^+$).

Example 113, 114 and 115

Preparation of N-(2-bromophenyl)-N'-[4-chloro-2-hydroxy-3-[(2-isopropoxyethyl)aminosulfonyl]phenyl] urea, N-[4-chloro-2-hydroxy-3-[(2-isopropoxyethyl) aminosulfonyl]phenyl]-N'-(2,3-dichlorophenyl) urea and N-[4-chloro-2-hydroxy-3-[(2-isopropoxyethyl)-aminosulfonylphenyl]-N'-(2-chlorophenyl) urea N-(2-isopropoxyethyl)-2,6-dichloro-3-nitrobenzenesulfonamide Following the general procedure for sulfonamide formation outlined in example 15, 2,6-dichloro-3-nitrobenzenesulfonyl chloride (1.50 g, 5.16mmol), 2-aminoethyl isopropyl ether (0.533 g, 5.16 mmol) and triethylamine (1.42 mL, 10.32 mmol) were reacted to form the desired product (1.63 g, 89%). LC-MS (m/z) 357.0 (M$^+$).

N-(2-isopropoxyethyl)-6-chloro-2-hydroxy-3-nitrobenzenesulfonamide

Following the general hydrolysis procedure outlined in example 15, N-(2-isopropoxyethyl)-2,6-dichloro-3-nitrobenzenesulfonamide (1.635 g, 4.58 mmol), 60% NaH (0.41 g, 13.74 mmol) and water (0.099 mL, 5.50 mmol) were reacted. The crude product (1.676 g) was carried on to the next step without purification. LC-MS (m/z) 340 (M-H)$^+$.

N-(2-isopropoxyethyl)-3-amino-6-chloro-2-hydroxybenzenesulfonamide

Following the general hydrogenation procedure outlined in example 15, crude N-(2-isopropoxyethyl)-6-chloro-2-hydroxy-3-nitrobenzenesulfonamide (1.17 g) was reduced with hydrogen and Pd/C (350 mg). The crude product (1.086 g) was carried on to the next step without purification. $^1$H NMR (MeOD-d$_4$): δ 6.92 (d, 1H), 6.85 (d, 1H), 3.45 (m, 1H), 3.39 (t, 2H), 3.10 (t, 2H), 1.05 (d, 6H).

N-(2-bromophenyl)-N'[4-chloro-2-hydroxy-3-[(2-isopropoxyethyl)-aminosulfonyl]phenyl] urea Following the general procedure for urea formation outlined in example 15, crude N-(2-isopropoxyethyl)-3-amino-6-chloro-2-hydroxybenzenesulfonamide (362 mg) and 2-bromophenylisocyanate (0. 132 mL, 1.07 mmol) were coupled to form the desired urea (155 mg, 29% for 3 steps). LC-MS (m/z) 508 (M-H)$^+$.

N-[4-chloro-2-hydroxy-3-[(2-isopropoxyethyl) aminosulfonyl]phenyl]-N'-(2,3-dichlorophenyl) urea Following the general procedure for urea formation outlined in example 15, crude N-(2-isopropoxyethyl)-3-amino-6-chloro-2-hydroxybenzenesulfonamide (362 mg) and 2,3-dichlorophenylisocyanate (0.141 mL, 1.07 mmol) were coupled to form the desired urea (264 mg, 50% for 3 steps). LC-MS (m/z) 498 (M-H)$^+$.

N-[4-chloro-2-hydroxy-3-[(2-isopropoxyethyl) aminosulfonyl]phenyl]-N'(2-chlorophenyl) urea Following the general procedure for urea formation outlined in example 15, crude N-(2-isopropoxyethyl)-3-amino-6-chloro-2-hydroxybenzenesulfonamide (362 mg) and 2-chlorophenylisocyanate (0.129 mL, 1.07 mmol) were coupled to form the desired urea (170 mg, 34% for 3 steps). LC-MS (m/z) 462 (M-H)$^+$.

Example 116, 117 and 118

Preparation of N-(2-bromophenyl)-N'-[4-chloro-2-hydroxy-3-[(2-ethoxyethyl)aminosulfonyl]phenyl] urea, N-[4-chloro-2-hydroxy-3-[(2-ethoxyethyl) aminosulfonyl]phenyl]-N'-(2,3-dichlorophenyl) urea and N-[4-chloro-2-hydroxy-3-[(2-ethoxyethyl)-aminosulfonyl]phenyl]-N'-(2-chlorophenyl) urea N-(2-ethoxyethyl)-2,6-dichloro-3-nitrobenzenesulfonamide Following the general procedure for sulfonamide formation outlined in example 15, 2,6-dichloro-3-nitrobenzenesulfonyl chloride (1.50 g, 5.16 mmol), 2-aminoethyl ethyl ether (0.46 g, 5.16mmol) and triethylamine (1.42 mL, 10.32 mmol) were reacted to form the desired product (1.78 g, 100%). LC-MS (m/z) 345.0 (M$^+$).

N-(2-ethoxyethyl)-6-chloro-2-hydroxy-3-nitrobenzenesulfonamide

Following the general hydrolysis procedure outlined in example 15, N-(2-ethoxyethyl)-2,6-dichloro-3-nitrobenzenesulfonamide (1.78 g, 5.16 mmol), 80% NaH (0.46 g, 15.48mmol) and water (111 μL, 6.20mmol) were reacted. The crude product (1.63 g) was carried onto the next step without purification. LC-MS (m/z) 325.0(M$^+$).

N-(2-ethoxyethyl)-3-amino-6-chloro-2-hydroxybenzenesulfonamide

Following the general hydrogenation procedure outlined in example 15, crude N-(2-ethoxyethyl)-6-chloro-2-hydroxy-3-nitrobenzenesulfonamide (0.98 g) was reduced with hydrogen and Pd/C (250 mg). The crude product (1.01 g) was carried onto the next step without purification. $^1$H NMR (MeOD-d$_4$): δ 6.88 (m, 2H), 3.40 (t, 2H), 3.36 (m, 2H), 3.13 (t, 2H), 1.08 (t, 3H).

N-(2-bromophenyl)-N'[4-chloro-2-hydroxy-3-[(2-ethoxyethyl)aminosulfonyl]phenyl] urea Following the general procedure for urea formation outlined in example 15, crude N-(2-ethoxyethyl)-3-amino-6-chloro-2-hydroxybenzenesulfonamide (333 mg) and 2-bromophenylisocyanate (204 mg, 1.03 mmol) were coupled to form the desired urea (130 mg, 26% for 3 steps). LC-MS (m/z) 494.0 (M-H)$^+$.

N-[4-chloro-2-hydroxy-3-[(2-ethoxyethyl) aminosulfonyl phenyl]-N'-(2,3-dichlorophenyl) urea.

Following the general procedure for urea formation outlined in example 15, crude N-(2-ethoxyethyl)-3-amino-6-chloro-2-hydroxybenzenesulfonamide (333 mg) and 2,3-dichlorophenylisocyanate (194 mg, 1.03 mmol) were coupled to form the desired urea (185 mg, 37% for 3 steps). LC-MS (m/z) 484.0 (M-H)$^+$.

N-[4-chloro-2-hydroxy-3-[(2-isopropoxyethyl) aminosulfonyl]phenyl]-N'(2-chlorophenyl) urea Following the general procedure for urea formation outlined in example 15, crude N-(2-ethoxyethyl)-3-amino-6-chloro-2-hydroxybenzenesulfonamide (333 mg) and 2-chlorophenylisocyanate (158 mg, 1.03 mmol) were coupled to form the desired urea (138 mg, 30% for 3 steps). LC-MS (m/z) 448.2(M-H)$^+$.

Example 119, 120 and 121

Preparation of N-(2-bromophenyl)-N'-[4-chloro-2-hydroxy-3-[(2-methoxycarbonyl)azetidin-1-yl] sulfonylphenyl) urea, N-[4chloro-2-hydroxy-3-[(2-methoxycarbonyl)azetidin-1-yl]sulfonylphenyl]-N'-(2,3-dichlorophenyl) urea and N-[4-chloro-2-hydroxy-3-[(2-carboxy)-azetidin-1-yl] sulfonylphenyl]-N'-(2,3-dichlorophenyl) urea 2-acetoxy-L-azetidine A solution of L-azetidine-carboxylic acid (700 mg, 6.92 mmol) and 1 mL of chlorotrimethylsilane in 10 mL of methanol was heated to reflux overnight. The mixture was concentrated to give the desired product quantitatively (796 mg), no purification. $^1$H NMR (CDCl$_3$): δ 9.49 (s, 1H), 5.20(m, 2H), 4.27 (m, 1H), 4.14 (m, 1H), 3.82 (s, 3H), 2.81 (m, 1H), 2.71 (m, 1H).

2,6-dichloro-1-[(2-methoxycarbonyl)azetidin-1-yl]sulfonyl-3-nitrobenzene

Following the general procedure for sulfonamide formation outlined in example 15, 2,6-dichloro-3-nitrobenzenesulfonyl chloride (2.01 g, 6.92 mmol), 2-acetoxy-L-azetidine (796 mg, 6.92 mmol) and triethylamine(1.75 mL, 17.3 mmol) were reacted to form the desired product (1.84 g, 72%). $^1$H NMR (CDCl$_3$): δ 7.68 (d, 1H), 7.61 (d, 1H), 5.09 (t, 1H), 4.46 (m, 1H), 4.06 (m, 1H), 3.59 (s, 3H), 2.55 (m, 1H), 2.49 (m, 1H).

6-chloro-2-hydroxy-1-[(2-methoxycarbonyl)azetidin-1-yl] sulfonyl-3-nitrobenzene

To a solution of 2,6-dichloro-1-[(2-methoxycarbonyl) azetidin-1-yl]sulfonyl-3-nitrobenzene (1.94 g, mmol) at room temperature was added potassium superoxide (946 mg, 13.3 mmol) in 50 mg potion. The mixture was stirred for 20 hours. The mixture was acidified with 1 N aq. HCl, extracted with ethyl acetate. Purification by column chromatography on silica gel, eluting with ethyl acetate/hexane/acetic acid (40/58/2, v/v/v) gave the desired product (767 mg, 42%). LC-MS (m/z) 351.0 (M$^+$).

6-chloro-2-hydroxy-1 -[(2-methoxycarbonyl)azetidin-1-yl] sulfonylaniline

Following the general hydrogenation procedure outlined in example 15, 6-chloro-2-hydroxy-1-[(2-methoxycarbonyl) azetidin-1-yl]sulfonyl-3-nitrobenzene (742 mg, 2.12 mmol) was reduced with hydrogen and 10% Pd/C (250 mg) to form the desired product (649 mg, 96%). $^1$H NMR (MeOD-d$_4$): δ 6.86 (m, 2H), 4.95 (t, 1H), 4.17 (m, 1H), 3.94 (m, 1H), 3.56 (s, 3H), 2.45 (m, 2H).

N-(2-bromophenyl)-N'[4-chloro-2-hydroxy-3-[(2-methoxycarbonyl)azetidin-1-yl]sulfonylphenyl] urea Following the general procedure for urea formation outlined in example 15, 6-chloro-2-hydroxy-1-[(2-methoxycarbonyl)azetidin-1-yl]sulfonylaniline (325 mg, 1.01 mmol) and 2-bromophenylisocyanate (201 mg, 1.01 mmol) were coupled to form the desired urea (390 mg, 74%). LC-MS (m/z) 520.0 (M$^+$).

N-[4-chloro-2-hydroxy-3-[(2-methoxycarbonyl)azetidin-1-yl]sulfonylphenyl]-N'-(2,3-dichlorophenyl) urea Following the general procedure for urea formation outlined in example 15, 6-chloro-2-hydroxy-1-[(2-methoxycarbonyl)azetidin-1-yl]sulfonylaniline (325 mg, 1.01 mmol) and 2,3-dichlorophenylisocyanate (190 mg, 1.01 mmol) were coupled to form the desired urea (479 mg, 93%). LC-MS (m/z) 510.0 (M$^+$).

N-[4-chloro-2-hydroxy-3-[(2-carboxy)-azetidin-1 -yl] sulfonylphenyl]-N'-(2,3-dichlorophenyl) urea A solution of N-[4-chloro-2-hydroxy-3-[(2-methoxycarbonyl)azetidin-1-yl]sulfonylphenyl]-N'-(2,3-dichlorophenyl) urea (359 mg, 0.71 mmol) and lithium hydroxide monohydrate (296 mg) in methanol (10 mL) and water (1 mL) was stirred at room temperature for 16 hours. The mixture was concentrated, the residue was acidified with 1 N aq. HCl. The resulting mixture was filtered, the white solid was collected and dried in vacuo to give the desired product (332 mg, 95%). LC-MS (m/z) 496.0 (M+).

Example 122, 123 and 124

Preparation of N-(2-bromophenyl)-N'-14-chloro-2-hydroxy-3-[N"-[3-(4-morpholinyl)propyl] aminosulfonyl]phenyl) urea hydrochloride, N-[4-chloro-2-hydroxy-3-[N"-[3-(4-morpholinyl)propyl]-aminosulfonyl]phenyl]-N'-(2,3-dichlorophenyl) urea hydrochloride and N-[4-chloro-2-hydroxy-3-[N"-[3-(4-morpholinyl)propyl]aminosulfonyl]phenyl]-N'-(2-chlorophenyl) urea hydrochloride N-[3-(4-morpholinyl)propyl]-2,6-dichloro3-nitrobenzenesulfonamide Following the general procedure for sulfonamide formation outlined in example 15, 2,6-dichloro-3-nitrobenzenesulfonyl chloride (2.0 g, 6.88 mmol), 4-(3-aminopropyl)morpholine (993 mg, 6.88 mmol) and triethylamine(1.92 mL, 13.76 mmol) were reacted to form the desired product (2.04 g, 74%). LC-MS (m/z) 398.0 (M+).

N-[3-(4-morpholinyl)propyl]-6-chloro-2-hydroxy-3-nitrobenzenesulfonamide

Following the general hydrolysis procedure outlined in example 15, N-[3-(4-morpholinyl)propyl]-2,6-dichloro-3-nitrobenzenesulfonamide (10 g, 2.51 mmol), 60% NaH (301 mg, 7.53 mmol) and water (54 μL, 3.0 mmol) were reacted. The mixture was acidified with 4.ON HCl in 1,4-dioxane and concentrated to give the crude product (1.01 g), which was carried onto the next steps without purification. LC-MS 380.0 (M+).

N-[3-(4-morpholinyl)propyl]-3-amino-6-chloro-2-hydroxybenzenesulfonamide

Following the general hydrogenation procedure outlined in example 15, crude N-[3-(4-morpholinyl)propyl]-6-chloro-2-hydroxy-3-nitrobenzenesulfonamide (1.01 g) was reduced with hydrogen and 10% Pd/C (250 mg). The crude product (890 mg) was carried onto the next step without purification. $^1$H NMR (MeOD-d$_4$): δ 6.86 (m, 2H), 3.87 (m, 4H), 3.15 (m, 6H), 2.98 (t, 2H), 1.92 (m, 2H).

N-(2-bromophenyl)-N'[4-chloro-2-hydroxy-3-[N"-[3-(4-morpholinyl)propyl]-aminosulfonyl]phenyl] urea hydrochloride Following the general procedure for urea formation outlined in example 15, crude N-[3-(4-morpholinyl)propyl]-3-amino-6-chloro-2-hydroxybenzenesulfonamide (297 mg) and 2-bromophenylisocyanate (166 mg, 0.83 mmol) were coupled to form the desired urea (19 mg, 39% for 3 steps). LC-MS (m/z) 549.2 (M+).

N -[4-chloro-2-hydroxy-3-[N"-[3-(4-morpholinyl)propyl] aminosulfonyl]phenyl]-N'-(2 ,3-dichlorophenyl) urea hydrochloride Following the general procedure for urea formation outlined in example 15, crude N-[3-(4-morpholinyl)propyl]-3-amino-6-chloro-2-hydroxybenzenesulfonamide (297 mg) and 2,3-dichlorophenylisocyanate (1 57 mg, 0.83 mmol) were coupled to form the desired urea (134 mg, 28% for 3 steps). LC-MS (m/z) 539.2 (M+).

N-[4-chloro-2-hydroxy-3-[N"-[3-(4-morpholinyl)propyl] aminosulfonyl]phenyl]-N'-(2-chlorophenyl) urea hydrochloride Following the general procedure for urea formation outlined in example 15, crude N-[3-(4-morpholinyl)propyl]-3-amino-6-chloro-2-hydroxybenzenesulfonamide (297 mg) and 2-chlorophenylisocyanate (127 mg, 0.83 mmol) were coupled to form the desired urea (133 mg, 29% for 3 steps). LC-MS (m/z) 503.2 (M+).

Example 125 and 126

Preparation of N-(2-bromophenyl)-N'-[4-chloro-2-hydroxy-3-[S-(−)-(2-methoxymethyl)pyrrolidin-1-yl] sulfonylphenyl] urea and N-(2-bromophenyl)-N'-[4-chloro-2-hydroxy-3-[S-(−)-(2-hydroxymethyl) pyrrolidin-1-yl]sulfonylphenyl] urea 2,6-dichloro-1-[S-(−)-(2-methoxymethyl)pyrrolidin-1-yl]sulfonyl-3-nitrobenzene Following the general procedure for sulfonamide formation outlined in example 15, 2,6-dichloro-3-nitrobenzenesulfonyl chloride (2.0 g, 6.88mmol), S-(−)-2-(methoxymethyl)pyrrolidine (793 mg, 6.88 mmol) and triethylamine(1.9 mL, 13.76 mmol) were reacted to form the desired product (2.2 mg, 87%). LC-MS (m/z) 369.0 (M+).

6-chloro-2-hydroxy-1 -[S-(−)-(2-methoxymethyl)pyrrolidin-1-yl)sulfonyl-3-nitrobenzene Following the general hydrolysis procedure outlined in example 15, 2,6dichloro-1-[S-(−)-(2-methoxymethyl) pyrrolidin-1-yl]sulfonyl-3-nitrobenzene (1.0 g, 2.71 mmol), 60% NaH (325 mg, 8.—mmol) and water (59 μL, 3.3 mmol) were reacted. The crude product (1.0 g) was carried onto the next step without purification. LC-MS (m/z) 351.0 (M+).

4-chloro-2-hydroxy-3-[S-(−)-(2-methoxymethyl)pyrrolidin-1-yl]sulfonylaniline

Following the general hydrogenation procedure outlined in example 15, crude 6-chloro-2-hydroxy-1-[S-(−)-(2-methoxymethyl)pyrrolidin-1-yl]sulfonyl-3-nitrobenzene (1.0 g) was reduced with hydrogen and 10% Pd/C (320 mg). The crude product (0.92 g) was carried onto the next step without purification. $^1$H NMR (MeOD-d$_4$): δ 6.91 (d, 1H), 6.89 (d, ]H), 4.41 (m, 1H), 3.39 (m, 2H), 3.21 (s, 3H), 1.83–1.97 (m, 6H).

N-(2-bromophenyl)-N'-[4-chloro-2-hydroxy-3-[S-(−)-(2-methoxymethyl)pyrrolidin-1-yl]sulfonylphenyl] urea Following the general procedure for urea formation outlined in example 15, crude 4-chloro-2-hydroxy-3-[S-(−)-(2-methoxymethyl)pyrrolidin-1-yl]sulfonylaniline (306 mg) and 2-bromophenylisocyanate (188 mg, 0.95 mmol) were coupled to form the desired urea (170.4 mg, 35% for 3 steps). LC-MS (m/z) 520.0(M+)

N-(2-bromophenyl)-N'- [4-chloro-2-hydroxy-3-[S-(−)-(2-hydroxymethyl)pyrrolidin-1-yl]sulfonylphenyl] urea To a solution of N-(2-bromophenyl)-N'-[4-chloro-2-hydroxy-3-[S-(−)-(2-methoxymethyl)pyrrolidin-1-yl] sulfonylphenyl] urea (92 mg, 0.18 mmol) in dichloromethane at ice-bath was added 1. M boron tribromide (0.53mL, 0.53 mmol) in dichloromethane. The mixture was stirred for 16 hours. Purification by column chromatography on silica gel, eluting with ethyl acetate/hexane (50/50, v/v) gave the desired product (65 mg, 73%). LC-MS (m/z) 506.0 (M+).

Example 127 and 128

N-[4-chloro-2-hydroxy-3-[S-(−)-(2-methoxymethyl) pyrrolidin-1-yl]sulfonylphenyl]-N'-(2,3-dichlorophenyl) urea and N-[4-chloro-2-hydroxy-3-[S-(−)-(2-hydroxymethyl)-pyrrolidin-1ylsulfonyl] phenyl]-N'-(2,3-dichlorophenyl) urea N-[4-chloro-2-hydroxy-3-[S-(−)-(2-methoxymethyl) pyrrolidin- 1-yl]sulfonyl-phenyl]-N'-(2,3-dichlorophenyl) urea Following the general procedure for urea formation outlined in example 15, crude 4chloro-2-hydroxy-3-[S-(−)-(2- methoxymethyl)pyrrolidin-1-yl]sulfonylaniline (306 mg) and 2,3-dichlorophenylisocyanate (179 mg, 0.95 mmol) were coupled to form the desired urea (218 mg, 45% for 3 steps). LC-MS (m/z) 510.2 (M+).

N-[4-chloro-2-hydroxy-3-[S-(−)-(2-hydroxymethyl)-pyrrolidin-1-yl]sulfonyl]phenyl-N'-(2,3-dichlorophenyl) urea Following the deprotection procedure outlined in example 126, N-[4-chloro-2-hydroxy-3-[S-(−)-(2-methoxymethyl)pyrrolidin- I -ylsulfonyl-phenyl]-N'-(2,3-dichlorophenyl) urea (80 mg, 0.16 mmol) and 1.0 M boron tribromide (0.78 mL, 0.78 mmol) were reacted to the desired product (50 mg, 64%). LC-MS (m/z) 494.0 (M+).

Example 129 and 130

N-[4-chloro-2-hydroxy-3-[S-(−)-(2-methoxymethyl)-pyrrolidin-1-yl]sulfonylphenyl]-N'-(2-chlorophenyl) urea and N-[4-chloro-2-hydroxy-3-[S-(−)-(2-hydroxymethyl)-pyrrolidin-1-yl]sulfonylphenyl]-N'-(2-chlorophenyl) urea N-[4-chloro-2-hydroxy-3-[S-(−)-(2-methoxymethyl) pyrrolidin-1-yl]sulfonylphenyl]-N'L(2-chlorophenyl) urea Following the general procedure for urea formation outlined in example 15, crude 4-chloro-2-hydroxy-3-[S-(−)-(2-methoxymethyl)pyrrolidin-1-yl]sulfonylaniline (306 mg) and 2-chlorophenylisocyanate (146 mg, 0.96 mmol) were coupled to form the desired urea (129 mg, 29% for 3 steps). LC-MS (m/z) 474.2 (M+).

N-[4-chloro-2-hydroxy-3-[S-(−)-(2-hydroxymethyl)-pyrrolidin-1-yl]sulfonylphenyl]-N'-(2-chlorophenyl) urea Following the deprotection procedure outlined in example 126, N-[4-chloro-2-hydroxy-3-[S-(−)-(2-methoxymethyl) pyrrolidin-1-yl]sulfonylphenyl]-N'-(2-chlorophenyl) urea (63 mg, 0.13 mmol) and 1.0 M boron tribromide (0.65mL, 0.65 mmol) were reacted to give the desired product (35 mg, 58%). LC-MS (m/z) 460.0 (M+).

Example 131 and 132

Preparation of N-(2-bromophenyl)-N'-[4-chloro-2-hydroxy-3-[S-(2-methoxycarbonyl)pyrrolidin-1-yl] sulfonylphenyl] urea and N-(2-bromophenyl)-N'-[4-chloro-2-hydroxy-3-[S-(2-carboxy)pyrrolidin-1-yl] sulfonylphenyl] urea 2,6-dichloro-1-[S-(2-methoxycarbonyl)pyrrolidin-1-yl] sulfonyl-3-nitrobenzene Following the general procedure for sulfonamide formation outlined in example 15, 2,6-dichloro-3-nitrobenzenesulfonyl chloride (4.79 g, 1 6.5 mmol), L-proline methyl ester hydrochloride (2.73 g, 16.5 mmol) and triethylamine(4.60 mL, 33 mmol) were reacted to form the desired product (5.02 g, 79%). LC-MS (m/z) 383.0 (M+).

6-chloro-2-hydroxy-1-[S-(2-methoxycarbonyl)pyrrolidin-1-yl]sulfonyl-3-nitrobenzene To a solution 2,6-dichloro-1-[S-(2-methoxycarbonyl) pyrrolidin-1-yl]sulfonyl-3-nitrobenzene (1.0 g, 2.6 mmol) at room temperature was added potassium superoxide (370 mg, 5.2 mmol) in 50 mg potion. The mixture was stirred for 16 hours. The mixture was acidified with 1 N aq. HCl, extracted with ethyl acetate. Purification by column chromatography on silica gel, eluting with ethyl acetate/hexane/ acetic acid (50/48/2, v/v/v) gave the desired product (384 mg, 40%). LC-MS (m/z) 365.2 (M−).

4-chloro-2-hydroxy-3-[S-(2-methoxycarbonyl)pyrrolidin-1-yl]sulfonylaniline

Following the general hydrogenation procedure outlined in example 15, 6-chloro-2-hydroxy-1-[S-(2-methoxycarbonyl)pyrrolidin-1-yl]sulfonyl-3-nitrobenzene (380 mg, 1.04 mmol) was reduced with hydrogen and 10% Pd/C (110 mg) to form the desired product (340 mg, 98%). $^1$H NMR (MeOD-d$_4$): δ 6.84 (m, 2H), 4.58 (m, 1H), 3.67 (s, 3H), 2.25 (m, 2H), 2.10 (m, 2H), 1.95 (in, 2H).

N-(2-bromophenyl)-N'-[4-chloro-2-hydroxy-3-[S-(2-methoxycarbonyl)pyrrolidin-1-yl]sulfonylphenyl] urea Following the general procedure for urea formation outlined in example 15, 4-chloro-2-hydroxy-3-[S-(2-methoxycarbonyl)pyrrolidin-1-yl] sulfonylaniline (339 mg, 1.01 mmol) and 2-bromophenylisocyanate (201 mg, 1.01 mmol) were coupled to form the desired urea (223 mg, 41%). LC-MS (m/z) 534.0 (M+)

N-(2-bromophenyl)-N'-[4-chloro-2-hydroxy-3-[S-(2-carboxy)pyrrolidin-1-yl]sulfonylphenyl) urea A solution of N-(2-bromophenyl)-N'-[4chloro-2-hydroxy-3-[S-(2-methoxycarbonyl)pyrrolidin-1-yl]sulfonylphenyl] urea (40 mg, 0.075 mmol) and lithium hydroxide monohydrate (40 mg) in methanol (10 mL) and water (1 mL) was stirred at room temperature for 16 hours. The mixture was concentrated, the residue was acidified with 1 N aq. HCl. The resulting mixture was filtered, the white solid was collected and dried in vacuo to give the desired product (39 mg, 100%). LC-MS (m/z) 520.0 (M+)

Example 133, 134 and 135

Preparation of N-(2-bromophenyl)-N'-[3-[N"-(tert-butyl)aminosulfonyl]-4-chloro-2-hydroxyphenyl] urea, N-[3-[N"-(tert-butyl)aminosulfonyl]-4-chloro-2-hydroxyphenyl]-N'-(2,3-dichlorophenyl) urea and N-[3-[N"-(tert-butyl)aminosulfonyl]-4-chloro-2-hydroxylphenyl]-N'-(2-chlorophenyl) urea N-(tert-butyl)-2,6-dichloro-3-nitrobenzenesulfonamide Following the general procedure for sulfonamide formation outlined in example 15, 2,6-dichloro-3-nitrobenzenesulfonyl chloride (2.0 g, 6.88 mmol), tert-butylamine (503 mg, 6.88mmol) and triethylamine(1.43 mL, 10.32 mmol) were reacted to form the desired product (1.67 g, 75%). $^1$H NMR (MeOD-d$_4$): δ 7.91 (d, 1H), 7.78 (d, 1H), 1.25 (s, 9H).

N-(tert-butyl)-6-chloro-2-hydroxy-3-nitrobenzenesulfonamide

Following the general hydrolysis procedure outlined in example 15, N-(tert-butyl)-2,6-dichloro-3-nitrobenzenesulfonamide (1.67 g, 5.1 mmol), 60% NaH (612 mg, 15.3 mmol) and water (92 μL, 51 mmol) were reacted to form the crude product (1.54 g), which was carried on to the next step without purification. $^1$H NMR (MeOD-d$_4$): δ 8.00 (d, 1H), 7.08 (d, 1H), 1.24 (s, 9H).

N-(tert-butyl)-3-amino-6-chloro-2-hydroxybenzenesulfonamide

Following the general hydrogenation procedure outlined in example 15, crude N-(tert-butyl)6chloro-2-hydroxy-3-nitrobenzenesulfonamide (1 .54 g) was reduced with hydrogen and 10% Pd/C (670 mg). The crude product (1.23 g) was carried on to the next step without purification. $^1$H NMR (MeOD-d$_4$): δ 6.82 (m, 2H), 1.22 (s, 9H).

N-(2-bromophenyl)-N'-[3-[N"-(tert-butyl)aminosulfonyl]-4-chloro-2-hydroxyphenyl] urea Following the general procedure for urea formation outlined in example 15, crude N-(tert-butyl)-3-amino-6-chloro-2-hydroxybenzenesulfonamide (410 mg) and 2-bromophenylisocyanate (322 mg, 1.62 mmol) were coupled to form the desired urea (228 mg, 32% for 3 steps). LC-MS (m/z) 478.0 (M+)

N-[3-[N"-(tert-butyl)aminosulfonyl]-4-chloro-2-hydroxyphenyl]-N'(2,3-dichlorophenyl) urea Following the general procedure for urea formation outlined in example 15, crude N-(tert-butyl)-3-amino-6-chloro-2-hydroxybenzenesulfonamide (410 mg) and 2,3-dichlorophenylisocyanate (304 mg, 1.62 mmol) were coupled to form the desired urea (336.1 mg, 49% for 3 steps). LC-MS (m/z) 468.0 (M$^+$)

N-[3-[N"-(tert-butyl)aminosulfonyl-4-chloro-2-hydroxylphenyl]-N'-(2-chlorophenyl) urea Following the general procedure for urea formation outlined in example 15, crude N-(tert-butyl)-3-amino-6-chloro-2-hydroxybenzenesulfonamide (410 mg) and 2-chlorophenylisocyanate (249 mg, 1.62 mmol) were coupled to form the desired urea (243 mg, 38% for 3 steps). LC-MS (mn/z) 432.0 (M$^+$)

Example 138 and 139

Preparation of N-[3-[N"-[5-(tert-butoxycarbonylamino)-5-carboxypentyl]aminosulfonyl]-4-chloro-2-hydroxyphenyl]-N'-(2-chlorophenyl) urea and N-[3-[N"-(5-amino-5-carboxypentyl)aminosulfonyl]-4-chloro-2-hydroxyphenyl]-N'-(2-chlorophenyl) urea hydrochloride N-[3-[N"-[5-(tert-butoxycarbonylamino)-5-carboxypentylaminosulfonyl]4-chloro-2-hydroxyphenyl]-N'-(2-chlorophenyl) urea Following the general procedure for urea formation outlined in example 15, N-[5-(tert-butoxycarbonylamino)-5-carboxypentyl]-3-amino-6-chloro-2-hydroxybenzenesulfonamide (233 mg, 0.52mmol) and 2-chlorophenylisocyanate (80 mg, 0.52 mmol) were coupled to form the desired urea (97 mg, 31%). LC-MS (m/z) 605.2 (M$^+$).

N-[3-[N"-(5-amino-5-carboxypentyl)aminosulfonyl]-4-chloro-2-hydroxyphenyl]-N'(2-chlorophenyl) urea hydrochloride Following the general procedure for Boc deprotection in example 36, N-[3-[N"-[5-(tert-butoxycarbonylamino)-5-carboxypentyl]aminosulfonyl]-4-chloro-2-hydroxyphenyl]-N'(2-chlorophenyl) urea (104 mg, 0.17 mmol) was stirred in 1 mL of trifluoroacetic acid to form the desired product (64 mg, 61%). LC-MS (m/z) 505.0 (M$^+$).

Example 142, 143 and 144

Preparation of N-[4-chloro-3-(1,1-dioxidothiomorpholinosulfonyl)-2-hydroxyphenyl]-N'-(2,3-dichlorophenyl) urea, N-(2-bromophenyl)-N'-[4-chloro-3-(1,1-dioxidothiomorpholinosulfonyl)-2-hydroxyphenyl] urea and N-[4-chloro-3-(1,1-dioxidothiomorpholinosulfonyl)-2-hydroxyphenyl]-N'-(2-chlorophenyl) urea 6-chloro-1-(1,1-dioxidothiomorpholinosulfonyl)-2-hydroxy-3-nitrobenzene A solution of 6-chloro-2-hydroxy-3-nitro-1-(4-thiomorpholinylsufonyl)benzene (563 mg, 1.67 mmol) and m-chloroperbenzoic acid (1.73 g, 5.01 mmol) in dichloromethane (60 mL) was stirred for 3 days at room temperature. The mixture was diluted with ethyl acetate and washed with water to give the crude. Purification by column chromatography on silica gel, eluting with ethyl acetate/hexane/acetic acid (49/50/1, v/v/v), gave the desired product (230 mg, 37%). EI-MS (m/z) 368.92, 371.03 (M$^+$).

4-chloro-3-(1,1-dioxidothiomorpholinosulfonyl)-2-hydroxyaniline

Following the general hydrogenation procedure outlined in example 15, 6-chloro-1-(1,1-dioxidothiomorpholinosulfonyl)-2-hydroxy-3-nitrobenzene (220 mg, 0.60 mmol) was reduced with hydrogen and 10% Pd/C (100 mg) to give the desired (186 mg, 92%). $^1$H NMR (MeOD-d$_4$): δ 6.88 (m, 2H), 3.85 (t, 4H), 3.22 (t, 4H).

N-[4-chloro-3-(1,1-dioxidothiomorpholinosulfonyl)-2-hydroxyphenyl]-N'-(2,3-dichlorophenyl) urea Following the general procedure for urea formation outlined in example 15, 4-chloro-3-(1,1-dioxidothiomorpholinosulfonyl)-2-hydroxyaniline (62 mg, 0.18 mmol) and 2,3-dichlorophenylisocyanate (41 mg, 0.22 mmol) were coupled to form the desired urea (32 mg, 34%). LC-MS (m/z) 528.0 (M$^+$).

N-(2-bromophenyl)-N'-[4-chloro-3-(1,1-dioxidothiomorpholinosulfonyl)-2-hydroxyphenyl] urea Following the general procedure for urea formation outlined in example 15, 4-chloro-3-(1,1-dioxidothiomorpholinosulfonyl)-2-hydroxyaniline (62 mg, 0.18 mmol) and 2-bromophenylisocyanate (44 mg, 0.22 mmol) were coupled to form the desired urea (28 mg, 29%). LC-MS (m/z) 539.8 (M$^+$).

N-[4-chloro-3-(1,1-dioxidothiomorpholinosulfonyl)-2-hydroxyphenyl]-N'-(2-chlorophenyl) urea Following the general procedure for urea formation outlined in example 15, 4-chloro-3-(1,1-dioxidothiomorpholinosulfonyl)-2-hydroxyaniline (62 mg, 0.018 mmol) and 2-chlorophenylisocyanate (34 mg, 0.22 mmol) were coupled to form the desired urea (29 mg, 32%). LC-MS (m/z) 496.0 (M$^+$).

Example 145 and 146

Preparation of N-[3-[N"-[2-(tert-butoxycarbonylamino)ethyl]aminosulfonyl]-4-chloro2-hydroxyphenyl]N'-(2,3-dichlorophenyl) urea and N-[3-[N"-(2-aminoethyl)aminosulfonyl]-4-chloro-2-hydroxyphenyl]-N'-(2,3-dichlorophenyl) urea trifluoroacetate N-[3-[N"-[2-(tert-butoxycarbonylamino)ethyl]aminosulfonyl]-4-chloro-2-hydroxyphenyl]- N'-(2,3-dichlorophenyl) urea Following the general procedure for urea formation outlined in example 15, N-[2-(tert- butoxycarbonylamino)ethyl]-3-amino-6-chloro-2-hydroxybenzenesulfonamide (220 mg, 0.60 mmol) and 2,3-dichlorophenylisocyanate (125 mg, 0.66 mmol) were coupled to form the desired urea (220 mg, 66%). LC-MS (m/z) 553.2 (M$^+$).

N-[3-[N"-(2-aminoethyl)aminosulfonyl]4-chloro-2-hydroxyphenyl]-N'(2,3-dichlorophenyl) urea trifluoroacetate Following the general procedure for Boc deprotection outlined in example 36, N-[3-[N"-[2-(tert-butoxycarbonylamino)ethyl]aminosulfonyl]4-chloro-2-hydroxyphenyl]-N'(2,3-dichlorophenyl) urea (56 mg, 0.10 mmol) was stirred in trifluoroacetic acid to form the desired product (57 mg, 100%). LC-MS (m/z) 453.0 (M$^+$).

Example 147 and 148

Preparation of N-[3-[N"-[2-(tert-butoxycarbonylamino)ethyl]aminosulfonyl]-4-chloro-2-hydroxyphenyl]-N'-(2-chlorophenyl) urea and N-[3-[N"-(2-aminoethyl)aminosulfonyl]4-chloro-2-hydroxyphenyl]-N'-(2-chlorophenyl) urea trifluoroacetate N-[3-[N"-[2-(tert-butoxycarbonylamino)ethyl] aminosulfonyl]4-chloro-2-hydroxyphenyl]-N'-(2-chlorophenyl) urea Following the general procedure for urea formation outlined in example 15, N-[2-(tert-butoxycarbonylamino) ethyl]-3-amino-6-chloro-2-hydroxybenzenesulfonamide (220 mg, 0.60 mmol) and 2-bromophenylisocyanate(111 mg, 0.66 mmol) were coupled to form the desired urea (169 mg, 54%). LC-MS (m/z) 519.2 (M$^+$).

N-[3-[N"-(2-aminoethyl)aminosulfonyl]-4-chloro-2-hydroxyphenyl]-N'(2-chlorophenyl) urea trifluoroacetate Following the general procedure for Boc deprotection outlined in example 36, N-[3-[N"-[2-(tert-butoxycarbonylamino)ethyl]aminosulfonyl]4-chloro-2-hydroxyphenyl]-N'(2-chlorophenyl) urea (57 mg, 0.11 mmol) was stirred in trifluoroacetic acid to form the desired product (51 mg, 87%). LC-MS (m/z) 419.2 (M$^+$).

Example 150

Preparation of N-[4-chloro-2-hydroxy-3- (N",N"-dimethylaminosulfonyl)phenyl]-N'-(2-chlorophenyl) urea.

a) N-dimethyl-2,6-dichloro-3-nitrobenzenesulfonamide

Following the general procedure for sulfonamide formation outlined in example 15, 2,6-dichloro-3-nitrobenzenesulfonyl chloride (2.0 g, 6.9 mmol), dimethylamine (2.0 M in MeOH, 3.5 mL, 6.9 mmol) and triethylamine (1.44 mL, 10.35 mmol) were reacted to form the desired product (1.45 g, 70.4%). EI-MS m/z 298 (M-H)$^-$.

b) N",N"-dimethyl-6-chloro-2-hydroxy-3-nitrobenzenesulfonamide

Following the general hydrolysis procedure outlined in example 15, N",N"-dimethyl-2,6-dichloro-3-nitrobenzenesulfonamide (2.64 g, 8.83 mmol), NaH (60%, 1.06 g, 26.5 mmol) and water (191 mg, 10.6 mmol) were reacted to form the desired product (2.3 g, 93%). EI-MS m/z 279.5 (M-H)$^-$.

c) N",N"-dimethyl-3-amino-6-chloro-2-hydroxybenzenesulfonamide

Following the general hydrogenation procedure outlined in example 15, N",N"-dimethyl-6-chloro-2-hydroxy-3-nitrobenzenesulfonamide (2.3 g, 8.2 mmol) was reduced with hydrogen and Pd/C (2.3 g) to form the desired product (2.0 g, 97%). EI-MS m/z 249.5 (M-H)$^-$.

d) N-[4-chloro-2-hydroxy-3-[(N",N"-dimethylaminosulfonyl)phenyl]-N'(2-chlorophenyl1) urea Following the general procedure for urea formation outlined in example 15, N",N"-dimethyl-3-amino-6-chloro-2-hydroxybenzenesulfonamide (200 mg, 0.8 mmol) and 2-chlorophenylisocyanate (123 mg, 0.8 mmol) were coupled to form the desired urea (270 mg, 83%). EI-MS m/z 403.2 (M-H)$^-$.

Example 151

Preparation of N-[4-chloro-2-hydroxy-3-(aminosulfonyl)phenyl]-N'-(2-chloro-3-fluorophenyl) urea a) 2-chloro-3-fluoronitrobenzene To a -78° C. solution of 3-fluoronitrobenzene (2 g, 14.2 mmol) in THF (30 mL) was added N-chlorosuccinimide (5.69 g, 42.6 mmol) in THF (20 mL), NaHMDS (1 M in THF, 28.4 mL, 28.4 mmol) was then added dropwise to maintain an internal temperature below -75° C. The resulting mixture was stirred for 30 min at -78° C. Then it was partitioned between 5% of HCl and ethyl acetate. The combined organic layer is dried over MgSO$_4$ and filtered. The solvent was evaporated and chromatography of the resulting solid on silica gel (20% Ethyl acetate Hexane) gave the desired product(231 mg, 9.2%). EI-MS m/z 176.5 (M$^+$).

b) 2-chloro-3-fluoroaniline To the solution of 2-chloro-3-fluoronitrobenzene (231 mg, 1.32 mmol) in ethanol (10 mL), Tin (II) chloride (1.48 g, 6.6 mmol) was added. The reaction mixture was stirred at room temperature for 16 hours. The NaHCO$_3$ (aq) was added to pH=7. Then was extracted with ethyl acetate (3x). The combined organic layer was dried over MgSO$_4$, filtered and concentrated under reduced pressure to give desired product (136 mg, 71%). EI-MS m/z 146.5 (M$^+$).

c) N-[4-chloro-2-hydroxy-3-(aminosulfonyl)phenyl]-N'-(2-chloro-3-fluorophenyl) urea To a solution of 2-chloro-3-fluoroaniline (136 mg, 0.94 mmol) in toluene (10 mL), triphosgene (111 mg, 0.37 mmol) and triethyl amine (0.13 mL, 1.12 mmol) were added. The reaction mixture was stirred at 80° C. for 4 hours. Then the reaction mixture was concentrated under reduced pressure and then it was added to 3-amino-6-chloro-2-hydroxybenzenesulfonamide (104 mg, 0.47 mmol) in DMF (1 mL), The reaction mixture was stirred at room temperature for 16 hours. Chromatography of the resulting liquid on silica gel (30%Ethyl acetate/Hexane) gave desired product (80 mg, 43%). EI-MS m/z 395.2 (M$^+$).

Example 152

Preparation of N-[4chloro-2-hydroxy-3-(aminosulfonyl)phenyl]-N'-(2-bromo-3-fluorophenyl) urea a) 2-chloro-3-fluoronitrobenzene To a -78° C. solution of 3-fluoronitrobenzene (2 g, 14.2 mmol) in THF (30 mL) was added N-bromosuccinimide (7.58 g, 42.6 mmol) in THF (20 mL), NaHMDS (1 M in THF, 28.4 mL, 28.4 mmol) was then added dropwise to maintain an internal temperature below -75° C. The resulting mixture was stirred for 30 min at -784C. Then it was partitioned between 5% of HCL and ethyl acetate. . The combined organic layer is dried over MgSO$_4$ and filtered. The solvent was evaporated and chromatography of the resulting solid on silica gel (20% Ethyl acetate/Hexane) gave the desired product (300 mg, 9.6%). EI-MS m/z 221 (M$^+$).

b) 2-chloro-3-fluoroaniline

To the solution of 2-bromo-3-fluoronitrobenzene (100 mg, 0.46 mmol) in ethanol (5 ml), Tin (II) chloride (520 mg, 2.3 mmol) was added. The reaction mixture was stirred at room temperature for 16 hours. The NaHCO$_3$ (aq) was added to pH=7. Then was extracted with ethyl acetate (3x). The combined organic layer was dried over MgSO$_4$, filtered and concentrated under reduced pressure to give desired product (80 mg, 93%). EI-MS m/z 191 (M$^+$).

c) N-[4-chloro-2-hydroxy-3-(aminosulfonyl)phenyl]-N'(2-bromo-3-fluorophenyl) urea To a solution of 2-bromo-3-fluoroaniline (42 mg, 0.0.22 mmol) in toluene (5 mL), triphosgene (26 mg, 0.09 mmol) and triethyl amine (0.04 mL, 0.26 mmol) were added. The reaction mixture was stirred at 80° C. for 4 hours. Then the reaction mixture was concentrated under reduced pressure and then it was added to 3-amino-6-chloro-2-hydroxybenzenesulfonamide (44 mg, 0.22 mmol) in DMF (1 mL), The reaction mixture was stirred at room temperature for 16 hours. Chromatography of the resulting liquid on silica gel (30%Ethyl acetate/Hexane) gave desired product (7 mg, 7%). EI-MS m/z 439.6 ($M^+$).

Example 153, 154 and 155

Preparation of N-(2-bromophenyl)-N'-[4-chloro-3-[(1-ethyl-pyrrolidin-2-yl)methylaminosulfonyl]-2-hydroxyphenyl] urea hydrochloride, N-[4-chloro-3-[( 1-ethyl-pyrrolidin-2-yl)methylaminosulfonyl]-2-hydroxyphenyl]N'-(2,3-dichlorophenyl) urea hydrochloride and N-[4-chloro-3-[(1-ethyl-pyrrolidin-2-yl)methylaminosulfonyl]-2-hydroxyphenyl]-N'-(2-chlorophenyl) urea hydrochloride N-[(1-ethyl-pyrrolidin-2-yl)methyl]-2,6-dichloro-3-nitrobenzenesulfonamide Following the general procedure for sulfonamide formation outlined in example 15, 2,6-dichloro-3-nitrobenzenesulfonyl chloride (2.0 g, 6.88 mmol), 2-aminomethyl- 1-ethyl-pyrolidine (882 mg, 6.88 mmol) and triethylamine(1.92 mL, 13.76 mmol) were reacted. The crude product (2.64 g) was carried on to the next step without purification. LC-MS (m/z) 382.0 ($M^+$).

N-[(1-ethyl-pyrrolidin-2-yl)methyl]-6-chloro-2-hydroxy-3-nitrobenzenesulfonamide Following the general hydrolysis procedure outlined in example 15, crude N-[(l-ethyl-pyrrolidin-2-yl)methyl]-2,6-dichloro-3-nitrobenzenesulfonamide (1.50 g), 60% NaH (471 mg, 11.78 mmol) and water (85 µL, 4.72 mmol) were reacted to form the crude product (1.98 g), which was carried on to the next step without purification. LC-MS (m/z) 364.2 ($M^+$).

N-[(1-ethyl-pyrrolidin-2-yl)methyl]-3-amino-6-chloro-2-hydroxybenzenesulfonamide Following the general hydrogenation procedure outlined in example 15, crude N-[(l-ethyl-pyrrolidin-2-yl)methyl]-6-chloro-2-hydroxy-3-nitrobenzenesulfonamide (2.18 g) was reduced with hydrogen and 10% Pd/C (300 mg). The crude product (1.85 g) was carried on to the next step without purification.

N-(2-bromophenyl)-N'-[4-chloro-3-[(1-ethyl-pyrrolidin-2-yl)methylaminosulfonyl]-2-hydroxyphenyl] urea hydrochloride Following the general procedure for urea formation outlined in example 15, crude N'-(1-ethyl-pyrrolidin-2-yl)methyl]-3-amino-6-chloro-2-hydroxybenzene-sulfonamide (616 mg) and 2-bromophenylisocyanate (176 mg, 0.89 mmol) were coupled to form the desired urea (14 mg, 3% for 4 steps). LC-MS (m/z) 533.0 ($M^+$)

N-[4-chloro-3-[(]-ethyl-pyrrolidin-2-yl)methylaminosulfonyl]-2-hydroxyphenyl]N'-(2,3-dichlorophenyl) urea hydrochloride Following the general procedure for urea formation outlined in example 15, crude N-[(1-ethyl-pyrrolidin-2-yl)methyl]-3-amino-6-chloro-2-hydroxybenzene-sulfonamide (616 mg) and 2,3-dichlorophenylisocyanate (167 mg, 89 mmol) were coupled to form the desired urea (13 mg, 2.3% for 4 steps). LC-MS (m/z) 523.2 ($M^+$)

N-[4-chloro-3-[(1-ethyl-pyrrolidin-2-yl)methylaminosulfonyl]-2-hydroxyphenyl]-N'-(2-chlorophenyl) urea hydrochloride Following the general procedure for urea formation outlined in example 15, crude N-[(1-ethyl-pyrolidin-2-yl)methyl]-3-amino-6-chloro-2-hydroxybenzene-sulfonamide (410 mg) and 2-chlorophenylisocyanate (249 mg, 1.62 mmol) were coupled to form the desired urea (50 mg, 9.6% for 4 steps). LC-MS (m/z) 487.2 ($M^+$)

METHOD OF TREATMENT

The compounds of Formula (I), or a pharmaceutically acceptable salt thereof can be used in the manufacture of a medicine for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL-8 α or β receptor, also referred to as the type I or type II receptor.

Accordingly, the present invention provides a method of treating a chemokine mediated disease, wherein the chemokine is one which binds to an IL-8 α or β receptor and which method comprises administering an effective amount of a compound of Formula (I) or a pharmaceutically acceptable salt thereof. In particular, the chemokines are IL-8, GROα, GROβ, GROγ, NAP-2 or ENA-78.

The compounds of Formula (I) are administered in an amount sufficient to inhibit cytokine function, in particular IL-8, GROα, GROβ, GROγ, NAP-2 or ENA-78, such that they are biologically regulated down to normal levels of physiological function, or in some case to subnormal levels, so as to ameliorate the disease state. Abnormal levels of IL-8, GROα, GROβ, GROγ, NAP-2 or ENA-78 for instance in the context of the present invention, constitute: (i) levels of free IL-8 greater than or equal to 1 picogram per mL; (ii) any cell associated IL-8, GROα, GROβ, GROγ, NAP-2 or ENA-78 above normal physiological levels; or (iii) the presence of IL-8, GROα, GROβ, GROγ, NAP-2 or ENA-78 above basal levels in cells or tissues in which IL-8, GROα, GROβ, GROγ, NAP-2 or ENA-78 respectively, is produced.

The compounds of Formula (I), in generally have been shown to have a longer $t_{1/2}$ and improved oral bioavailabilty over the compounds disclosed in WO 96/25157 and WO 97/29743 whose disclosures are incorporated herein by reference.

There are many disease states in which excessive or unregulated IL-8 production is implicated in exacerbating and/or causing the disease. Chemokine mediated diseases include psoriasis, atopic dermatitis, osteo arthritis, rheumatoid arthritis, asthma, chronic obstructive pulmonary disease, adult respiratory distress syndrome, inflammatory bowel disease, Crohn's disease, ulcerative colitis, stroke, septic shock, multiple sclerosis, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, angiogenesis, atherosclerosis, osteoporosis, gingivitis and undesired hematopoietic stem cells release and diseases caused by respiratory viruses, herpesyiruses, and hepatitis viruses, meningitis, herpes encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, uveitis, polymyositis, vasculitis, acne, gastric and duodenal ulcers, celiac disease, esophagitis, glossitis, airflow obstruction, airway hyperresponsiveness, bronchiolitis obliterans organizing pneumonia, bronchiectasis, bronchiolitis, bronchiolitis obliterans, chronic bronchitis, cor pulmonae, dyspnea, emphysema, hypercapnea, hyperinflation, hypoxemia, hypoxia, surgerical lung volume reduction, pulmonary fibrosis, pulmonary hypertension, right ventricular hypertropy, sarcoidosis, small airway disease, ventilation-perfusion mismatching, wheeze and lupus.

These diseases are primarily characterized by massive neutrophil infiltration, T-cell infiltration, or neovascular growth, and are associated with increased IL-8, GROα, GROβ, GROγ, NAP-2 or ENA-78 production which is responsible for the chemotaxis of neutrophils into the inflammatory site or the directional growth of endothelial cells. In contrast to other inflammatory cytokines (IL-1, TNF, and IL-6), IL-8, GROα, GROβ, GROγ, NAP-2 or ENA-78 have the unique property of promoting neutrophil chemotaxis, enzyme release including but not limited to elastase release as well as superoxide production and activation. The α-chemokines but particularly, GROα, GRO,, GROγ, NAP-2 or ENA-78, working through the IL-8 type I or II receptor can promote the neovascularization of tumors by promoting the directional growth of endothelial cells. Therefore, the inhibition of IL-8 induced chemotaxis or activation would lead to a direct reduction in the neutrophil infiltration.

Recent evidence also implicates the role of chemokines in the treatment of HIV infections, Littleman et al., *Nature* 381, pp. 661 (1996) and Koup et al., *Nature* 381, pp. 667 (1996).

Present evidence also indicates the use of IL-8 inhibitors in the treatment of atherosclerosis. The first reference, Boisyert et al., *J. Clin. Invest,* 1998, 101:353–363 shows, through bone marrow transplantation, that the absence of IL-8 receptors on stem cells (and, therefore, on monocytes/macrophages) leads to a reduction in the development of atherosclerotic plaques in LDL receptor deficient mice. Additional supporting references are: Apostolopoulos, et al., *Arterioscier. Thromb. Vasc. Biol.* 1996, 16:100714 1012; Liu, et al., *Arterioscier. Thromb. Vasc. Biol,* 1997, 17:317–323; Rus, et al., *Atherosclerosis.* 1996, 127:263–271.; Wang et al., *J. Biol. Chem.* 1996, 271:8837–8842; Yue, et al., *Eur. J. Pharmacol.* 1993, 240:81–84; Koch, et al., *Am. J. Pathol.,* 1993, 142:1423–1431.; Lee, et al., *Immunol. Lett.,* 1996, 53, 109–113.; and Terkeltaub et al., *Arterioscier. Thromb.,* 1994, 14:47–53.

The present invention also provides for a means of treating, in an acute setting, as well as preventing, in those individuals deemed susceptible to, CNS injuries by the chemokine receptor antagonist compounds of Formula (I).

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this area has been emerging and the present invention provides a mean for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., *Stroke, Vol.* 25., No. 7, pp. 1481–88 (1994) whose disclosure is incorporated herein by reference.

Models of closed head injuries and treatment with mixed 5-LO/CO agents is discussed in Shohami et al., *J. of Vaisc & Clinical Physiology and Pharmacology, Vol.* 3, No. 2, pp. 99–107 (1992) whose disclosure is incorporated herein by reference. Treatment, which reduced edema formation, was found to improve functional outcome in those animals treated.

The compounds of Formula (I) are administered in an amount sufficient to inhibit IL-8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown to be inhibitors of type II IL-8 receptors.

As used herein, the term "IL-8 mediated disease or disease state" refers to any and all disease states in which IL-8, GROα, GROβ, GROγ, NAP-2 or ENA-78 plays a role, either by production of IL-8, GROα, GROβ, GROγ, NAP-2 or ENA-78 themselves, or by IL-8, GROα, GROD, GROγ, NAP-2 or ENA-78 causing another monokine to be released, such as but not limited to IL-1, IL-6 or TNF. A disease state in which, for instance, IL-1 is a major component, and whose production or action, is exacerbated or secreted in response to IL-8, would therefore be considered a disease state mediated by IL-8.

As used herein, the term "chemokine mediated disease or disease state" refers to any and all disease states in which a chemokine which binds to an IL-8 α or β receptor plays a role, such as but not limited to IL-8, GRO-α, GRO-β, GROγ, NAP-2 or ENA-78. This would include a disease state in which, IL-8 plays a role, either by production of IL-8 itself, or by IL-8 causing another monokine to be released, such as but not limited to IL-I, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule, which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to IL-8, GRO-α, GRO-β, GRO-γ, NAP-2, ENA-78, IP-10, MIP-1α, MIP-β, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% wlw but preferably will comprise less than 5% wlw, more preferably from 0. 1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil. Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I) the daily oral dosage regimen will preferably be from about 0.01 to about 80 mg/kg of total body weight.

The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The IL-8, and GRO-α chemokine inhibitory effects of compounds of the present invention are determined by the following in vitro assay:

Receptor Binding Assays

[$^{125}$I] IL-8 (human recombinant) is obtained from Amersham Corp., Arlington Heights, Ill. with specific activity 2000 Ci/mmol. GRO-α is obtained from NE N New England Nuclear. All other chemicals are of analytical grade. High levels of recombinant human IL-8 type α and β receptors were individually expressed in Chinese hamster ovary cells as described previously (Holmes, et aL., Science, 1991, 253, 1278). The Chinese hamster ovary membranes were homogenized according to a previously described protocol (Haour, et al., J. Biol. Chem., 249 pp 2195–2205 (1974)). Except that the homogenization buffer is changed to 10 mM Tris-HCL, 1 mM $MgSO_4$, 0.5mM EDTA (ethylene- diaminetetra-acetic acid), 1 mM PMSF (α-toluenesulphonyl fluoride), 0.5 mg/L Leupeptin, pH 7.5. Membrane protein concentration is determined using Pierce Co. micro-assay kit using bovine serum albumin as a standard. All assays are performed in a 96-well micro plate format. Each reaction mixture contains $^{125}$I IL-8 (0.25 nM) or $^{125}$I GRO-α and 0.5 pg/mL of IL-8Rα or 1.0 μg/mL of IL-8Rβ membranes in 20 mM Bis-Trispropane and 0.4 mM Tris HCl buffers, pH 8.0, containing 1.2 mM $MgSO_4$, 0.1 mM EDTA, 25 mM Na and 0.03% CHAPS. In addition, drug or compound of interest is added which has been pre-dissolved in DMSO so as to reach a final concentration of between 0.01 nM and 100 μM. The assay is initiated by addition of $^{125}$I-IL-8. After 1 hour at room temperature the plate is harvested using a Tomtec 96well harvester onto a glass fiber filtermat blocked with 1% polyethylenimine/0.5% BSA and washed 3 times with 25 mM NaCl, 10 mM TrisHCl, 1 mM $MgSO_4$, 0.5 mM EDTA, 0.03% CHAPS, pH 7.4. The filter is then dried and counted on the Betaplate liquid scintillation counter. The recombinant IL-8Rα, or Type I, receptor is also referred to herein as the non-permissive receptor and the recombinant IL-8 Rβ, or Type II, receptor is referred to as the permissive receptor.

Representative compounds of Formula (I), Examples 1 to 106 have exhibited positive inhibitory activity in this assay at $IC_{50}$ levels <30 μM.

Chemotaxis Assay

The in vitro inhibitory properties of these compounds are determined in the neutrophil chemotaxis assay as described in Current Protocols in Immunology, vol. I, Suppl 1, Unit 6.12.3., whose disclosure is incorporated herein by reference in its entirety. Neutrophils where isolated from human blood as described in Current Protocols in Immunology Vol. I, Suppl I Unit 7.23.1, whose disclosure is incorporated herein by reference in its entirety. The chemoattractants IL-8, GRO-α, GRO-β, GRO-β and NAP-2 are placed in the bottom chamber of a 48 multiwell chamber (Neuro Probe, Cabin John, MD) at a concentration between 0.1 and 100 nM. The two chambers are separated by a 5 μM polycarbonate filter. When compounds of this invention are tested, they are mixed with the cells (0.001–1000 nM) just prior to the addition of the cells to the upper chamber. Incubation is allowed to proceed for between about 45 and 90 min at about 37° C. in a humidified incubator with 5% $CO_2$. At the end of the incubation period, the polycarbonate membrane is removed and the top side washed, the membrane then stained using the Diff Quick staining protocol (Baxter Products, McGaw Park, Ill. USA). Cells which have chemotaxed to the chemokine are visually counted using a microscope. Generally, four fields are counted for each sample, these numbers are averaged to give the average number of cells which had migrated. Each sample is tested in triplicate and each compound repeated at least four times. To certain cells (positive control cells) no compound is added, these cells represent the maximum chemotactic response of the cells. In the case where a negative control (unstimulated) is desired, no chemokine is added to the bottom chamber. The difference between the positive control and the negative control represents the chemotactic activity of the cells.

Elastase Release Assay

The compounds of this invention are tested for their ability to prevent Elastase release from human neutrophils. Neutrophils are isolated from human blood as described in Current Protocols in Immunology Vol. I, Suppl 1 Unit 7.23.1. PMNs $0.88 \times 10^6$ cells suspended in Ringer's Solution (NaCl 118, KCl 4.56, $NaHCO_3$ 25, $KH_2PO_4$ 1.03, Glucose 11.1 HEPES 5 mM, pH 7.4) are placed in each well of a 96 well plate in a volume of 50 μl. To this plate is added the test compound (0.001–1000 nM) in a volume of 50 μl, Cytochalasin B in a volume of 50 μl (20 ug/ml) and Ringers buffer in a volume of 50 μl. These cells are allowed to warm (37° C., 5% CO2, 95% RH) for 5 min before IL-8, GROα, GROβ, GROγ or NAP-2 at a final concentration of 0.01–1000 nM was added. The reaction is allowed to proceed for 45 min before the 96 well plate is centrifuged (800 xg 5 min.) and 100 μl of the supernatant removed. This supernatant is added to a second 96 well plate followed by an artificial elastase substrate (MeOSuc-Ala-Ala-Pro-Val-AMC, Nova Biochem, La Jolla, Calif.) to a final concentration of 6 ug/ml dissolved in phosphate buffered saline. Immediately, the plate is placed in a fluorescent 96 well plate reader (Cytofluor 2350, Millipore, Bedford, Mass.) and data collected at 3 min intervals according to the method of Nakajima et al J. Biol. Chem. 254 4027 (1979). The amount of Elastase released from the PMNs is calculated by measuring the rate of MeOSuc-Ala-Ala-Pro-Val-AMC degradation.

TNF-α in Traumatic Brain Injury Assay

The present assay provides for examination of the expression of tumor necrosis factor mRNA in specific brain regions, which follow experimentally, induced lateral fluid-percussion traumatic brain injury (TBI) in rats. Adult Sprague-Dawley rats (n=42) were anesthetized with sodium pentobarbital (60 mg/kg, i.p.) and subjected to lateral fluid-percussion brain injury of moderate severity (2.4 atm.) centered over the left temporaparietal cortex (n=8), or "sham" treatment (anesthesia and surgery without injury, n=18). Animals are sacrificed by decapitation at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA are isolated and Northern blot hybridization is performed and quantitated relative to an TNF-α positive control RNA (macrophage=100%). A marked increase of TNF-α mRNA expression is observed in LH (104±17% of positive control, p <0.05 compared with sham), LC (105±21%, p<0.05) and LA (69±8%, p<0.01) in the traumatized hemisphere 1 hr. following injury. An increased TNF-α mRNA expression is also observed in LH (46±8%, p <0.05), LC (30±3%, p<0.01) and LA (32±3%, p<0.01) at 6 hr which resolves by 24 hr following injury. In the contralateral hemisphere, expression of TNF-α mRNA is increased in RH (46±2%, p<0.01), RC (4±3%) and RA (22±8%) at 1 hr and in RH (28±11%), RC (7±5%) and RA (26±6%, p<0.05) at 6 hr but not at 24 hr following injury. In sham (surgery without injury) or naive animals, no consistent changes in expression of TNF-α mRNA are observed in any of the 6 brain areas in either hemisphere at any times. These results indicate that following parasagittal fluid-percussion brain injury, the temporal expression of TNF-α mRNA is altered in specific brain regions, including those of the non-traumatized hemisphere. Since TNF-a is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury model for IL-1β mRNA

This assay characterizes the regional expression of interleukin-1β (IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals are sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization was performed and the quantity of brain tissue IL-1β mRNA is presented as percent relative radioactivity of IL-1β positive macrophage RNA which was loaded on the same gel. At 1 hr following brain injury, a marked and significant increase in expression of IL-1β mRNA is observed in LC (20.0±7% of positive control, n=6, p<0.05 compared with sham animal), LH (24.5±9%, p<0.05) and LA (21.5±3.1%, p<0.05) in the injured hemisphere, which remained elevated up to 6 hr. post injury in the LC (4.0±4%, n=6, p<0.05) and LH (5.0±1.3%, p<0.05). In sham or naive animals, no expression of IL-1β mRNA is observed in any of the respective brain areas. These results indicate that following TBI, the temporal expression of IL-1β mRNA is regionally stimulated in specific brain regions. These regional changes in cytokines, such as IL-1β play a role in the post-traumatic.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is.

1. A compound of the formula (I):

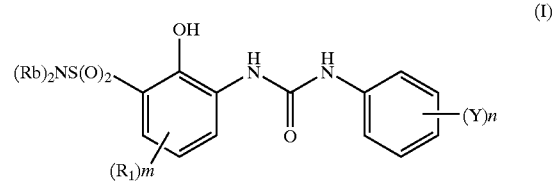

wherein $R_b$ is independently hydrogen, $NR_6NR_7$, OH $OR_a$, $C_{1-5}$alkyl, aryl, aryl$C_{1-4}$alkyl, aryl$C_{2-4}$alkenyl; cycloalkyl, cycloalkyl$C_{1-5}$alkyl, heteroaryl, heteroaryl$C_{1-4}$alkyl, heteroaryl$C_{2-4}$alkenyl, heterocyclic, heterocyclic $C_{1-4}$alkyl, or a heterocyclic $C_{2-4}$alkenyl moiety, all of which moieties may be optionally substituted one to three times independently by halogen; nitro, halosubstituted $C_{1-4}$alkyl; $C_{1-4}$alkyl; amino; mono or di-$C_{1-4}$alkyl substituted amine; $OR_a$; $C(O)R_a$; $NR_aC(O)OR_a$; $OC(O)NR_6R_7$; hydroxy; $NR_9C(O)R_a$; $S(O)_mR_a$; $C(O)NR_6R_7$; $C(O)OH$; $C(O)OR_a$; $S(O)_tNR_6R_7$; $NHS(O)_tR_a$; or the two $R_b$ substituents join to form either an optionally unsaturated 3–10 membered cycloalkyl ring or a 3–10 membered heterocyclic ring containing, independently, 1 to 3 $NR_a$, O, S, SO, or $SO_2$ moieties;

$R_a$ is an alkyl, aryl, aryl$C_{1-4}$alkyl, heteroaryl, heteroaryl $C_{1-4}$alkyl, heterocyclic, $COOR_a$,' or a heterocyclic $C_{1-4}$alkyl moiety, all of which moieties may be optionally substituted;

$R_a$' is an alkyl, aryl, aryl$C_{1-4}$alkyl, heteroaryl, heteroaryl $C_{1-4}$alkyl, heterocyclic or a heterocyclic $C_{1-4}$alkyl moiety, all of which moieites may be optionally substituted;

m is an integer having a value of 1 to 3;

m' is an integer having a value of 1 to 2;

n is an integer having a value of 1 or 3;

q is 0, or an integer having a value of 1 to 10;

t is 0, or an integer having a value of 1 to 2;

s is an integer having a value of 1 to 3;

$R_1$ is independently selected from hydrogen, halogen, nitro, cyano, $C_{1-10}$ alkyl, halosubstituted $C_{1-10}$ alkyl, $C_{2-10}$alkenyl, $C_{1-10}$alkoxy, halosubstituted $C_{1-10}$alkoxy, azide, $S(O)_tR_4$, $(CR_8R_8)_q$ $S(O)_tR_4$, hydroxy, hydroxy substituted $C_{1-4}$alkyl, aryl, aryl $C_{1-4}$alkyl, aryl $C_{2-10}$alkenyl, aryloxy, aryl $C_{1-4}$ alkyloxy, heteroaryl, heteroarylalkyl, heteroaryl $C_{2-10}$ alkenyl, heteroaryl $C_{1-4}$ alkyloxy, heterocyclic, heterocyclic $C_{1-4}$alkyl, heterocyclic$C_{1-4}$alkyloxy, heterocyclic$C_{2-10}$ alkenyl, $(CR_8R_8)q\ NR_4R_5$, $(CR_8R_8)qC(O)NR_4R_5$, $C_{2-10}$ alkenyl $C(O)NR_4R_5$, $(CR_8R_8)q\ C(O)NR_4R_{10}$, $S(O)_3R_8$, $(CR_8R_8)q\ C(O)R_{11}$, $C_{2-10}$ alkenyl $C(O)R_{11}$, $C_{2-10}$alkenyl $C(O)OR_{11}$, $(CR_8R_8)q\ C(O)OR_{11}$, $(CR_8R_8)q\ OC(O)R_{11}$, $(CR_8R_8)qNR_4C(O)R_{11}$, $(CR_8R_8)q\ C(NR_4)NR_4R_5$, $(CR_8R_8)q\ NR_4C(NR_5)R_{11}$, $(CR_8R_8)q\ NHS(O)_rR_{13}$, $(CR_8R_8)q\ S(O)_rNR_4R_5$, or two $R_1$ moieties together may form O—$(CH_2)_s$O or a 5 to 6 membered saturated or unsaturated ring, and wherein the alkyl, aryl, arylalkyl, heteroaryl, heterocyclic moieties may be optionally substituted;

$R_4$ and $R_5$ are independently hydrogen, optionally substituted $C_{1-4}$alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$alkyl, or $R_4$ and $R_5$ together with the nitrogen to which they are attached form a 5 to 7 member ring optionally containing an additional heteroatom selected from oxygen, nitrogen, and sulphur;

$R_6$ and $R_7$ are independently hydrogen, or a $C_{1-4}$ alkyl, heteroaryl, aryl, aklyl aryl, alkyl $C_{1-4}$heteroalkyl, which may all be optionally substituted or $R_6$ and $R_7$ together with the nitrogen to which they are attached form a 5 to 7 member ring which ring may optionally contain an additional heteroatom is selected from oxygen, nitrogen or sulfur, and which ring may be optionally substituted;

Y is hydrogen, halogen, nitro, cyano, halosubstituted $C_{1-10}$ alkyl, $C_{1-10}$ alkyl, $C_{2-10}$ alkenyl, $C_{1-10}$ alkoxy, halosubstituted $C_{1-10}$ alkoxy, azide, $(CR_8R_8)qS(O)_rR_a$, $(CR_8R_8)OR_a$, hydroxy, hydroxy substituted $C_{1-4}$alkyl, aryl; aryl $C_{1-4}$ alkyl, aryloxy, aryl$C_{1-4}$alkyloxy, aryl$C_{2-10}$ alkenyl, heteroaryl, heteroarylalkyl, heteroaryl $C_{1-4}$ alkyloxy, heteroaryl $C_{2-10}$ alkenyl, heterocyclic, heterocyclic $C_{1-4}$alkyl, heterocyclic$C_{2-10}$ alkenyl, $(CR_8R_8)qNR_4R_5$, $C_{2-10}$ alkenyl $C(O)NR_4R_5$, $(CR_8R_8)qC(O)NR_4R_5$, $(CR_8R_8)qC(O)NR_4R_{10}$, $S(O)_3R_8$, $(CR_8R_8)qC(O)R_{11}$, $C_{2-10}$alkenyl$C(O)R_{11}$, $(CR_8R_8)qC(O)OR_{11}$, $C_{2-10}$alkenyl$C(O)OR_{11}$, $(CR_8R_8)qOC(O)R_{11}$, $(CR_8R_8)qNR_4C(O)R_{11}$, $(CR_8R_8)q\ NHS(O)_rR_{13}$, $(CR_8R_8)q\ NHS(O)_rR_{13}$, $(CR_8R_8)q\ S(O)_rNR_4R_5$, $(CR_8R_8)qC(NR_4)R_5$, $(CR_8R_8)q\ NR_4C(NR_5)R_{11}$, or two Y moieties together may form O—$(CH_2)_s$—O or a 5 to 6 membered saturated or unsaturated ring, and wherein the alkyl, aryl, arylalkyl, heteroaryl, heteroaryl alkyl, heterocyclic, heterocyclicalkyl groups may be optionally substituted;

$R_8$ is hydrogen or $C_{1-4}$ alkyl;

$R_9$ is hydrogen or a $C_{1-4}$alkyl;

$R_{10}$ is $C_{1-10}$ alkyl $C(O\ )_2R_8$;

$R_{11}$ is hydrogen, optionally substituted $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$ alkyl;

$R_{13}$ is selected from the group consisting of $C_{1-4}$ alkyl, aryl, aryl $C_{1-4}$alkyl, heteroaryl, heteroaryl$C_{1-4}$alkyl, heterocyclic, and heterocyclic$C_{1-4}$alkyl; or a pharmaceutically acceptable salt thereof.

2. The compound according to claim 1 wherein $R_1$ represents a substitution at the 4-position by a moiety selected from the group consisting of halogen, nitro, cyano, azide, aryl, aryl$C_{1-4}$ alkyl, aryl $C_{2-10}$ alkenyl, aryloxy, heteroaryl, $C(O)NR_4R_5$ and $C(O)R_{11}$.

3. The compound according to claim 2 wherein $R_1$ is halogen, cyano or nitro.

4. The compound according to claim 3 wherein $R_1$ is halogen.

5. The compound according to claim 4 wherein $R_1$ is independently, fluorine, chlorine, or bromine.

6. The compound according to claim 1 wherein Y either represents a mono-substitution at the 2'-position or 3'-position, or represents a di-substitution at both the 2'- and 3'- position.

7. The compound according to claim 6 wherein Y is halogen.

8. The compound according to claim 4 wherein Y is independently fluorine, chlorine, or bromine.

9. The compound according to claim 1 wherein $R_b$ is hydrogen, $C_{1-4}$alkyl, or $C_{1-4}$alkyl substituted with $C(O)OH$, or $C(O)OR_a$.

10. The compound according to claim 1 wherein Y is halogen, n is 1 or 2, $R_1$ is halogen, m is 1 or 2, and $R_b$ is, independently, hydrogen, $C_{1-4}$ alkyl, $C_{1-4}$ alkyl substituted with $C(O)OH$, or $C(O)OR_a$.

11. The compound according to claim 1 which is selected from the group consisting of:

N-(2-Hydroxyl-3-aminosulfonyl-4-chlorophenyl)-N'-(2-bromophenyl)urea;

N-(2-Hydroxy-3-aminosulfonyl-4-chlorophenyl)-N'-(2,3-bromophenyl)urea;

N-(2-Hydroxy-3N"-benzylaminosulfonyl-4-chlorophenyl)-N'-(2-bromophenyl)urea;

N-(2-Hydroxy-3N"-benzylaminosulfonyl-4-chlorophenyl)-N'-(2,3-chlorophenyl)urea;

N-(2-Hydroxy-3N",N"-dimethyl)-aminosulfonyl-4-chlorophenyl)-N'-(2,3-dichlorophenyl) urea;

N-(2-Hydroxy-3N",N"-dimethylaminosulfonyl-4-chlorophenyl)-N'-(2-bromophenyl) urea;

N-(2-Hydroxy-3N"-methylaminosulfonyl-4-chlorophenyl)-N'-(2-bromophenyl) urea;

N-(2-Hydroxy-3N"-methylaminosulfonyl-4-chlorophenyl)-N'-(2,3-dichlorophenyl) urea;

N-[2-Hydroxy-3[N-methoxycarbonylmethyl)aminosulfonyl]-4-cholorphenyl]-N'-(2,3-dichlorophenyl) urea;

N-[2-Hydroxy-3-(N-methoxycarbonyl)-methyl)-aminosulfonyl-4-cholorphenyl]-N'-(2-dichlorophenyl) urea;

N-[2-Hydroxy-3-[(N"-carboxymethyl)-aminosulfonyl]-4-cholorphenyl]-N'-(2,3-dichlorophenyl)

N-[2-Hydroxy-3-[(N"-carboxymethyl)-aminosulfonyl-4-cholorphenyl]-N'-(2-dichlorophenyl) urea;

N-[2-Hydroxy-3-aminosulfonyl-4-cholorphenyl]-N'-(2-chlorophenyl) urea;

N-[2-Hydroxy-3-aminosulfonyl-4-cholorphenyl]-N'-phenyl urea;

N-(2-Hydroxy-3-aminosulfonyl-4-cholorphenyl]-N'(2-phenoxyphenyl urea;

N-(2-Hydroxy-3-[N"-carboxyethyl)aminosulfonyl]-4-cholorphenyl]-N'(2-bromophenyl) urea;

N-[2-Hydroxy-3-(isopropylaminosulfonyl-4-cholorphenyl]-N'(2-bromophenyl) urea;

N-[2-Hydroxy-3-(isopropylaminosulfonyl-4-cholorphenyl]-N'(2-chlorophenyl) urea;

N-[2-Hydroxy-3-(isopropylaminosulfonyl-4-cholorphenyl]-N'(2,3-dichlorophenyl) urea;

N-4-chloro-2-hydroxy-3-aminosulfonylphenyl-N'(2-methoxyphenyl) urea;

N-4-chloro-2-hydroxy-3-aminosulfonylphenyl-N'(2,3-methylenedioxy phenyl) urea;

N-(2-benzyloxphenyl)-N'-(4-chloro-2-hydroxy-3-aminosulfonylphenyl) urea;

N-[3(N"-allylaminosulfonyl)-4-2-hydroxyphenyl]-N'-2,3-dichlorophenyl)urea;

N-[4-chloro-2-hydroxy-3-[N"-(2-trifluoroethyl) aminosulfonyl]phenyl]-N'-2,3-dichlorophenyl) urea;

N-(2,3-dichlorophenyl)-N'-[2-hydroxy-4-methoxy-3-N"-(phenylaminosulfonyl)phenyl] urea;

N-(2-bromophenyl)-N'-[2-hydroxy-4-methoxy-3-N"-(phenylaminosulfonyl)phenyl] urea;

N-[4-chloro-2-hydroxy-3-[N"-(2-methoxyethyl) aminosulfonyl]phenyl]N'-(2,3-dichlorophenyl) urea;

N-(2-bromophenyl)-N'-[4chloro-2-hydroxy-3-[N'-(2-methoxyethyl)aminosulfonyl]phenyl] urea;

N-(2-bromophenyl)-N'-[4-chloro-2-hydroxy-3-(4morpholinylsulfonyl)phenyl] urea;

N-[4-chloro-2-hydroxy-3-(4-morpholinylsulfonyl)phenyl]-N'-(2,3-dichlorophenyl) urea;

N-[3[N"-[3-(tert-butoxycarbonylamino)propyl] aminosulfonyl]-4-chloro-2-hydroxyphenyl]-N'-(2,3-dichlorophenyl) urea;

N-(2-bromophenyl)-N'-[3-[N"-[3-(tert-butoxycarbonylamino)propyl]aminosulfonyl]-4-chloro-2-hydroxyphenyl] urea;

N-[3-[N"-(3-aminopropyl)aminosulfonyl]-4-chloro-2-hydroxyphenyl]-N'-(2bromophenyl) urea trifluoroacetate;

N-[3-[N"-(3-aminopropyl)aminosulfonyl]-4-chloro-2-hydroxyphenyl]-N'-(2-bromophenyl) urea hydrochloride;

N-[3-[N"-(3-aminopropylaminosulfonyl]-4-chloro-2-hydroxyphenyl]-N'-(2,3-dichlorophenyl) urea trifluoroacetate;

N-(2-bromophenyl)-N'-[3-[N"-[2(tert-butoxycarbonylamino)ethyl]aminosulfonyl]-4-chloro-2-hydroxyphenyl] urea;

N-[3[N"-(2-aminoethyl)aminosulfonyl]-4-chloro-2-hydroxyphenyl]-N'-(2-bromophenyl) urea;

N-(2-bromophenyl)-N'-[3-[[4-(tert-butoxycarbonyl)-piperazin-1-yl]-sulfonyl]-4-chloro-2hydroxyphenyl] urea;

N-[3-[[4-(tert-butoxycarbonyl)piperazin-1-yl]sulfonyl]-4-chloro-2-hydroxyphenyl]-N'-(2,3-dichlorophenyl) urea;

N-[4-chloro-2-hydroxy-3-(1-piperazinylsulfonyl) phenyl]-N'-(2,3-dichlorophenyl) urea trifluoroacetate;

N-(2-bromophenyl)-N'-[4-chloro-2-hydroxy-3-(piperazin-1-ylsulfonyl)phenyl] urea trifluoroacetate;

N-[4-chloro-2-hydroxy-3-[N"-(3-methylthiopropyl) aminosulfonyl]phenyl]-N'(2,3-dichlorophenyl) urea;

N-(2-bromophenyl)-N'[4-chloro-2-hydroxy-3-[N"-(3-methylthiopropyl)aminosulfonyl]phenyl] urea;

N-(4-chloro-2-hydroxy-3-aminosulfonylphenyl)-N'-(2,3-dichlorophenyl) urea potassium salt;

N-(4-chloro-2-hydroxy-3-aminosulfonylphenyl)-N'-(2,3-dichlorophenyl) urea sodium salt;

N-(2-bromophenyl)-N'-[4-chloro-3-[N",N"-di-(2-methoxyethyl)aminosulfonyl]-2-hydroxyphenyl] urea;

N-[4-chloro-3-[N",N"-di-(2-methoxyethyl) aminosulfonyl]-2-hydroxyphenyl]-N'-(2,3-dichlorophenyl) urea;

N-(2-bromophenyl)-N'-[4-chloro-3-[N"-[2-(dimethylamino)ethyl]aminosulfonyl]-2-hydroxyphenyl] urea hydrochloride;

N-[4-chloro-3-[N"-[2-(dimethylamino)ethyl] aminosulfonyl]-2-hydroxyphenyl]-N'(2,3-dichlorophenyl) urea hydrochloride;

N-[4-chloro-2-hydroxy-3-[N"-[3-(methylsulfonyl) propyl]aminosulfonyl]phenyl]-N'(2,3-dichlorophenyl) urea;

N-(2-bromophenyl)-N'-[4-chloro-2-hydroxy-3-[N"-[3-(methylsulfonyl)propyl]aminosulfonyl]phenyl] urea;

N-[4-chloro-2-hydroxy-3-[N"-[2-(morpholinyl)ethyl] aminosulfonyl]phenyl]-N'(2,3-dichlorophenyl) urea hydrochloride;

N-[4-chloro-2-hydroxy-3-[N"-[2-(morpholinyl)ethyl] aminosulfonyl]phenyl]-N'(2-chlorophenyl) urea hydrochloride;

N-(2-bromophenyl)-N'-[4-chloro-2-hydroxy-3-[N"-[2-(4-morpholinyl)ethyl]aminosulfonyl]phenyl] urea;

N-[4-chloro-2-hydroxy-3-(4-thiomorpholinylsulfonyl) phenyl]-N'(2,3-dichlorophenyl) urea;

N-(2-bromophenyl)-N'-[4-chloro-2-hydroxy-3-(4-thiomorpholinylsulfonyl)phenyl] urea;

N-(2-bromophenyl)-N '-[4-chloro-3-[N",N"-di-(2-hydroxyethyl)aminosulfonyl]-2-hydroxyphenyl] urea;

N-[4-chloro-3-[N",N"-di-(2-hydroxyethyl) aminosulfonyl]-2-hydroxyphenyl]-N'(2,3-dichlorophenyl) urea, N-[4-chloro-2-hydroxy-3-[N"-[3-(methylsulfinyl)propyl] aminosulfonyl]phenyl]-N'(2,3-dichlorophenyl) urea;

N-(2-bromophenyl) -N'-[4-chloro-2-hydroxy-3- [N "-[3-(methylsulfinyl)propyl]aminosulfonyl]phenyl] urea;

N-(2-bromophenyl)-N'-[3-[N"-[(1-tert-butoxycarbonylpiperidin-4-yl)methyl]aminosulfonyl]-4-chloro-2-hydroxyphenyl] urea, N-[3-[N"-[(1-tert-butoxycarbonylpiperidin-4-yl)methyl] aminosulfonyl]-4-chloro-2-hydroxyphenyl]-N'-(2,3-dichlorophenyl) urea;

N-[4-chloro-2-hydroxy-3-(1-oxidothiomorpholinosulfonyl)phenyl]-N'-(2,3-dichlorophenyl) urea;

N-(2-bromophenyl)-N'-[4-chloro-2-hydroxy-3-(1-oxidothiomorpholinosulfonyl)phenyl] urea;

N-[4-chloro-2-hydroxy-3-[N"-[(piperidin-4-yl)methyl] aminosulfonyl]phenyl]-N'(2,3-dichlorophenyl) urea trifluoroacetate;

N-(2-bromophenyl)-N'-[4-chloro-2-hydroxy-3-[N"-[(piperidin-4-yl)methyl]aminosulfonyl]phenyl] urea hydrochloride;

N-[3-(1-azetidinylsulfonyl)-4-chloro-2-hydroxyphenyl]-N'-(2-bromophenyl) urea;

N-[3-(1-azetidinylsulfonyl)-4-chloro-2-hydroxyphenyl]-N'L(2-chlorophenyl) urea;

N-[3-(1-azetidinylsulfonyl)-4-chloro-2-hydroxyphenyl]-N'(2,3-dichlorophenyl) urea;

N-(2-bromophenyl)-N'-[4-chloro-3-(N",N"-dimethylaminosulfonyl)-2-hydroxyphenyl] urea potassium salt;

N-(2-bromophenyl)-N'-[4-chloro-3-(N",N"-dimethylaminosulfonyl)-2-hydroxyphenyl] urea sodium salt;

N-(2-bromophenyl)-N'[4-chloro-3-(N"-cyclopropylaminosulfonyl)-2-hydroxyphenyl) urea;

N-[4-chloro-3-(N"-cyclopropylaminosulfonyl)-2-hydroxyphenyl]-N'(2-chlorophenyl) urea;

N-[4-chloro-3 -(N"-cyclopropylaminosulfonyl)-2-hydroxyphenyl]-N'-(2,3-dichlorophenyl) urea;

N-(2-bromophenyl)-N'4-chloro-2-hydroxy-3-(N"-propylaminosulfonyl)phenyl] urea;

N-[4-chloro-2-hydroxyl-3-(N"-propylaminosulfonyl)phenyl]-N(2,3-dichlorophenyl) urea;

N-[4-chloro-2-hydroxyl-3-(N"-propylaminosulfonyl)phenyl]-N'(2-chlorophenyl) urea;

N-(2-bromophenyl)-N'[4-chloro-3-(N"-ethylaminosulfonyl])-2-hydroxyphenyl] urea;

N-[4-chloro-3-(N"-ethylaminosulfonyl)-2-hydroxyphenyl]-N'-(2-chlorophenyl) urea;

N-[4-chloro-3-(N"-ethylaminosulfonyl)-2-hydroxyphenyl]-N'(2,3-dichlorophenyl) urea;

N-(2-bromophenyl)-N'-[3-[N"-[5-(tert-butoxycarbonylamino)-5-carboxypentyl]aminosulfonyl]-4-chloro-2-hydroxyphenyl] urea;

N-[3-[N"-[5-(tert-butoxycarbonylamino)-5-carboxypentyl]nosulfonyl]-4-chloro-2-hydroxyphenyl]-N'-(2,3-dichlorophenyl) urea;

N-[3-[N"-[5-(tert-butoxycarbonylamino)-5-carboxypentyl]aminosulfonyl]-4-chloro-2-hydroxyphenyl]-N'-(2-chlorophenyl) urea;

N-(2-bromophenyl)-N'[4-chloro-2-hydroxy-3-[N"-(2-hydroxyethyl)aminosulfonyl] urea;

N-(2,3-dichlorophenyl)-N'-[4-chloro-2-hydroxy-3-[N"-(2-hydroxyethyl)aminosulfonyl] urea;

N-(2-bromophenyl)-N'[3-[N"-[[(2-bromophenylamino)carboxyl]ethyl]aminosulfonyl]-4-chloro-2-hydroxyphenyl] urea;

N-[3-[N"-(2-benzyloxyethyl)aminosulfonyl]-4-chloro-2-hydroxyphenyl]-N'(2 bromophenyl) urea;

N-[2-Hydroxy-3-(N"-cyclopropylmethylaminosulfonyl)-4-chlorophenyl]-N'(2,3-dichlorophenyl) urea;

N-[2-Hydroxy-3-(N"-cyclopropylmethylaminosulfonyl)4-chlorophenyl]-N'-(2 chlorophenyl) urea;

N-[2-Hydroxy-3-(N"-cyclopropylmethylaminosulfonyl)-4-chlorophenyl]-N'-(2 bromophenyl) urea;

N-[2-Hydroxy-3-(N"-methoxy-N"-methylaminosulfonyl)-4-chlorophenyl]-N'(2-bromophenyl) urea;

N-[2-Hydroxy-3-(N"-methoxy-N"-methylaminosulfonyl)4-chlorophenyl]-N'(2 chlorophenyl) urea;

N-[2-Hydroxy-3-(N"-methoxy-N"-methylaminosulfonyl)-4-chlorophenyl]-N'(2,3 dichlorophenyl) urea;

N-[2-Hydroxy-3-(N"-pyrrolidinylsulfonyl)-4-chlorophenyl]-N'-(2,3-dichlorophenyl) urea;

N-[2-Hydroxy-3-(N"-pyrrolidinylsulfonyl)-4-chlorophenyl]-N'(2-bromophenyl) urea;

N-[2-Hydroxy-3-(N"-pyrrolidinylsulfonyl)-4-chlorophenyl]-N'(2-chlorophenyl) urea;

N-(2-bromophenyl)-N'-[4-chloro-2-hydroxy-3-[(4-pyridinylaminosulfonyl]phenyl] urea;

N-[4-chloro-2-hydroxy-3-[(4-pyridinylaminosulfonyl]phenyl]-N'(2,3-dichlorophenyl) urea;

N-(2-bromophenyl)-N'[4-chloro-2-hydroxy-3-[[[2-(tetrahydro-2-furanyl)methyl]aminosulfonyl]phenyl] urea;

N-[4-chloro-2-hydroxy-3-[[[2-(tetrahydro-2-furanyl)methyl]aminosulfonyl]phenyl]-N'-(2,3-dichlorophenyl) urea;

N-(2-bromophenyl)-N'-[4-chloro-2-hydroxy-3-[[[(2R)-(tetrahydro-2-furanyl)methyl]aminosulfonyl]phenyl] urea; and N-[4-chloro-2-hydroxy-3-[[[(2R)-(tetrahydro-2-furanyl)methyl]aminosulfonyl]phenyl]-N'-(2,3-dichlorophenyl) urea;

N-(2-bromophenyl)-N'-[4-chloro-2-hydroxy-3-[[[(2S)-(tetrahydro-2-furanyl)methyl]aminosulfonyl]phenyl] urea;

N-[4-chloro-2-hydroxy-3-[[[(2S)-(tetrahydro-2-furanyl)methyl]aminosulfonyl]phenyl]-N'-(2,3-dichlorophenyl) urea;

N-(2-bromophenyl)-N'-[4-chloro-2-hydroxy-3-(N"-cyclopentylaminosulfonyl)phenyl]urea;

N-[4-chloro-2-hydroxy-3-(N"-cyclopentylaminosulfonyl)phenyl]-N'-(2,3-dichlorophenyl)urea;

N-(2-chlorophenyl)-N'-4-chloro-2-hydroxy-3-(N"-cyclopentylaminosulfonyl)phenyl]urea;

N-(2-bromophenyl)-N'-[4-chloro-2-hydroxy-3 -(N"-isoxazolidinylaminosulfonyl) phenyl]urea;

N-[4-chloro-2-hydroxy-3-(N"-isoxazolidinylaminosulfonyl)phenyl]-N'-(2,3-dichlorophenyl)urea;

N-(2-chlorophenyl)-N'-[4-chloro-2-hydroxy-3-(N"-isoxazolidinylaminosulfonyl) phenyl]urea;

N-(2-bromophenyl)-N'-[4-chloro-2-hydroxy-3-(N"-tetrahydroisoxazylaminosulfonyl) phenyl]urea;

N-[4-chloro-2-hydroxy-3-(N"-tetrahydroisoxazylaminosulfonyl)phenyl]-N'(2,3-dichlorophenyl)urea;

N-(2-chlorophenyl)-N'-[4-chloro-2-hydroxy-3-N"-(tetrahydroisoxazylaminosulfonyl) phenyl]urea;

N-(2-bromophenyl)-N'-4-chloro-2-hydroxy-3-[(2-isopropoxyethyl)aminosulfonyl]phenyl] urea;

N-[4-chloro-2-hydroxy-3-[(2-isopropoxyethyl)aminosulfonyl phenyl]-N'(2,3-dichlorophenyl) urea;

N-[4-chloro-2-hydroxy-3-[(2-isopropoxyethyl)aminosulfonyl phenyl]-N'(2-chlorophenyl) urea;

N-(2-bromophenyl)-N'-[4-chloro-2-hydroxy-3-[(2-ethoxyethyl)aminosulfonyl]phenyl] urea;

N-[4-chloro-2-hydroxy-3-[(2-ethoxyethyl)aminosulfonyl]phenyl]-N'-(2,3-dichlorophenyl) urea;

N-[4-chloro-2-hydroxy-3-[(2-ethoxyethyl)aminosulfonyl]phenyl]-N'-(2-chlorophenyl) urea;

N-(2-bromophenyl)-N'-[4-chloro-2-hydroxy-3-[(2-methoxycarbonyl)azetidin-1-yl]sulfonylphenyl] urea;

N-[4-chloro-2-hydroxy-3-[(2-methoxycarbonyl)azetidin-1-yl]sulfonylphenyl]-N'-(2,3-dichlorophenyl) urea;

N-[4-chloro-2-hydroxy-3-[(2-carboxy)-azetidin-1-yl]sulfonylphenyl]-N'-(2,3-dichlorophenyl) urea;

N-(2-bromophenyl)-N'-[4-chloro-2-hydroxy-3-[N"-[3-(4-morpholinyl)propyl]aminosulfonyl]phenyl] urea hydrochloride;

N-[4-chloro-2-hydroxy-3-[N"-[3-(4-morpholinyl)propyl]-aminosulfonyl]phenyl]-N'2,3-dichlorophenyl) urea hydrochloride;

N-[4-chloro-2-hydroxy-3-[N"-[3-(4-moipholinyl)propyl]aminosulfonyl]phenyl]-N'(2-chlorophenyl) urea hydrochloride;

N-(2-bromophenyl)-N'-[4-chloro-2-hydroxy-3-[S-(−)-(2-methoxymethyl)pyrrolidin-1-yl]sulfonylphenyl] urea;

N-(2-bromophenyl)-N'-4-chloro-2-hydroxy-3-[S-(−)-(2-hydroxymethyl)pyrrolidin-1-yl]sulfonylphenyl] urea;

N-[4-chloro-2-hydroxy-3-[S-(−)-(2-methoxymethyl)pyrrolidin-1-yl]sulfonylphenyl]-N'-(2,3-dichlorophenyl) urea;

N-[4-chloro-2-hydroxy-3-[S-(−)-(2-hydroxymethyl)-pyrrolidin-1-ylsulfonyl]phenyl]-N'-(2,3-dichlorophenyl) urea;

N-[4-chloro-2-hydroxy-3-[S-(−)-(2-methoxymethyl)-pyrrolidin-1-yl]sulfonylphenyl]-N'-(2-chlorophenyl) urea;

N-[4-chloro-2-hydroxy-3-[S-(−)-(2-hydroxymethyl)-pyrrolidin-1-yl]sulfonylphenyl]-N'-(2-chlorophenyl) urea;

N-(2-bromophenyl)-N'-[4-chloro-2-hydroxy-3-[S-(2-methoxycarbonyl)pyrrolidin-1-yl]sulfonylphenyl] urea;

N-(2-bromophenyl)-N'-[4-chloro-2-hydroxy-3-[S-(2-carboxy)pyrrolidin-1-yl]sulfonylphenyl] urea;

N-(2-bromophenyl)-N'-[3-[N-(tert-butyl)aminosulfonyl]-4-chloro-2-hydroxyphenyl] urea;

N-[3-[N"-(tert-butyl)aminosulfonyl]-4-chloro-2-hydroxyphenyl]-N'(2,3-dichlorophenyl) urea;

N-[3-[N"-(tert-butyl)aminosulfonyl]-4-chloro-2-hydroxylphenyl]-N'(2-chlorophenyl) urea;

N-[3-[N"-[5-(tert-butoxycarbonylamino)-5-carboxypentyl]aminosulfonyl]4-chloro-2-hydroxyphenyl]-N'-(2-chlorophenyl) urea;

N-[3-[N"-(5-amino-5-carboxypentyl)aninosulfonyl]-4-chloro-2-hydroxyphenyl]-N'(2-chlorophenyl) urea hydrochloride;

N-[3-[N"-(5-amino-5-carboxypentyl)aninosulfonyl]-4-chloro-2-hydroxyphenyl]-N'(2,3-dichlorophenyl) urea hydrochloride;

N-[3-(N"-(5-amino-5-carboxypentyl)aninosulfonyl]-4-chloro-2-hydroxyphenyl]-N'(2-bromophenyl) urea hydrochloride;

N-[4-chloro-3-(1,1-dioxidothiomorpholinosulfonyl)-2-hydroxyphenyl]-N'-(2,3-dichlorophenyl) urea;

N-(2-bromophenyl)-N'-[4-chloro-3-(1,1-dioxidothiomorpholinosulfonyl)-2-hydroxyphenyl] urea;

N-[4-chloro-3-(1,1-dioxidothiomorpholinosulfonyl)-2-hydroxyphenyl]-N'-(2-chlorophenyl) urea;

N-[3-[N"-[2-(tert-butoxycarbonylamino)ethyl]aminosulfonyl]-4-chloro-2-hydroxyphenyl]-N'-(2,3-dichlorophenyl) urea;

N-[3-[N"-(2-aminoethyl)aminosulfonyl]-4-chloro-2-hydroxyphenyl]-N'-(2,3-dichlorophenyl) urea trifluoroacetate;

N-[3-[N"-[2-(tert-butoxycarbonylamino)ethyl]aminosulfonyl -4-chloro-2-hydroxyphenyl]-N'-(2-chlorophenyl) urea;

N-[3-[N"-(2-aminoethyl)aminosulfonyl]-4-chloro-2-hydroxyphenyl]-N'-(2-chlorophenyl) urea trifluoroacetate;

N-[4-chloro-2-hydroxy-3-(N",N"-dimethylaminosulfonyl)phenyl]-N'-(2-chlorophenyl) urea.;

N-[4-chloro-2-hydroxy-3-(aminosulfonyl)phenyl]-N'(2-bromo-3-fluorophenyl) urea;

N-[4-chloro-2-hydroxy-3-(aminosulfonyl)phenyl]-N (2-chloro-3-fluorophenyl) urea;

N-(2-bromophenyl)-N'-[4-chloro-3-[(1-ethyl-pyrrolidin-2-yl)methylaminosulfonyl]-2-hydroxyphenyl] urea hydrochloride;

N-[4-chloro-3-[(1-ethyl-pyrrolidin-2-yl)methylaminosulfonyl]-2-hydroxyphenyl] N'-(2,3-dichlorophenyl) urea hydrochloride; and N-[4-chloro-3-[(1-ethyl-pyrrolidin-2-yl)methylaminosulfonyl]-2-hydroxyphenyl]-N'-(2-chlorophenyl) urea hydrochloride; or a pharmaceutically acceptable salt thereof.

12. A compound according to claim 11 which is selected from the group consisting of:

N(4-chloro-2-hydroxy-3-aminosulfonylphenyl)-N'-(2,3-dichlorophenyl) urea;

N[4-chloro-2-hydroxy-3-S-(−)-(2-methoxymethyl)pyrrolidin-1-yl]sulfonylphenyl]-N'-(2,3-dichlorophenyl) urea;

N[4-chloro-2-hydroxy-3-(N"-isoxazolidinylaminosulfonyl)phenyl]-N'-(2,3-dichlorophenyl)urea;

N[4-chloro-2-hydroxy-3-(1-oxidothiomorpholinosulfonyl)phenyl]-N'-(2,3-dichlorophenyl) urea; and N[4-chloro-3-[N",N"-di-(2-methoxyethyl)aminosulfonyl[-2-hydroxyphenyl]-N (2,3-dichlorophenyl) urea.

13. A compound according to claim 12 wherein the compound is in its sodium salt form.

14. A compound according to claim 11 wherein the compound is in its potassium salt form.

15. A pharmaceutical composition comprising a compound according to claim 1 and a pharmaceutically acceptable carrier or diluent.

16. A method of treating a chemokine mediated disease, wherein the chemokine binds to an IL-8 a or b receptor in a mammal, which method comprises administering to said mammal an] amount, effective to prevent the chemokine from binding with the IL-8 b receptor, of a compound of the formula according to claim 1.

* * * * *